(12) United States Patent
So et al.

(10) Patent No.: US 9,526,880 B2
(45) Date of Patent: Dec. 27, 2016

(54) 3-DIMENSIONAL LARGE CAPACITY CELL ENCAPSULATION DEVICE ASSEMBLY

(71) Applicant: ViaCyte, Inc., San Diego, CA (US)

(72) Inventors: Vincent So, San Diego, CA (US); Laura Martinson, San Diego, CA (US); Chad Green, San Diego, CA (US); Michael Scott, San Diego, CA (US); Mario Zamarripa, San Diego, CA (US)

(73) Assignee: VIACYTE, INC., San Diego, CA (US)

( * ) Notice: Subject to any disclaimer, the term of this patent is extended or adjusted under 35 U.S.C. 154(b) by 49 days.

(21) Appl. No.: 14/201,630

(22) Filed: Mar. 7, 2014

(65) Prior Publication Data

US 2014/0257515 A1    Sep. 11, 2014

Related U.S. Application Data

(60) Provisional application No. 61/774,443, filed on Mar. 7, 2013.

(51) Int. Cl.
*A61F 2/02* (2006.01)
*A61M 31/00* (2006.01)

(52) U.S. Cl.
CPC ............ *A61M 31/002* (2013.01); *A61F 2/022* (2013.01); *A61M 2202/09* (2013.01); *A61M 2205/04* (2013.01)

(58) Field of Classification Search
CPC .................................................... A61F 2/022
See application file for complete search history.

(56) References Cited

U.S. PATENT DOCUMENTS

| | | |
|---|---|---|
| 2,500,388 A | 3/1950 | Simons |
| 2,519,983 A | 8/1950 | Simons |
| 2,594,272 A | 4/1952 | Kauck et al. |
| 2,616,927 A | 11/1952 | Kauck et al. |
| 3,929,971 A | 12/1975 | Roy |
| 4,298,002 A | 11/1981 | Ronel et al. |
| 4,723,953 A | 2/1988 | Rosenbaum et al. |
| 4,788,339 A | 11/1988 | Moore et al. |
| 4,968,733 A | 11/1990 | Müller et al. |
| 4,976,859 A | 12/1990 | Wechs |
| 5,011,494 A | 4/1991 | von Recum et al. |
| 5,026,365 A | 6/1991 | Rossini et al. |
| 5,100,392 A | 3/1992 | Orth et al. |
| 5,158,881 A | 10/1992 | Aebischer et al. |

(Continued)

FOREIGN PATENT DOCUMENTS

| | | |
|---|---|---|
| WO | WO 91/02498 A1 | 3/1991 |
| WO | WO 91/10425 | 7/1991 |

(Continued)

OTHER PUBLICATIONS

Alink et al., "The Effect of Cooling Rate and of Dimethyl Sulfoxide Concentration on Low Temperature Preservation of Neonatal Rat Heart Cells", *Cryobiology*, 1976, vol. 13, p. 295-304.

(Continued)

*Primary Examiner* — Kara Johnson
(74) *Attorney, Agent, or Firm* — Mark D. Wieczorek; Mayer & Williams PC

(57) ABSTRACT

Disclosed herein are implantable 3-dimensional large capacity device assemblies, specifically, large capacity device assemblies for encapsulating pancreatic progenitor cells for treatment of diabetes.

17 Claims, 43 Drawing Sheets

(56) References Cited

U.S. PATENT DOCUMENTS

| | | |
|---|---|---|
| 5,219,361 A | 6/1993 | von Recum et al. |
| 5,284,761 A | 2/1994 | Aebischer et al. |
| 5,314,471 A | 5/1994 | Brauker et al. |
| 5,324,518 A | 6/1994 | Orth et al. |
| 5,344,454 A | 9/1994 | Clarke et al. |
| 5,421,923 A | 6/1995 | Clarke et al. |
| 5,453,278 A | 9/1995 | Chan et al. |
| 5,545,223 A | 8/1996 | Neuenfeldt et al. |
| 5,549,675 A | 8/1996 | Neuenfeldt et al. |
| 5,554,148 A | 9/1996 | Aebischer et al. |
| 5,569,462 A | 10/1996 | Martinson et al. |
| 5,593,440 A | 1/1997 | Brauker et al. |
| 5,605,693 A | 2/1997 | Seare, Jr. |
| 5,624,674 A | 4/1997 | Seare, Jr. |
| 5,653,756 A | 8/1997 | Clarke et al. |
| 5,713,888 A | 2/1998 | Neuenfeldt et al. |
| 5,733,336 A | 3/1998 | Neuenfeldt et al. |
| 5,738,673 A | 4/1998 | Mills et al. |
| 5,741,330 A | 4/1998 | Brauker et al. |
| 5,782,912 A | 7/1998 | Brauker et al. |
| 5,800,529 A | 9/1998 | Brauker et al. |
| 5,807,406 A | 9/1998 | Brauker et al. |
| 5,882,354 A | 3/1999 | Brauker et al. |
| 5,902,745 A | 5/1999 | Butler et al. |
| 5,964,261 A | 10/1999 | Neuenfeldt et al. |
| 5,964,804 A | 10/1999 | Brauker et al. |
| 6,060,640 A | 5/2000 | Pauley et al. |
| 6,156,305 A | 12/2000 | Brauker et al. |
| 6,365,385 B1 | 4/2002 | Opara |
| 6,520,997 B1 | 2/2003 | Pekkarinen et al. |
| 6,617,151 B1 | 9/2003 | Newman et al. |
| 6,773,458 B1 | 8/2004 | Brauker et al. |
| 7,192,450 B2 | 3/2007 | Brauker et al. |
| 7,510,876 B2 | 3/2009 | D'Amour et al. |
| 7,534,608 B2 | 5/2009 | Martinson et al. |
| 7,541,185 B2 | 6/2009 | D'Amour et al. |
| 7,625,753 B2 | 12/2009 | Kelly et al. |
| 7,695,963 B2 | 4/2010 | Agulnick et al. |
| 7,695,965 B2 | 4/2010 | Martinson et al. |
| 7,704,738 B2 | 4/2010 | D'Amour et al. |
| 7,958,585 B2 | 6/2011 | Zhang et al. |
| 7,993,916 B2 | 8/2011 | Agulnick et al. |
| 7,993,920 B2 | 8/2011 | Martinson et al. |
| 8,008,075 B2 | 8/2011 | Green et al. |
| 8,129,182 B2 | 3/2012 | D'Amour et al. |
| 8,178,878 B2 | 5/2012 | Chien et al. |
| 8,211,699 B2 | 7/2012 | Robins et al. |
| 8,216,836 B2 | 7/2012 | D'Amour et al. |
| 8,278,106 B2 | 10/2012 | Martinson et al. |
| 8,334,138 B2 | 12/2012 | Robins et al. |
| 8,338,170 B2 | 12/2012 | Kelly et al. |
| 8,425,928 B2 | 4/2013 | Martinson et al. |
| 8,623,645 B2 | 1/2014 | D'Amour et al. |
| 2005/0260623 A1 | 11/2005 | Trosko et al. |
| 2009/0105811 A1 | 4/2009 | Dinh et al. |
| 2011/0236457 A1 | 9/2011 | Kauper et al. |

FOREIGN PATENT DOCUMENTS

| | | |
|---|---|---|
| WO | WO 92/19195 A1 | 11/1992 |
| WO | WO 93/00439 A1 | 1/1993 |
| WO | WO 93/21902 A1 | 11/1993 |
| WO | WO 95/05452 A2 | 2/1995 |
| WO | WO 95/18584 A1 | 7/1995 |
| WO | WO 96/10966 | 4/1996 |
| WO | WO 96/32076 | 10/1996 |
| WO | WO 96/39100 A1 | 12/1996 |
| WO | WO 99/53021 A1 | 10/1999 |
| WO | WO 03/059072 | 7/2003 |
| WO | WO 2008/112190 A1 | 9/2008 |
| WO | WO 2010/057039 A2 | 5/2010 |
| WO | WO 2010/121024 A2 | 10/2010 |
| WO | WO 2012/115619 A1 | 8/2012 |

OTHER PUBLICATIONS

Bank et al., "Cryogenic Preservation of Rat Polymorphonuclear Leukocytes", *Blood Cells*, 1980, vol. 6, p. 65-81.

Baust et al., "Modulation of the cryopreservation cap: elevated survival with reduced dimethyl sulfoxide concentration", *Cryobiology*, 2002, vol. 45, p. 97-108.

Brauker et al., "Local inflammatory response around diffusion chambers containing xenografts. Nonspecific destruction of tissues and decreased local vascularization", *Transplantation* 61(12):1671-1677; 1996.

Brauker et al., "Neovascularization of synthetic membranes directed by membrane microarchitecture", *Journal of Biomedical Materials Research*, 29:1517-1524; 1995.

Carlsson et al., "Measurements of Oxygen Tension in Native and Transplanted Rat Pancreatic Islets", *Diabetes*, 47(7):1027-1032; 1998.

Chung et al., "Human Embryonic Stem Cell Lines Generated without Embryo Destruction", *Cell Stem Cell*, 2(2), 113-117; 2008.

Dionne et al., "Effect of Oxygen on Isolated Pancreatic Tissue", *Trans. Am. Soc. Artf. Intern. Organs*, 35: 739-741; 1989.

Klimanskaya et al., "Human embryonic stem cell lines derived from single blastomeres", *Nature*, 444:481-485; 2006.

Korsgren et al., "Current Status of Clinical Islet Transplantation", *Transplantation* 79(10):1289-1293; 2005.

Kumagai-Braesch et al., "The TheraCyte™ Device Protects against Islet Allograft Rejection in Immunized Hosts", *Cell Transplantation*, 22:1137-1146; 2013.

Loudovaris et al., "Destruction of Xenografts But Not Allografts Within Cell Impermeable Membranes", *Transplantation Proceedings* 24:2291-2292; 1992.

Loudovaris et al., "CD4+ T cell mediated destruction of xenografts within cell-impermeable membranes in the absence of CD8+ T cells and B cells", *Transplantation* 61:1678-1684; 1996.

McKenzie et al., "Protection of Xenografts by a Combination of Immunoisolation and a Single Dose of Anti-CD4 Antibody", *Cell Transplantation* 10:183-193; 2001.

Rice et al., "Quantitative biomarkers of stem cell differentiation based on intrinsic two-photon excited fluorescence", *Journal of Biomedical Optics* Nov.-Dec. 2007; 12(6), 3 pages.

Tibell et al., "Survival of Macroencapsulated Allogeneic Parathyroid Tissue One Year After Transplantation in Nonimmunosuppressed Humans", *Cell Transplantation.* 10:591-599; 2001.

International Search Report and Written Opinion dated Jun. 26, 2014 for International Application No. PCT/US2014/022109, 9 pages.

U.S. Appl. No. 13/672,688, filed Nov. 8, 2012.
U.S. Appl. No. 13/761,078, filed Feb. 6, 2013.
U.S. Appl. No. 14/106,330, filed Dec. 13, 2013.
U.S. Appl. No. 29/408,366, filed Dec. 12, 2011.
U.S. Appl. No. 29/408,368, filed Dec. 12, 2011.
U.S. Appl. No. 29/408,370, filed Dec. 12, 2011.
U.S. Appl. No. 29/423,365, filed May 31, 2012.

International Preliminary Report on Patentability mailed Sep. 17, 2015, issued in connection with corresponding International Application No. PCT/US14/022109 (6 pages total).

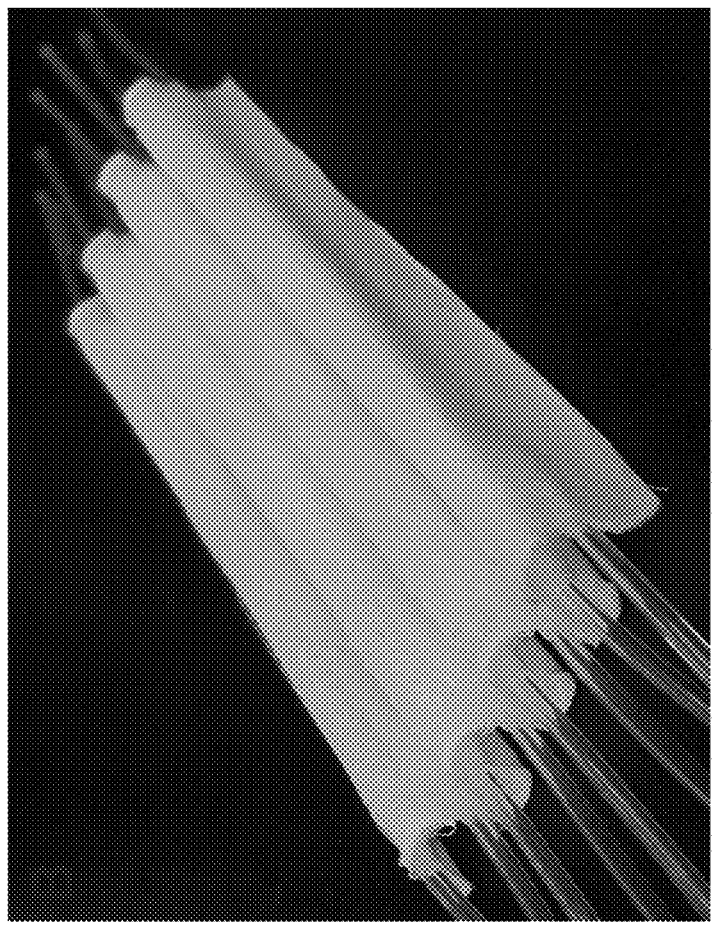
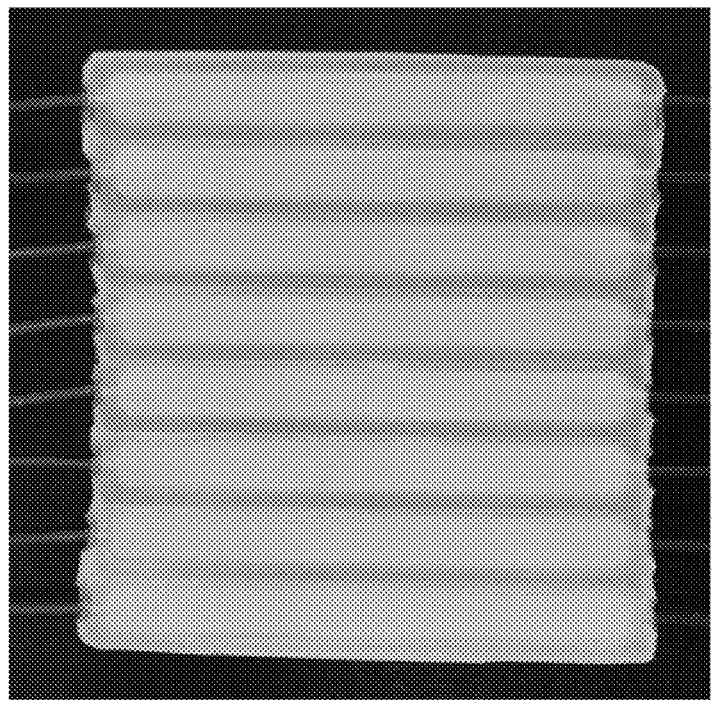
FIG. 4

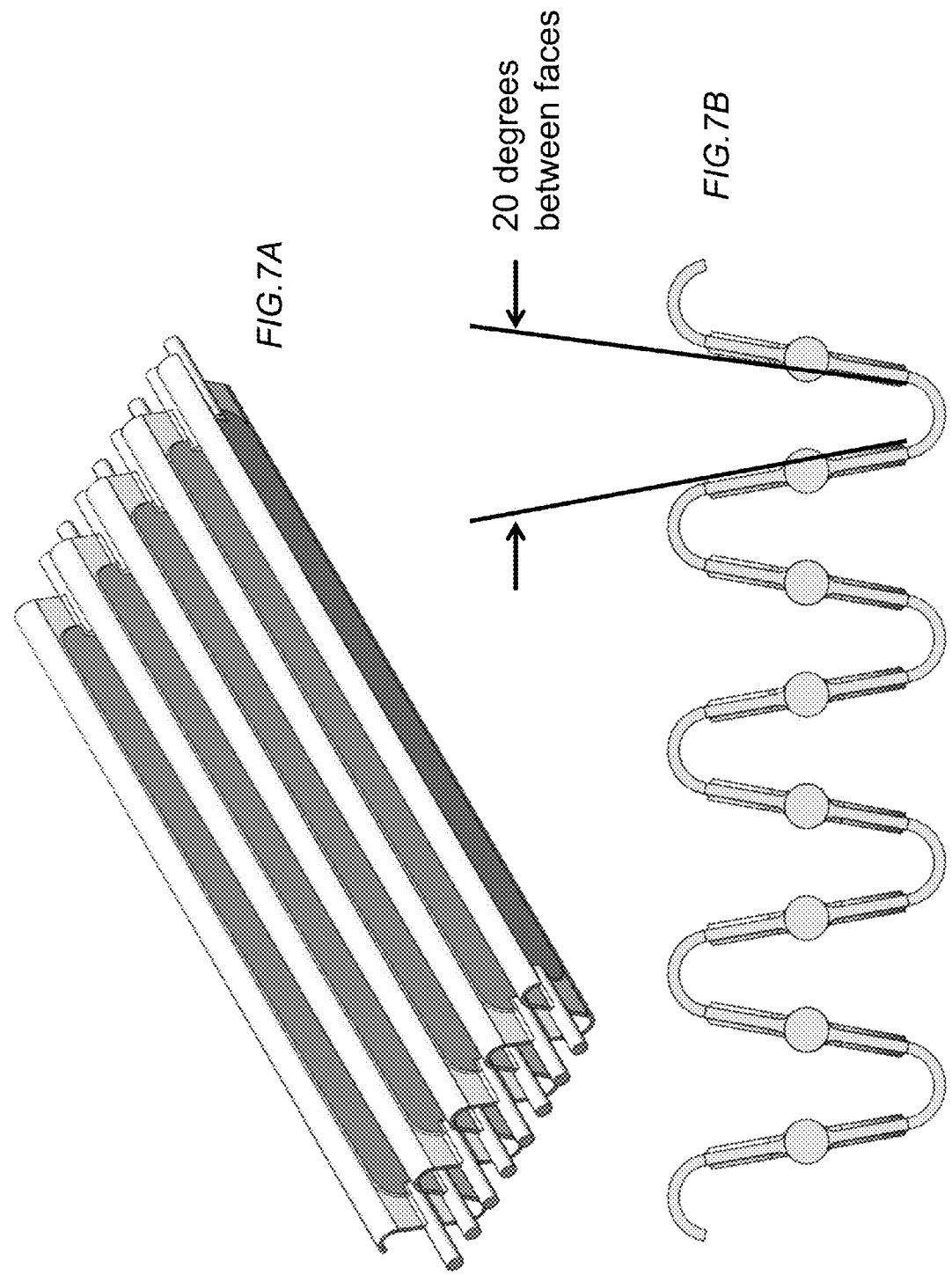

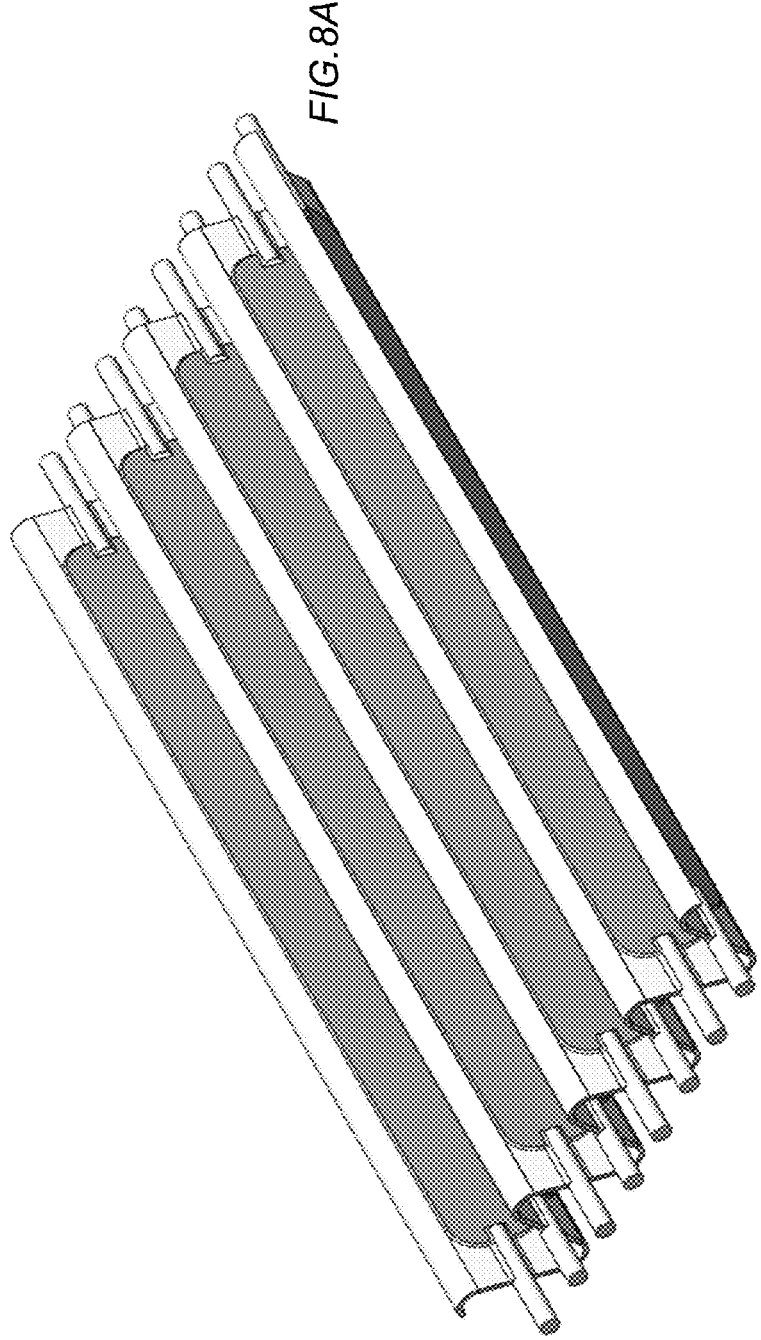
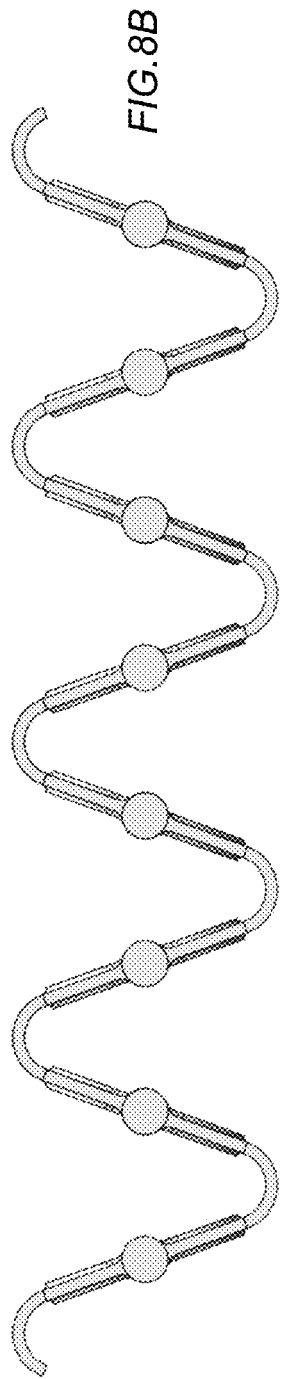
FIG.8A
FIG.8B

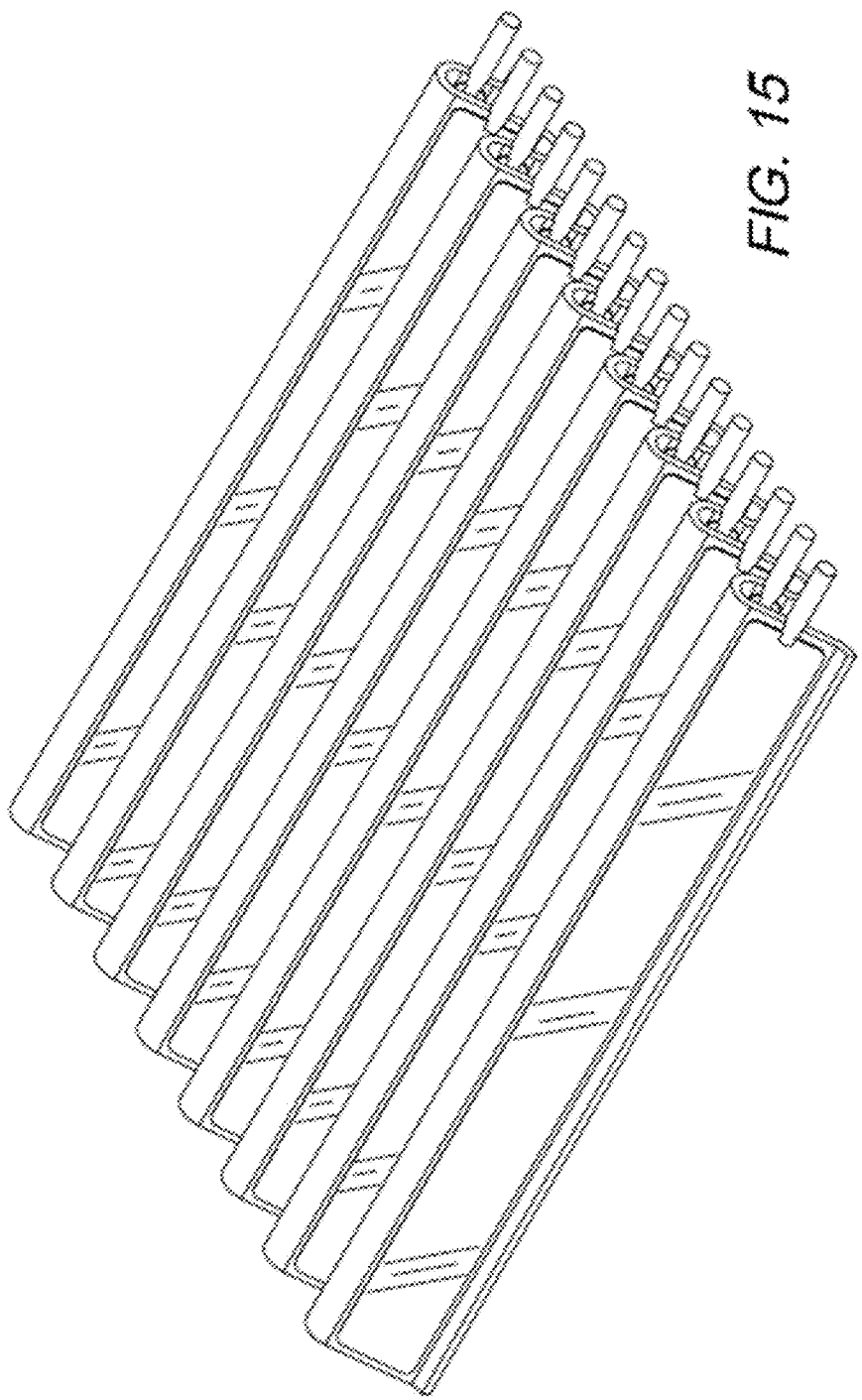

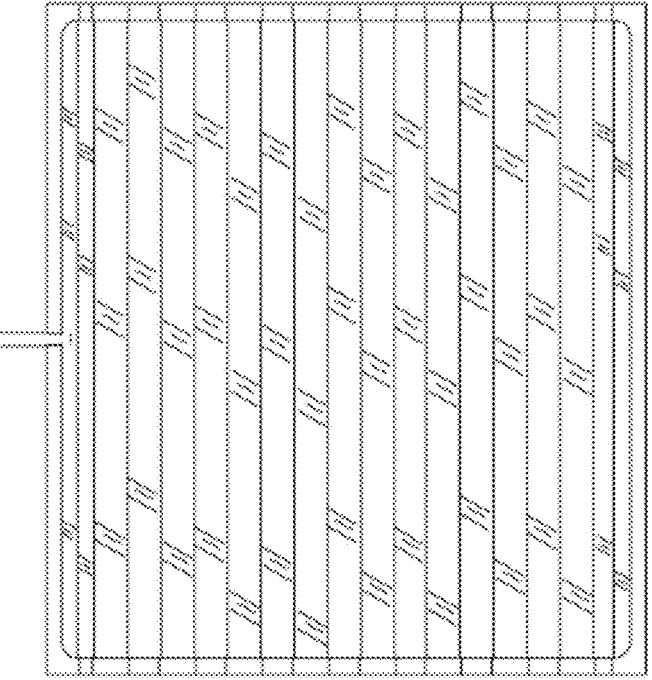
FIG. 23  FIG. 25
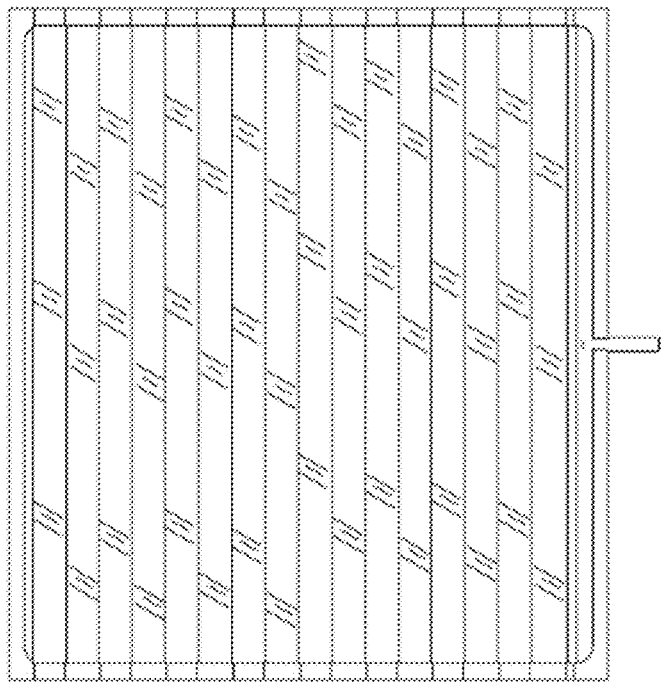
FIG. 24  FIG. 26

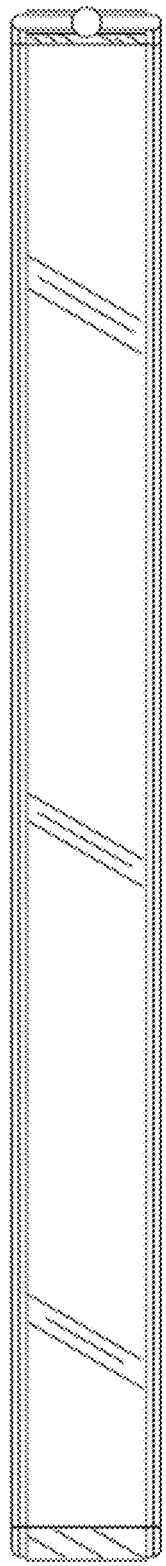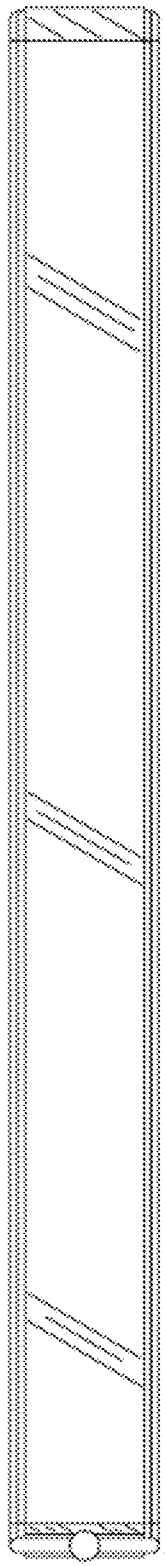

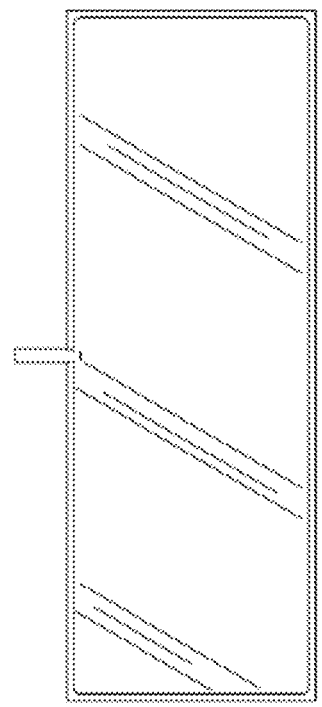
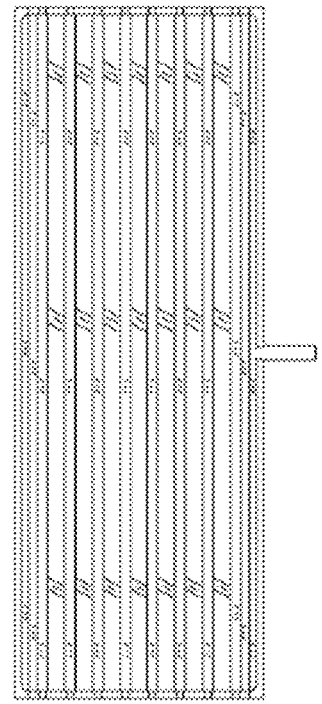
FIG. 51
FIG. 52
FIG. 53
FIG. 54

FIG. 73

3-DIMENSIONAL LARGE CAPACITY CELL ENCAPSULATION DEVICE ASSEMBLY

CROSS-REFERENCE TO RELATED APPLICATIONS

This application claims the benefit of U.S. Provisional Application No. 61/774,443 filed Mar. 7, 2013, which is hereby incorporated in its entirety and for all purposes.

GOVERNMENT FUNDING

This research was made possible, in part, by a loan from the California Institute for Regenerative Medicine (CIRM). CIRM has certain rights in the invention.

FIELD OF THE INVENTION

The field of invention relates to medical devices and cell therapies. In particular, embodiments described herein relate to the large capacity encapsulation of cells by a semipermeable implantable device.

SUMMARY OF THE INVENTION

Embodiments described herein relate to a cell encapsulating assembly, a large capacity device assembly or a 3-dimensional large capacity devise assembly for implanting a living cell population into a mammalian host.

In one embodiment, the large capacity device assembly comprises at least two cell chambers and at last two configurations folded and unfolded wherein the folded configuration has a smaller footprint than the unfolded configuration.

Footprint as used herein refers to a two-dimensional planar projection of the device onto the anatomical site. In one embodiment, there is provided a large capacity device assembly for implanting into a mammalian host, the assembly is comprised of at least two chambers for encapsulating living cells, wherein the assembly is further comprised of a first seal at a peripheral edge of the assembly, thereby forming the encapsulating assembly, and at least a second seal, wherein the second seal is within said cell encapsulating assembly and forms the inner periphery of a the cell chambers. The cell encapsulating assembly can comprise a third or fourth seal which further partitions each of the cell chambers, i.e., a partition seal.

In one embodiment, the large capacity device assembly is three-dimensional and takes the form of a roman shade, U-shape, scallop, fin-shape, flat tube, coil, fan, radiator or any other three-dimensional shape capable of encapsulating an effective therapeutic dose of cells while constraining the footprint of the assembly.

In one embodiment, the large capacity device assembly is a three-dimensional assembly capable of intercalating into the body of the host and maintains its shape, form and location.

In one embodiment, the cell chambers of the cell encapsulating assembly comprise a cell luminal matrix, wherein the matrix provides for improved oxygen and nutrient exchange to the cells in the chamber, in particular, to the cells at the core or center of the chamber. The luminal matrix can comprise an elastomeric matrix including but not limited to a silicone elastomer, such as a silicone foam or fibers. In another aspect, the luminal matrix is any biostable agent that functions as a conduit and provides and increases the flow of oxygen and nutrients to the encapsulated cells, thereby promoting cell survival in the short and long term post implantation.

In one embodiment, the large capacity device assembly comprises at least two cell chambers and at last two configurations folded and unfolded wherein the folded configuration has a smaller footprint but the same surface area as the unfolded configuration.

In one embodiment, the large capacity device assembly comprises at least two cell chambers in a folded configuration which flattens or unfolds once implanted in a mammalian host. With this embodiment, the incision site is small but once implanted the assembly flatten out to reduce extrusion from the host and maximize intercalation.

In one embodiment, the large capacity device assembly comprises a first unfolded configuration, a second, folded configuration and a third implanted configuration which is flatter than the folded configuration.

In one embodiment, the large capacity device assembly comprises at least two cell chambers in a folded configuration which has at least 2 times more living cells than a flat assembly with the same footprint.

Preferred features and aspects of the present invention are as follows.

In preferred embodiments the assembly comprises more than 1 cell chambers for encapsulating living cells. In preferred embodiments the assembly comprises at least 2 cell chambers for encapsulating living cells.

In preferred embodiments the assembly comprises, a cell-free region. In preferred embodiments the assembly comprises the cell free region is along the longest axis separating the cell chambers. In preferred embodiments the assembly comprises the cell free region is bent to form folds. In preferred embodiments the folds decrease the footprint of the assembly as compared to the assembly without the folds.

In preferred embodiments the assembly maintains substantially the same cell volume capacity with or without the folds.

In preferred embodiments the assembly comprises a semipermeable membrane.

In preferred embodiments the assembly comprises a two, three, four, five, six, seven, eight or more cell chambers.

In preferred embodiments the assembly comprises at least one loading port. In preferred embodiments, the assembly comprises two loading ports.

In preferred embodiments the living cells are definitive endoderm-lineage cells. In preferred embodiments the living cells are human pancreatic and duodenal homeobox gene 1 (PDX1)-positive pancreatic progenitor cells. In preferred embodiments the living cells are human endocrine precursor cells. In preferred embodiments the living cells are human immature beta cells. In preferred embodiments the cells are dispersed within the chamber.

In preferred embodiments the cell chamber has a matrix with a plurality of interconnected cavities or pores to disperse the living cells and to improve oxygen distribution inside the cell chamber. In preferred embodiments the interconnected cavities have different cavity dimensions. In preferred embodiments the matrix is polydimethylsiloxane (PDMS), polydimethylsiloxane monoacrylate, and polydimethylsiloxane monomethacrylate. In preferred embodiments the matrix is a silicone elastomer.

In preferred embodiments the cell chambers are parallel to each other. In preferred embodiments the cell chambers are separated by about 20 degrees. In preferred embodiments the cell chambers are separated by about 40 degrees. In preferred embodiments the chamber comprises a partition seal within the cell chamber.

BRIEF DESCRIPTION OF THE DRAWINGS

FIG. 3B is a cross-section of FIG. 3A showing the 3-dimensional nature of the device assembly folded at angles such that the cell chambers are substantially parallel to each other.

FIGS. 4A-B are photographs of one embodiment of a 3-dimensional large capacity device assembly. FIG. 4A shows a flat, planar eight cell chamber device and FIG. 4B shows the same FIG. 4A device folded such that the cell chambers are substantially parallel to each other.

FIG. 5A is a 3-dimensional large capacity device assembly with dual ports; and is compared to the smaller capacity planar device shown in FIG. 5B.

FIG. 6A shows the 3-dimensional nature of the device assembly with the folds at angles such that the cell chambers are substantially parallel, or zero degrees of separation, to each other; FIG. 6B shows a top view of the device; and FIG. 6C shows a cross-section of the device.

FIGS. 7A-B are perspective views of one embodiment of a 3-dimensional large capacity device assembly with ports. FIG. 7A shows the 3-dimensional nature of the device assembly; and FIG. 7B shows a cross-section of the device with ports, with each cell chamber and port separated by about 20 degrees.

FIGS. 8A-B are perspective views of one embodiment of a 3-dimensional large capacity device assembly with ports. FIG. 8A shows the 3-dimensional nature of the device assembly; and FIG. 8B shows a cross-section of the device with ports, with each cell chamber and port separated by about 40 degrees.

FIG. 9A shows the 3-dimensional nature of the device assembly; FIG. 9B shows a top view of the device; and FIG. 9C shows a cross-section of the device without ports. The cell chambers are parallel to each other but at an angle.

FIG. 10A shows a cross-section of the tubular device of FIG. 10B such that FIG. 10B is cut in half to show details of the winding cell chamber(s); FIG. 10B shows the flat sheet tubular device with openings at both ends; and FIG. 10C shows the top view of the tubular device.

FIG. 11A shows a 3-dimensional large capacity device; FIG. 11B shows the top view of the device; FIG. 11C shows a cross-section of the device with the cell chambers parallel to each other, with one side attached at the base.

FIG. 12A shows a 3-dimensional large capacity device; FIG. 13B shows the top view of the device; FIG. 12C shows a cross-section of the device with the parallel cell chambers interconnected to a base.

FIGS. 13A-B are perspective top views of two embodiments of cell-encapsulation large capacity device assemblies containing eight cell chambers having either one (FIG. 13A) or two ports (FIG. 13B) prior to forming or folding to become a 3-dimensional large capacity device assembly.

FIG. 15 is a perspective view of the 3-dimensional large capacity cell encapsulation device or assembly with multiple cell chambers and a single port per cell chamber.

FIG. 23 is a back elevation view of the 3-dimensional large capacity cell encapsulation device or assembly with multiple cell chambers and a single port per cell chamber.

FIG. 24 is a front elevation view of the 3-dimensional large capacity cell encapsulation device or assembly with multiple cell chambers and a single port per cell chamber.

FIG. 25 is a top plan view of the 3-dimensional large capacity cell encapsulation device or assembly with multiple cell chambers and a single port per cell chamber.

FIG. 26 is a bottom plan view of the 3-dimensional large capacity cell encapsulation device or assembly with multiple cell chambers and a single port per cell chamber.

FIG. 41 is a right elevation view of the 3-dimensional large capacity cell encapsulation device or assembly constructed from single modular units with cell chambers on each side.

FIG. 42 is a left elevation view of the 3-dimensional large capacity cell encapsulation device or assembly constructed from single modular units with cell chambers on each side.

FIG. 51 is a back elevation view of the 3-dimensional large capacity cell encapsulation device or assembly with a single cell chamber and port.

FIG. 52 is a front elevation view of the 3-dimensional large capacity cell encapsulation device or assembly with a single cell chamber and port.

FIG. 53 is a top plan view of the 3-dimensional large capacity cell encapsulation device or assembly with a single cell chamber and port.

FIG. 54 is a bottom plan view of the 3-dimensional large capacity cell encapsulation device or assembly with a single cell chamber and port.

FIGS. 73A-B are photo images of histological sections of explanted PEC grafts with silicone hollow fibers. The hollow fibers are the white round structures between the device's semi-permeable membranes. The sections were stained with standard hematoxylin and eosin stain (FIG. 73A) and anti-insulin antibody which stains those cells expressing insulin brown (FIG. 73B)

DETAILED DESCRIPTION OF THE PREFERRED EMBODIMENT

Figure 1:
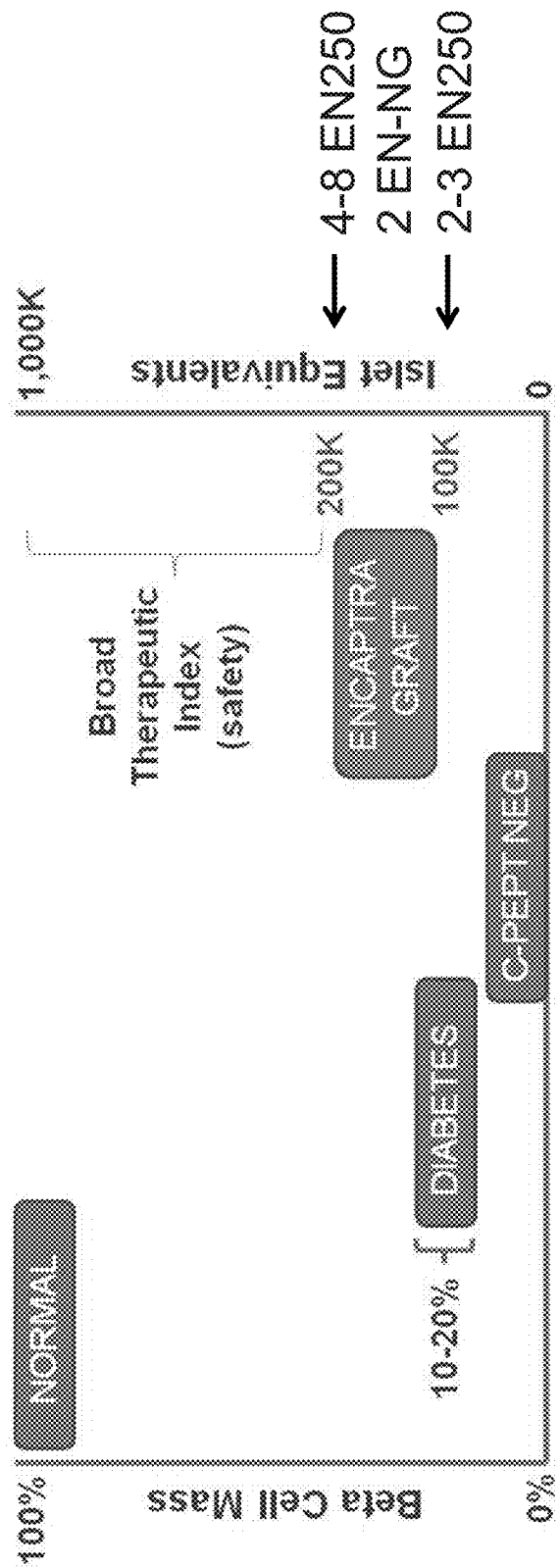
FIG. 1 is a graph showing beta cell mass and relative islet equivalents (IEQ)/kg body weight (BW). The graph also describes diabetes onset as having about 10-20% beta cell mass whereas patients with less than 10% beta cell mass have no discernible serum c-peptide; and although there is a broad therapeutic index range, about 200,000 IEQ is a potential efficacious dose to be delivered by an encapsulated PEC graft.
Figure 2:
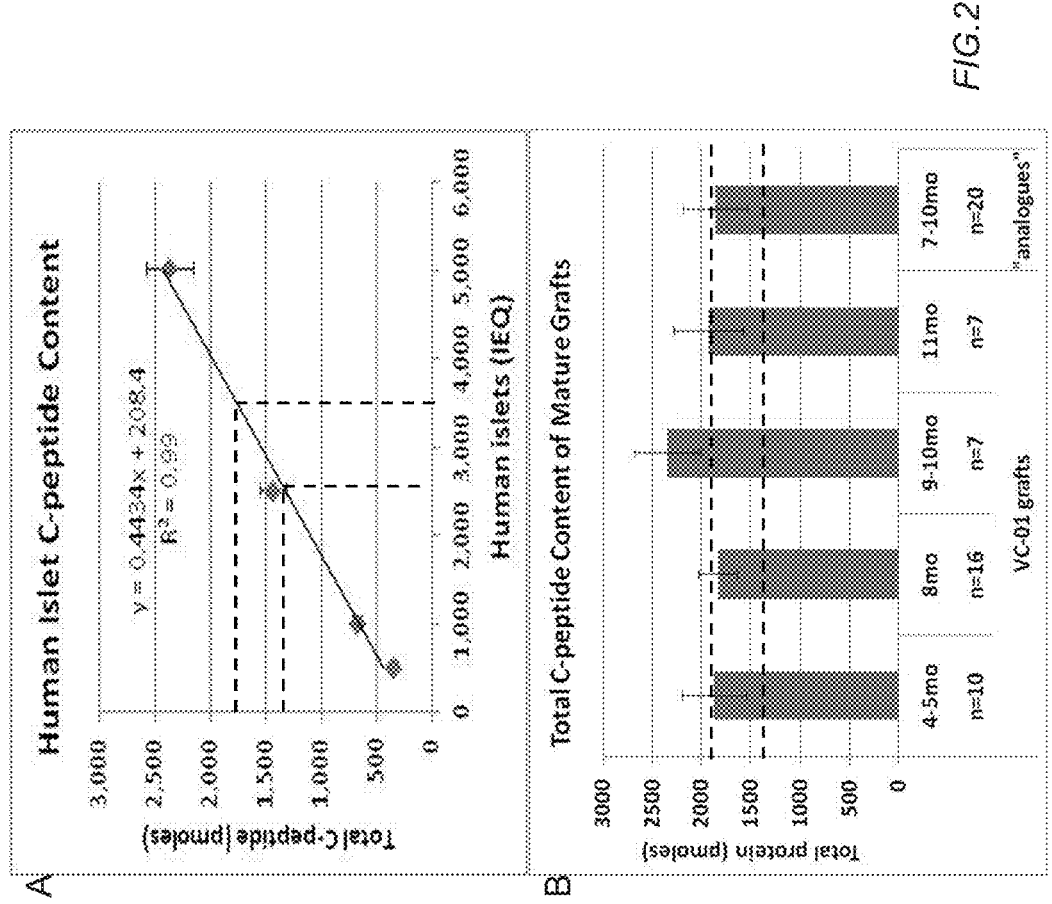
FIG. 2 are graphs correlating human islet IEQ and C-peptide to that of C-peptide from mature encapsulated pancreatic endoderm cell (PEC) grafts.

Unless otherwise noted, the terms used herein are to be understood according to conventional usage by those of ordinary skill in the relevant art. Throughout this application, various patent and non-patent publications are referenced. The disclosures of all of these publications and those references cited within those publications in their entireties are hereby incorporated by reference into this application in their entirety in order to more fully describe the state of the art to which this patent pertains.

Also, for the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about".

Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

In one embodiment, a bio-compatible implantable device is provided. Such, macro-encapsulating devices are described in U.S. Pat. Nos. 6,773,458; 6,156,305; 6,060,640; 5,964,804; 5,964,261; 5,882,354; 5,807,406; 5,800,529; 5,782,912; 5,741,330; 5,733,336; 5,713,888; 5,653,756; 5,593,440; 5,569,462; 5,549,675; 5,545,223; 5,453,278; 5,421,923; 5,344,454; 5,314,471; 5,324,518; 5,219,361; 5,100,392; and 5,011,494 all of which are assigned to Baxter.

Other suitable embodiments described herein are further described in detail in at least U.S. Pat. No. 8,211,699, METHODS FOR CULTURING PLURIPOTENT STEM CELLS IN SUSPENSION USING ERBB3 LIGANDS, issued Jul. 3, 2012; U.S. Pat. No. 7,958,585, PREPRIMITIVE STREAK AND MESENDODERM CELLS, issued Jul. 26, 2011; U.S. Pat. Nos. 7,510,876 and 8,216,836 DEFINITIVE ENDODERM, issued Mar. 31, 2009 and Jul. 10, 2012, respectively; U.S. Pat. No. 7,541,185, METHODS FOR IDENTIFYING FACTORS FOR DIFFERENTIATING DEFINITIVE ENDODERM, issued Jun. 2, 2009; U.S. Pat. No. 7,625,753, EXPANSION OF DEFINITIVE ENDODERM, issued Dec. 1, 2009; U.S. Pat. No. 7,695,963, METHODS FOR INCREASING DEFINITIVE ENDODERM PRODUCTION, issued Apr. 13, 2010; U.S. Pat. No. 7,704,738, DEFINITIVE ENDODERM, issued Apr. 27, 2010; U.S. Pat. No. 7,993,916, METHODS FOR INCREASING DEFINITIVE ENDODERM PRODUCTION, issued Aug. 9, 2011; U.S. Pat. No. 8,008,075, STEM CELL AGGREGATE SUSPENSION COMPOSITIONS AND METHODS OF DIFFERENTIATION THEREOF, issued Aug. 30, 2011; U.S. Pat. No. 8,178,878, COMPOSITIONS AND METHODS FOR SELF-RENEWAL AND DIFFERENTIATION IN HUMAN EMBRYONIC STEM CELLS, issued May 29, 2012; U.S. Pat. No. 8,216,836, METHODS FOR IDENTIFYING FACTORS FOR DIFFERENTIATING DEFINITIVE ENDODERM, issued Jul. 10, 2012; U.S. Pat. Nos. 7,534,608, 7,695,965, and 7,993,920 issued May 19, 2009, Apr. 13, 2010; and Aug. 9, 2011, respectively; U.S. Pat. No. 8,129,182, ENDOCRINE PRECURSOR CELLS, PANCREATIC HORMONE EXPRESSING CELLS AND METHODS OF PRODUCTION, issued Mar. 6, 2012; U.S. Pat. No. 8,338,170 METHODS FOR PURIFYING ENDODERM AND PANCREATIC ENDODERM CELLS DERIVED FROM HUMAN EMBRYONIC STEM CELLS, issued Dec. 25, 2012; U.S. Pat. No. 8,334,138, METHODS AND COMPOSITIONS FOR FEEDER-FREE PLURIPOTENT STEM CELL MEDIA CONTAINING HUMAN SERUM, issued Dec. 18, 2012; U.S. Pat. No. 8,278,106, ENCAPSULATION OF PANCREATIC CELLS DERIVED FROM HUMAN PLURIPOTENT STEM CELLS, issued Oct. 2, 2012; U.S. Pat. No. 8,338,170, titled METHOD FOR PURIFYING ENDODERM AND PANCREATIC ENDODERM CELLS DERIVED FROM HUMAN EMBRYONIC STEM CELLS (CYTHERA.063A), issued Dec. 25, 2012; U.S. application Ser. No. 13/761,078, CELL COMPOSITIONS DERIVED FROM DEDIFFERENTIATED REPROGRAMMED CELLS, filed Feb. 6, 2013; U.S. application Ser. No. 13/672,688, SCALABLE PRIMATE PLURIPOTENT STEM CELL AGGREGATE SUSPENSION CULTURE AND DIFFERENTIATION THEREOF, filed Nov. 8, 2012;

Design patent applications 29/408,366; 29/408,368 and 29/408,370 filed Dec. 12, 2001 and 29/423,365 May 31, 2012.

Definitions

As used herein, "about" as used herein means that a number referred to as "about" comprises the recited number plus or minus 1-10% of that recited number. For example, "about" 100 cells can mean 95-105 cells or as few as 99-101 cells depending on the situation. Whenever it appears herein, a numerical range such as "1 to 20" refers to each integer in the given range; e.g., "1 to 20 cells" means 1 cell, 2 cells, 3 cells, etc., up to and including 20 cells. Where about modifies a range expressed in non-integers, it means the recited number plus or minus 1-10% to the same degree of significant figures expressed. For example, about 1.50 to 2.50 mM can mean as little as 1.35 M or as much as 2.75M or any amount in between in increments of 0.01.

As used herein, in connection with the composition of a cell population, the term "essentially" or "substantially" means predominantly or mainly.

As used herein, the term "effective amount" or equivalents thereof of a compound refers to that concentration of the compound that is sufficient in the presence of the remaining components of the defined medium to effect the stabilization of the differentiable cell in culture for greater than one month in the absence of a feeder cell and in the absence of serum or serum replacement. This concentration is readily determined by one of ordinary skill in the art.

As used herein when referring to a "cell", "cell line", "cell culture" or "cell population" or "population of cells", the term "isolated" refers to being substantially separated from the source of the cells such that the living cell, cell line, cell culture, cell population or population of cells are capable of being cultured in vitro for extended periods of time. In addition, the term "isolating" can be used to refer to the physical selection of one or more cells out of a group of two or more cells, wherein the cells are selected based on cell morphology and/or the expression of various markers.

As used herein, the term "substantially" refers to a great extent or degree, e.g. "substantially similar" in context would be used to describe one method which is to great extent or degree similar or different to another method. However, as used herein, the term "substantially free", e.g., "substantially free" or "substantially free from contaminants," or "substantially free of serum" or "substantially free of insulin or insulin like growth factor" or equivalents thereof, is meant that the solution, media, supplement, excipient and the like, is at least 98%, or at least 98.5%, or at least 99%, or at least 99.5%, or at least 100% free of serum, contaminants or equivalent thereof. In one embodiment, there is provided a defined culture media with no serum, or is 100% serum-free, or is substantially free of serum. Conversely, as used herein, the term "substantially similar" or equivalents thereof is meant that the composition, process, method, solution, media, supplement, excipient and the like is meant that the process, method, solution etc., is at least 80%, at least 85%, at least 90%, at least 95%, or at least 99% similar to that previously described in the specification herein, or in a previously described process or method incorporated herein in its entirety.

As used herein, a cell suitable for transplantation refers to a cell or a population of cells sufficiently viable and/or functional for in vivo treatment of a metabolic disorder. For example, diabetes, or one or more symptoms thereof, can be ameliorated or reduced for a period of time following implantation of a cell suitable for transplantation into a subject suffering from diabetes. In one preferred embodiment, a cell or cell population suitable for transplantation is a pancreatic progenitor cell or population, or a PDX1-positive pancreatic progenitor cell or population, or an endocrine precursor cell or population, or a poly or singly-hormonal endocrine cell and/or any combination of cell or populations of cells, or PEC or even purified or enriched cells or populations of cells thereof.

Implantable Large Capacity Devices

One embodiment described herein relates to encapsulation devices, preferably cell encapsulation devices, preferably macro cell encapsulation devices, preferably large capacity device assemblies, preferably cell encapsulation device assemblies of any size consisting of devices of at least 1, 2, 3, 4, 5, 6, 7, 8, 9, 10 or more cell chambers. As used herein, a term "assembly" refers to a cell encapsulation device consisting of multiple or a plurality of cell chambers. In one embodiment, the assembly consists of at least 1, 2, 4, 5, 6, 7, 8, 9, 10 or more cell chambers. In another embodiment, the assembly is made such that an assembly can consist of any number of cell chambers (or a modular unit). For example, a modular unit can consist of 1, 2, 3, 4, 5, 6, 7, 8, 9, 10 or more cell chambers, which can depend on the number or dose of cells required for the treatment of the disease. Hence, as used herein, the term "device" can mean a single device consisting of one cell chamber such as that previously described or one device consisting of multiple cell chambers such as the 3-dimensional device or device assemblies described herein. Thus, in some instances device and assembly can be used interchangeably.

Figure 3:
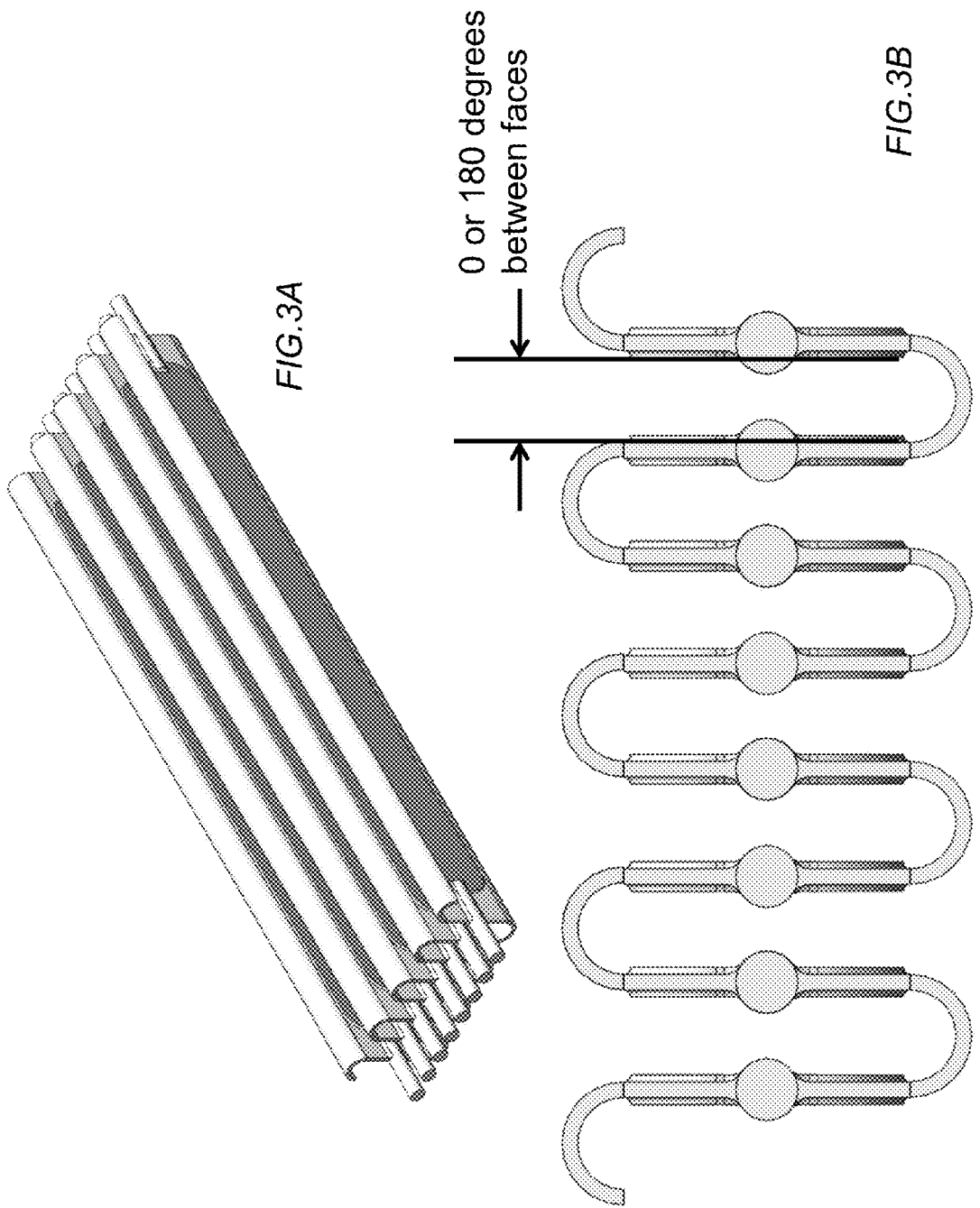
FIGS. 3A-B are perspective views of one embodiment of a 3-dimensional large capacity device assembly.
Figure 5:
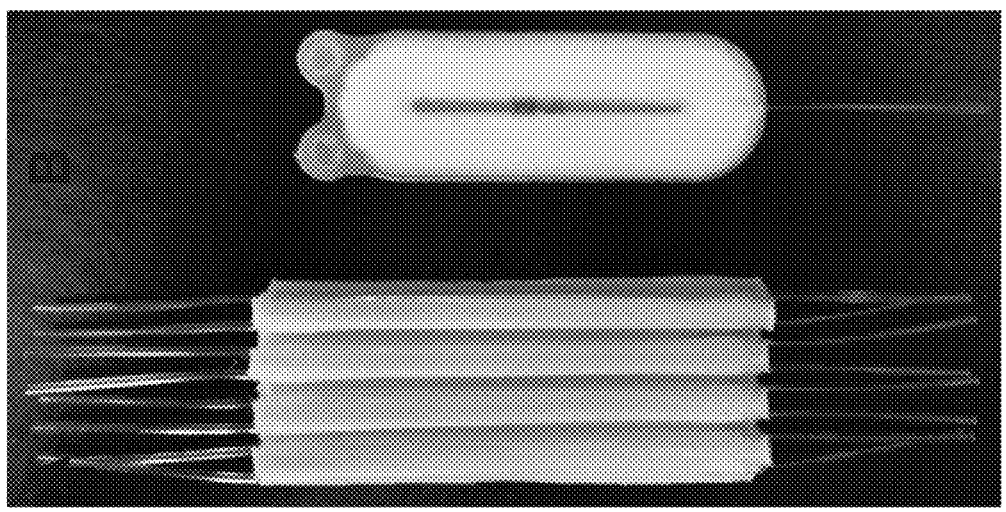
FIGS. 5A-B are photographs of cell encapsulation devices.
Figure 6:
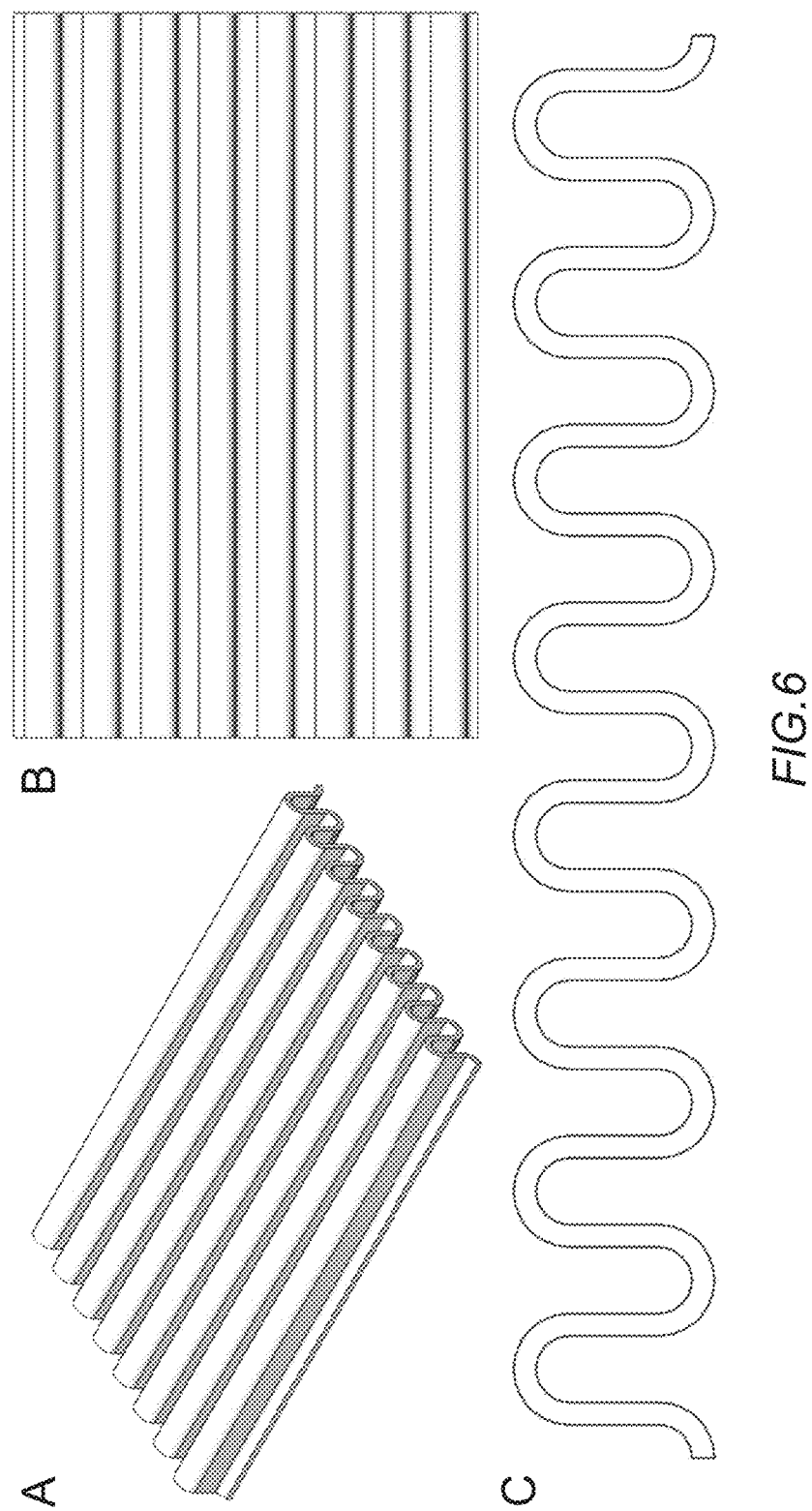
FIGS. 6A-C are perspective views of one embodiment of a 3-dimensional large capacity device assembly without ports.
Figure 9:
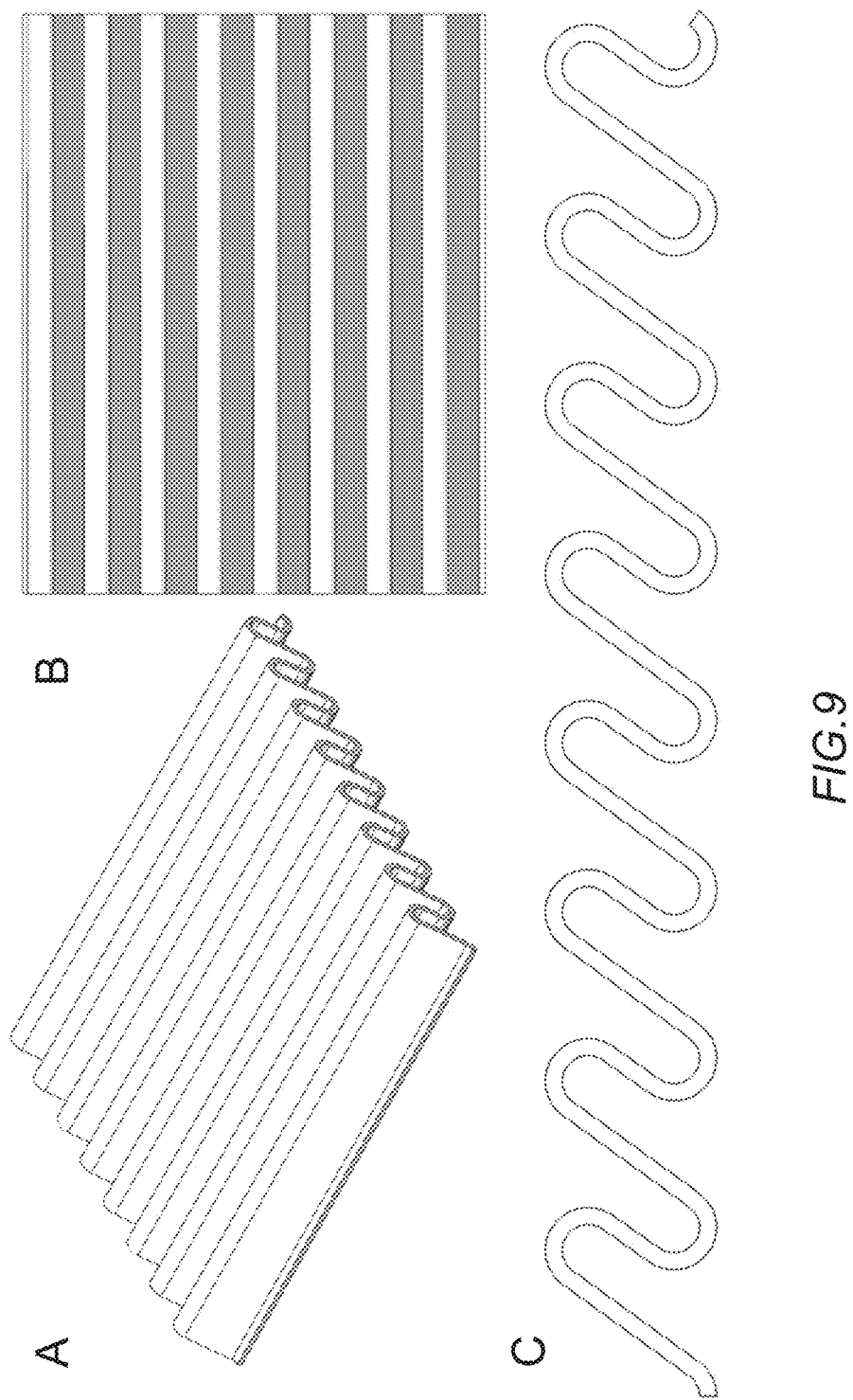
FIGS. 9A-C are perspective views of one embodiment of a 3-dimensional large capacity device assembly without ports ("roman shade").
Figure 10:
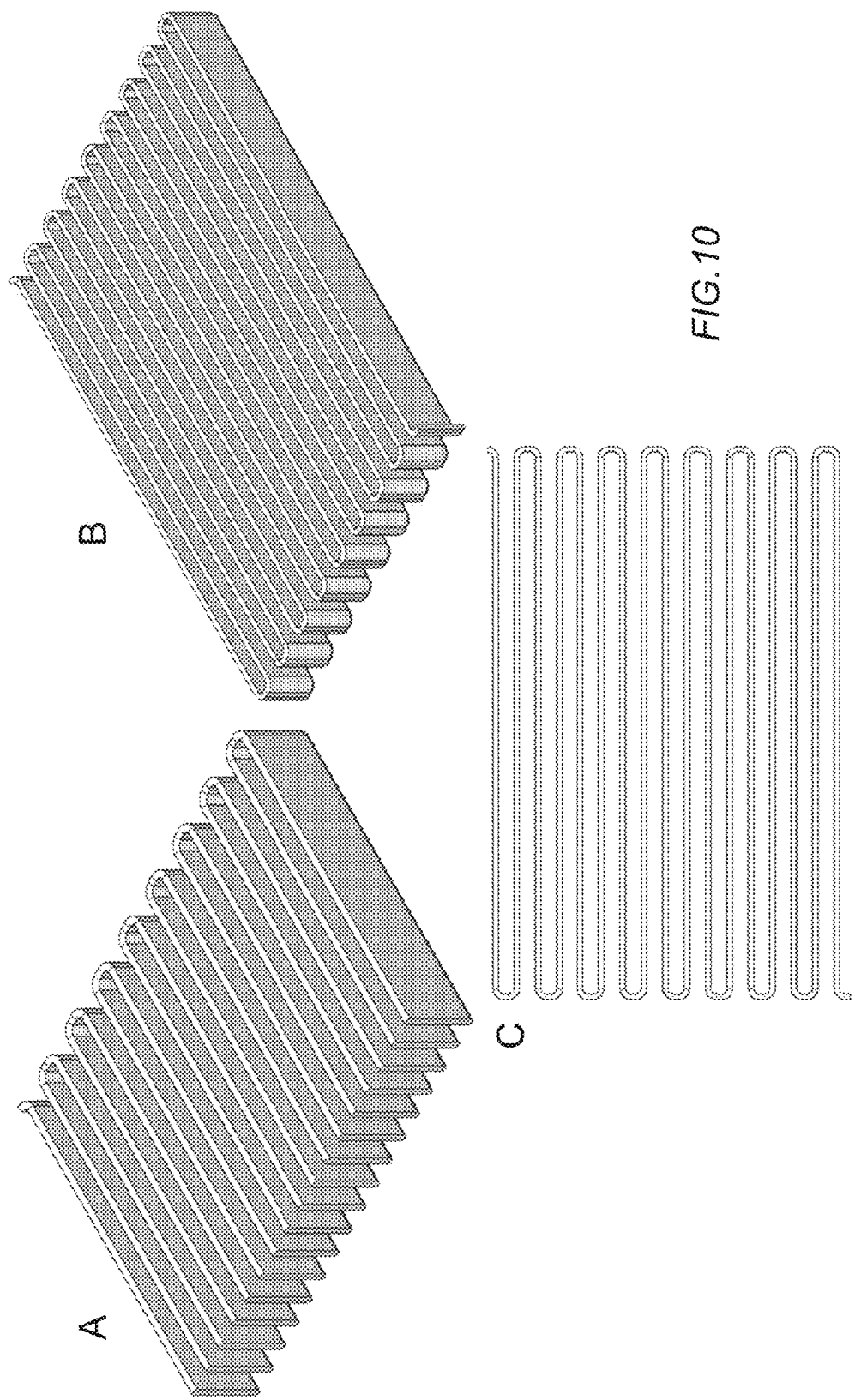
FIGS. 10A-C are perspective views of one embodiment of a 3-dimensional large capacity device assembly wherein the chamber is a continuous tube.
Figure 11:
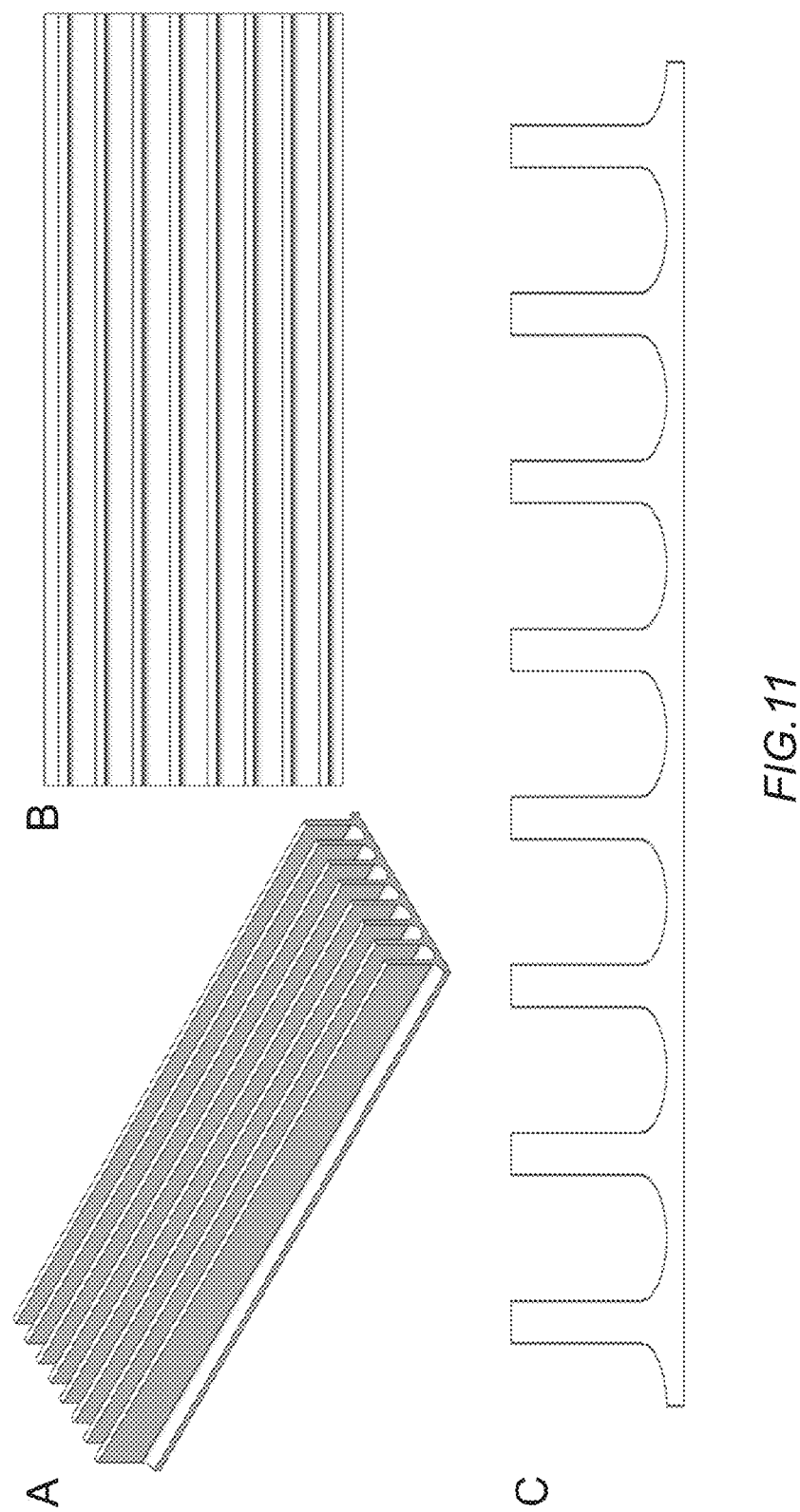
FIGS. 11A-C are perspective views of one embodiment of a 3-dimensional large capacity device assembly.
Figure 12:
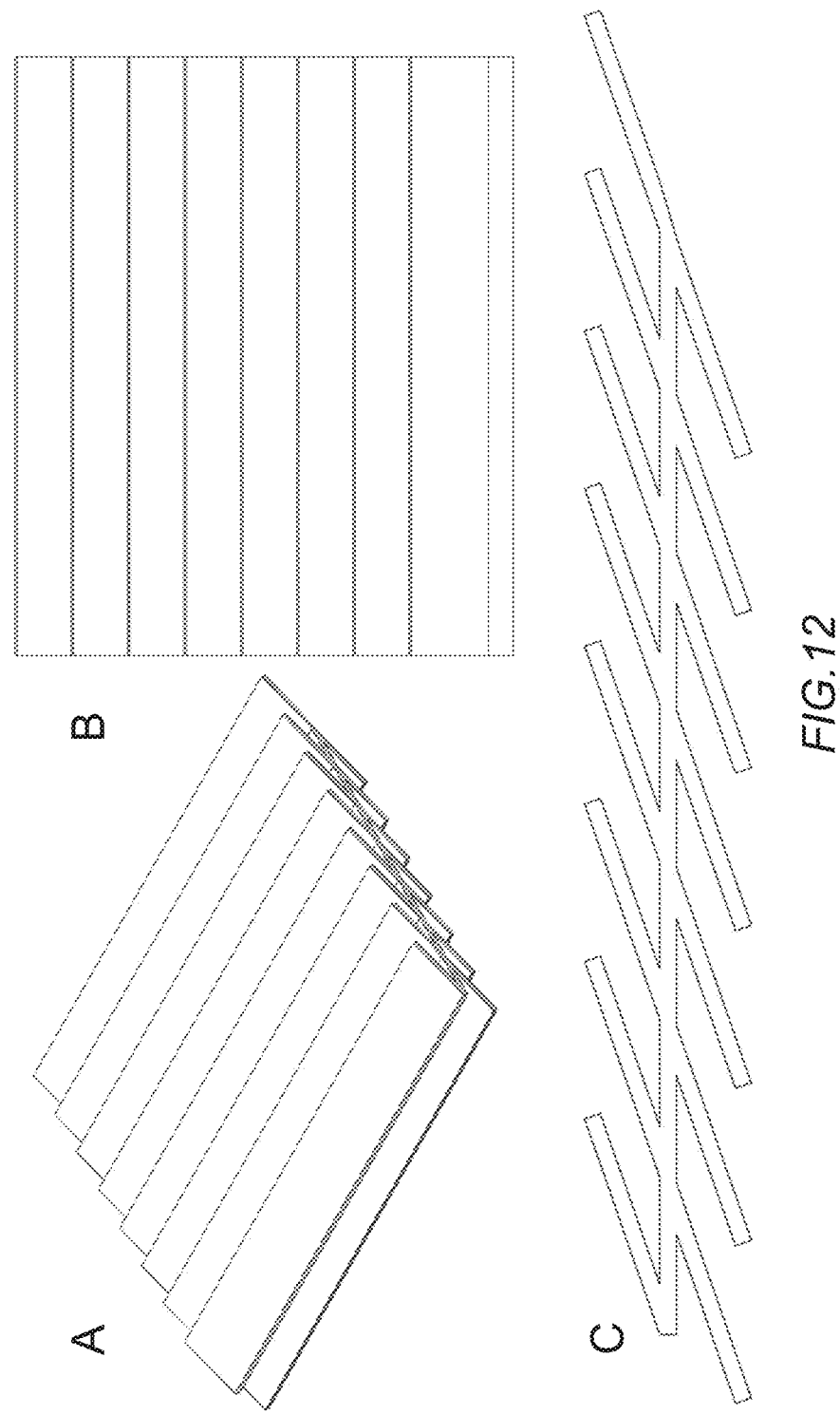
FIGS. 12A-C are perspective views of one embodiment of a 3-dimensional large capacity device assembly ("shutter").
Figure 70:
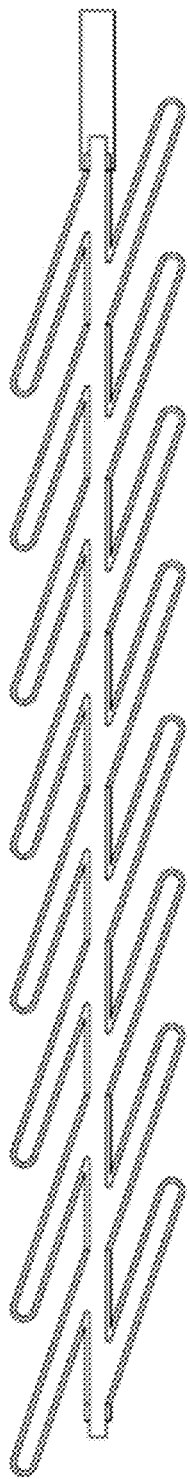
FIG. 70 is a left elevation view of the 3-dimensional large capacity cell encapsulation device or assembly with a single cell chamber and single port, the assembly resembles a plantation shutter design.

In one embodiment, the devices or assemblies can be fabricated to have a total volume in excess of about 20 µL, 50 µL, 100 µL, 150 µL, 200 µL, 250 µL, 300 µL, 350 µL, 400 µL, 450 µL, 500 µL, 550 µL, 600 µL, 6504, 700 µL, 750 µL, 800 µL, 8504, 900 µL, 950 µL, 1000 µL or more. The total cell volume can consist of one device with one cell chamber having the desired cell dose, or can consist of 1 or more devices or assemblies having any number, or a plurality, of cell chambers which together have the desired cell dose. In one embodiment, the device is improved by creating one or more compartments in the cell chamber as described previously in U.S. Pat. No. 8,425,928. FIGS. 3-70 are embodiments of a device or assembly, but the devices or assemblies are not intended to be bound to just that illustrated by FIGS. 3-70. Rather, the device or assembly can include variations based on that described herein and would be considered routine in the art. In some embodiments, the device design can be modified depending on the type of biologically active agents and/or cells encapsulated and to meet the needs and function of the study.

Such devices and/or assemblies can be implanted into a mammal to treat a variety of diseases and disorders. In preferred embodiments, the device comprises a biocompatible, immuno-isolating device that is capable of wholly encapsulating a therapeutically biologically active agent and/or cells therein. For example, such devices can house therapeutically effective quantities of cells within a semipermeable membrane having a pore size such that oxygen and other molecules important to cell survival and function can move through the semi-permeable membrane but the cells of the immune system cannot permeate or traverse through the pores. Similarly, such devices can contain therapeutically effective quantities of a biologically active agent, e.g., an angiogenic factor, a growth factor, a hormone and the like; or a biologically active agent secreted by a cell, e.g. an antibody, a protein, a hormone and the like.

The devices and/or assemblies described herein can be employed for treating pathologies requiring a continuous supply of biologically active substances to the organism.

Such devices, for example, can also be referred to as, bioartificial organs, which contain homogenous or heterogenous mixtures of biologically active agents and/or cells, or cells producing one or more biologically active substances of interest. Ideally, the biologically active agents and/or cells are wholly encapsulated or enclosed in at least one internal space or are encapsulation chambers, which are bounded by at least one or more semi-permeable membranes. Such a semi-permeable membrane should allow the encapsulated biologically active substance of interest to pass (e.g., insulin, glucagon, pancreatic polypeptide and the like), making the active substance available to the target cells outside the device and in the patient's body. In a preferred embodiment, the semi-permeable membrane allows nutrients naturally present in the subject to pass through the membrane to provide essential nutrients to the encapsulated cells. At the same time, such a semi-permeable membrane prohibits or prevents the patient's cells, more particularly to the immune system cells, from passing through and into the device and harming the encapsulated cells in the device. For example, in the case of diabetes, this approach can allow glucose and oxygen to stimulate insulin-producing cells to release insulin as required by the body in real time while preventing immune system cells from recognizing and destroying the implanted cells. In a preferred embodiment, the semi-permeable membrane prohibits the implanted cells from escaping encapsulation.

Preferred devices or assemblies may have certain characteristics which are desirable but are not limited to one or a combination of the following: i) comprises a three-dimensional configuration that allows for delivery of large or high cell doses while at the same time constraining the footprint of the device e.g. space taken up by the device or assembly in the desired anatomical site; ii) comprises folds or bends or angles either in the welds or where the device is sealed or even in the cell chamber, whereby the angle of the folds range from 0 (or 180) to 90 degrees, preferably 0 to 50 degrees, preferably 0 to 40 degrees; iii) comprises a biocompatible material that functions under physiologic conditions, including pH and temperature; examples include, but are not limited to, anisotropic materials, polysulfone (PSF), nano-fiber mats, polyimide, tetrafluoroethylene/polytetrafluoroethylene (PTFE; also known as Teflon®), ePTFE (expanded polytetrafluoroethylene), polyacrylonitrile, polyethersulfone, acrylic resin, cellulose acetate, cellulose nitrate, polyamide, as well as hydroxylpropyl methyl cellulose (HPMC) membranes; iv) releases no toxic compounds harming or compromising the biologically active agent and/or cells encapsulated inside the device; v) promotes secretion or release of a biologically active agent or macromolecule across the device; iv) promotes rapid kinetics of macromolecule diffusion; vi) promotes long-term stability of the encapsulated cells; vii) promotes vascularization; viii) comprised of membranes or a housing structure that is chemically inert; ix) provides stable mechanical properties; x) maintains structure/housing integrity (e.g., prevents unintended leakage of toxic or harmful agents and/or cells); xi) is refillable and/or flushable; xii) is mechanically expandable; xiii) contains no ports or at least one, two, three or more ports; xiv) immune-isolates the transplanted cells from the host tissue; xv) is easy to fabricate and manufacture; xvi) can be sterilized, xvii) can be manufactured in a modular fashion, xviii) is retrievable after implantation, xix) are vented while the cells or the therapeutic agent is being loaded.

The embodiments of the encapsulation devices described herein are in not intended to be limited to certain device size, shape, design, volume capacity, and/or materials used to make the encapsulation devices, so long as one or more of the above elements are achieved.

Encapsulation provides a protective barrier that hinders elements of the host immune system from destroying the cells. This allows the use of unmatched human or even animal tissue, without immunosuppression of the recipient and therefore results in an increase in the diversity of cell types that can be employed in therapy. Additionally, because the implanted cells are retained by a membrane, encapsulation of the cells prevents the inherent risk of tumor formation otherwise present in some cell-based treatments.

The tissue or cells in the core of the device may additionally be immobilized on an immobilizing matrix, such as a hydrogel or extracellular matrix components. In addition, the core of the device may contain an insert to create a "cell free" zone in the center of the core, so as to further reduce the possibility of a necrotic core of cells in the center of the device.

In a preferred embodiment, the devices are immuno-isolatory. An "immuno-isolatory" device, upon implantation into a mammalian host, minimizes the deleterious effects of the host's immune system on the cells within the core of the device. To be immuno-isolatory, the surrounding or peripheral region of the device should (a) confer protection to encapsulated cells from the immune system of the host in whom the device or assembly is implanted, (b) prevent harmful substances of the host's body from entering the core of the device, and (c) provide a physical barrier sufficient to prevent detrimental immunological contact between the isolated cells and the immune system of the host. The thickness of this physical barrier can vary, but it will always be sufficiently thick to prevent direct contact between the cells and/or substances on either side of the barrier. The thickness of this region generally ranges between 5 and 200 microns; a thickness of 10 to 100 microns is preferred, and thickness of 20 to 75 microns is particularly preferred. Types of immunological attack which can be prevented or minimized by the use of the instant vehicle include, but are not limited to, attack by macrophages, neutrophils, cellular immune responses (e.g., natural killer cells and antibody-dependent T cell-mediated cytolysis (ADCC)), and humoral response (e.g., antibody-dependent, complement-mediated cytolysis).

The device can have any configuration appropriate for maintaining biological activity and providing access for delivery of the product or function, including for example, cylindrical, rectangular, disk-shaped, patch-shaped, ovoid, stellate, or spherical. Moreover, the device can be coiled or tubular or wrapped into a mesh-like or nested structure. If the device is to be retrieved at some time after it is implanted, configurations which tend to lead to migration of the devices from the site of implantation (such as spherical devices small enough to travel in the recipient's blood vessels) should be avoided. Preferred embodiments of this invention include shapes that offer high structural integrity and are easy to retrieve from the host. Such shapes include rectangular patches, disks, cylinders, and flat sheets.

In one embodiment, the device or assembly is retrievable after implantation, and preferably the device has a tether that aids in retrieval. Such tethers are well known in the art.

In another embodiment, the device or assembly is sutured at or near the desired anatomical site to prevent it from migrating, moving or traversing inside the patient. Any means for suturing or securing the device or assembly is within the skill of one in the art, e.g. suture tabs can be fabricated into the device or assembly similar to that described in Applicant's U.S. Ser. No. 29/423,365. In one embodiment, the device assemblies are expected to protect allografts from rejection in nonimmunized rodent and human recipients as has been demonstrated by the similar encapsulation devices, e.g. the Theracyte™ device. See Brauker, et al. Neovascularization of synthetic membranes directed by membrane microarchitecture. *J. Biomed. Mater. Res.* 29:1517-1524; 1995; Tibell, et al. Survival of macro-encapsulated allogeneic parathyroid tissue one year after transplantation in nonimmunosuppressed humans. *Cell Transplant.* 10:591-599; 2001; and Kumagai-Braescha, et al., The TheraCyte™ Device Protects against Islet Allograft Rejection in Immunized Hosts, *Cell Transplant.* 2012 Oct. 3. Similarly, xenogeneic grafts are not protected by the Theracyte™ device, instead leaking xenoantigens cause a strong inflammatory reaction around the implant. See Brauker, et al. Local inflammatory response around diffusion chambers containing xenografts. Nonspecific destruction of tissues and decreased local vascularization. *Transplantation* 61:1671-1677; 1996; Loudovaris, et al. Destruction of xenografts but not allografts within cell impermeable membranes. *Transplant. Proc.* 24:2291-2292; Loudovaris, et al., CD4+ T cell mediated destruction of xenografts within cell-impermeable membranes in the absence of CD8+ T cells and B cells. *Transplantation* 61:1678-1684; 1996; and McKenzie, et al. Protection of xenografts by a combination of immunoisolation and a single dose of anti-CD4 antibody. *Cell Transplant.* 10:183-193; 2001.

In other embodiments, the device assemblies consist of one or two or more seals that further partition the lumen of the device, i.e., a partition seal. See, e.g. Applicant's U.S. Design applications 29/408366, 29/408368, 29/408370 and 29/423,365. Such designs prohibit, reduce, or do not promote large cell aggregates or clusters or agglomerations such that cells packed in the center of the large clusters/agglomerations are denied, or receive less, nutrients and oxygen and therefore potentially do not survive. Devices containing a plurality of chambers or compartments therefore are better capable to disperse the cells throughout the chamber/compartment or chambers/compartments. In this way, there is more opportunity for each cell to receive nutrients and oxygen, thereby promoting cell survival and not cell death.

In one embodiment relates to a device or assembly consisting of substantially elliptical to rectangular shape cell chambers. These devices are further compartmentalized or reconfigured so that there is a weld or seam running through the center of the device, either sealing off each half of the device, thus forming two separate reservoirs, lumens, chambers, void spaces, containers or compartments; or the weld or seam creates an accordian-shaped hamber which is separated or divided in the middle due to the weld but such a weld in this instance does not completely seal off the chambers.

Another embodiment relates to a similar device or assembly consisting of substantially elliptical or rectangular shape cell chambers having 2, 3, 4, 5, 6, 7, 8, 9, 10 or more welds across the plane of the device (e.g. see U.S. Pat. No. 8,425,928). In some aspects the welds are across the horizontal aspect or plane of the device. In other aspects the welds are across the vertical aspect or plane of the device. In still other aspects, intersecting welds are present across both the horizontal and vertical aspects of the plane. In some aspects the welds are parallel and equidistant to each other. In other aspects the welds are perpendicular. In still other aspects the welds are parallel but not equidistant. As in the above example, such a design can effectively form up to 2, 3, 4, 5, 6, 7, 8, 9, 10 or more chambers, wholly separated if the weld runs traverses and connects both boundaries of the device, or it can create one continuous chamber but inter-digitated forming discrete regions within the same chamber. Further, although certain exemplary devices are described with welds being parallel or parallel and equidistant, still other devices can be customized or made with welds in any direction or orientation, including long welds which have regions interrupted by no welds. The type and number of welds used can depend on the cell population or agent employed and for what treatment or purpose. In some embodiments, welds can be arranged to modify the look of the device.

FIGS. 3-14 show embodiments of 3-dimensional cell encapsulation devices or assemblies, but as described above, these are just illustrated embodiments and one of ordinary skill in the art can envisage that by forming different configurations using welds or seams in any such device, or modify the shape, or add other features previously described by Applicant to customize the device or assembly suitable for the purpose intended. For example, the device can be ultrasonically welded around the entire perimeter to create a completely enclosed internal lumen or forming a plurality of lumens. Other means of sealing or walling off membranes to form the pouch like device can be used. The lumen is further compartmentalized by an internal weld that is centrally located and extends down the long axis of the device. This weld extends to a point that effectively limits the thickness or depth of each compartment yet does not completely segregate the internal lumen. By this approach, the width and depth of the compartments are controlled and can be varied as is required to enable cell product survival and performance. Moreover, all dimensions of the device, which include but are not limited to, the overall length, overall width, perimeter weld thickness, perimeter weld width, compartment length, compartment width, compartment depth, internal weld length, internal weld width and port position are design specifications that can be modified to optimize the device for unique cell products and/or biologically active agents.

FIGS. 3-70, for example, the compartment is loaded with a cell product or biologically active agent through two individual ports that are incorporated into the device during ultrasonic welding of the perimeter. These ports extend into the lumen or compartments and allow access to the compartment for the purpose of evenly distributing cells and/or agents during loading. In certain embodiments, the ports help vent the cell chamber while the cells or the therapeutic agent is being loaded in another port, thus preventing the accumulation of pressure in the device.

Alternatively, in another embodiment, the devices or assemblies provided herein contain no ports of entry or exit, i.e. the devices are said to be port-less. In another aspect, the outer perimeter and the compartmentalization spot welds are first created by ultrasonic welding. The spot welds function similarly to the internal weld and can be placed in a manner across the device to periodically limit the expansion of the lumen or compartment at any given point. Again, the lumen or compartments created by spot welding, therefore interconnecting the compartments, and not isolating or wholly separating any one lumen or compartment. This approach can be accomplished for one cell chamber in one device or for a plurality of cell chambers in a device or assembly, or any one cell chambers in a device or assembly. Moreover, the total number, diameter and distribution of the spot welds are design parameters that can be optimized to accommodate the loading dynamics and growth rates of any cell product or agent.

Once cells are loaded into the device, the outer perimeter is completely and aseptically sealed by a second ultrasonic weld across the edge of the device. The result of the multi-step sealing process is that finished devices are totally enclosed and have no ports extending from the perimeter. This approach simplifies the loading process and improves the overall integrity and safety of the device, as the ports can be an area of the perimeter where breaches can occur as a result of suboptimal ultrasonic welding.

Further, although the above process was described in 2 sequential steps, the means for encapsulating the cells and/or agents is not limited to the described 2 steps but to any number of steps, in any order, necessary to encapsulate the cells and at the same time prevent or reduce the level of breach of the device.

One of ordinary skill in the art cam accomplish this in various ways, e.g., by using an ultrasonic sonotrode that has an internal sharpened edge, which can cut the material immediately after welding. These cut-out welds have an advantage in that they are more readily integrated with the host tissue because the cut-out welds promote vascularization of the device, thus improving the survival and performance of oxygen-dependent cell products and/or agents. As a consequence of facilitating and promoting new vasculature through the device, there is improved diffusive transport of oxygen in the X-Y direction, which is normally limited towards the center of planar sheet devices.

In other embodiments, the device design can be different shapes, e.g. the cell encapsulation device can be in the shape of a tube or flattened tube or any other such shape which satisfies one of the above requirements for a device of the invention.

Device Materials

Useful biocompatible polymer devices comprise (a) a core which contains tissue or cells, and (b) a surrounding or peripheral region of biocompatible, semi-permeable membrane (jacket) which does not contain isolated cells (i.e., the membrane itself not immobilizing cells).

The "semi-permeable" nature of the device membrane permits molecules produced by the cells (metabolites, nutrients and therapeutic substances) to diffuse from the device into the surrounding host tissue, but is sufficiently impermeable to protect the cells in the core from detrimental immunological attack by the host.

Cell permeable and impermeable membranes comprising of have been described in the art including those patents previously described above by Baxter including, U.S. Pat. Nos. 6,773,458; 6,520,997; 6,156,305; 6,060,640; 5,964,804; 5,964,261; 5,882,354; 5,807,406; 5,800,529; 5,782,912; 5,741,330; 5,733,336; 5,713,888; 5,653,756; 5,593,440; 5,569,462; 5,549,675; 5,545,223; 5,453,278; 5,421,923; 5,344,454; 5,314,471; 5,324,518; 5,219,361; 5,100,392; and 5,011,494.

Various polymers and polymer blends can be used to manufacture the device jacket, including, but not limited to, polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), PTFE, as well as derivatives, copolymers and mixtures of the foregoing.

Biocompatible semi-permeable hollow fiber membranes, and methods of making them are disclosed in U.S. Pat. Nos. 5,284,761 and 5,158,881 (see also, WO 95/05452), each incorporated herein by reference. In one embodiment, the device jacket is formed from a polyether sulfone hollow fiber, such as those described in U.S. Pat. Nos. 4,976,859 and 4,968,733, each incorporated herein by reference.

In one embodiment, the encapsulating devices are comprised of a biocompatible material including, but are not limited to, anisotropic materials, polysulfone (PSF), nano-fiber mats, polyimide, tetrafluoroethylene/polytetrafluoroethylene (PTFE; also known as Teflon®), ePTFE (expanded polytetrafluoroethylene), polyacrylonitrile, polyethersulfone, acrylic resin, cellulose acetate, cellulose nitrate, polyamide, as well as hydroxylpropyl methyl cellulose (HPMC) membranes. These and substantially similar membrane types and components are manufactured by at least Gore®, Phillips Scientific®, Zeus®, Pall® and Dewal® to name a few.

Device Loading

One embodiment for loading therapeutic agents including cells into the implantable device or device is described in Applicant's publication WO/2012/115619 (PCT/US11/25628), LOADING SYSTEM FOR AN ENCAPSULATION DEVICE, filed Feb. 21, 2011, which is incorporated herein in its entirety.

In another embodiment, the above device cell loading is fully automated such that from the period the PEC are thawed and cultured until they cell aggregates are counted and loaded into the device, they are contained in closed and sterile environment.

In another embodiment, the cell aggregates are loaded into the devices using a syringe-like system.

These and other similar methods will be apparent to one skilled in the art.

Cell Density

Cell loading density may be varied over a wide range. The number of cells loaded into any device will depend on the dosage contemplated or dosage mandated by the treatment and the number of macro-encapsulation devices employed in the treatment.

In one embodiment, between $10 \times 10^3$ to $10 \times 10^9$ cells are loaded into each chamber (compartment or lumen) of a device or assembly. In one aspect of the invention, Applicant's methods for producing PEC result in about 3 to 4 million cells per 10 μL of a cell aggregate suspension, or a theoretical volume of about 367,000 cells per microliter. In one aspect of the invention, for an EN250 device, a device capable of holding about 250 μL of a cell aggregate suspension, the total number of cell is about 91-92 million cells. In another aspect, multiple cell chamber devices each with the capacity to hold about 100 μL of a cell aggregate suspension (e.g. FIGS. 3-70), are loaded with cells. For example, an assembly containing eight 100 μL cell chambers (or about 3-4 million cells per chamber), or about 240 to 320 million cells. Cell chambers can be any size, for example, in FIG. 5 the cell chambers of the 3-dimensional device are about 121 μL (based on 200 μm lumen). Hence, a device or assembly having 8 cell chambers having a capacity of about 121 μL each is about 968 μL, and having a total cell capacity of about 36 to 44 million cells per chamber (121 μL at 367,000 cells per 1 μL=44.4 million cells per chamber; and if there are 8 cell chambers, a total of about 354.9 million cells per assembly as described herein.

The above describes the theoretical cell dose or numbers based on maximal volume capacity of a single device or an individual cell chamber within a larger device; the actual dosage may depend on the types of cells and/or the medium in which the cells are in for loading purposes. The actual cell dose may also depend on whether the cell culture is homogenous pure culture of therapeutic cells or a population consisting of different populations of cells, such that the real cell dose for any therapeutic cell is a percentage of the total number of cells loaded or seeded into the device or cell chamber. Similarly, for macro cell-encapsulation delivery, it is preferable to implant as few devices or as few cell chambers in any device as possible, preferably no more than ten, preferably no more than 9, preferably no more than 8 cell chambers in a device, no more than 7 cell chambers in a device, no more than 6 cell chambers in a device, no more than 5 cell chambers in a device, no more than 4 cell chambers in a device, no more than 3 cell chambers in a device, no more than 2 cell chambers in a device and no more than 1 cell chamber per device, if possible. Any number of cell chambers required will be dependent on the luminal capacity of the chamber.

Multi-Chamber Modular Devices

In one embodiment devices or assemblies are provided containing a plurality or multiplicity of cell chambers interconnected by cell-free zones, e.g. folds and bends. For example, one embodiment comprises multiple porous cell chambers that are laterally connected to each other (see FIGS. 3-70). In one such embodiment, the multiple porous cell chambers are formed, for example, by ultrasonically welding the top and bottom surfaces of a porous material along a line substantially parallel to a longitudinal axis of the device and houses any of 2, 3, 4, 5, 6, 7, 8, 9, 10, 11, 12, 13, 14, 15, 16, 17, 18 or more cell chambers. Each cell chamber has a fixed volume capacity, e.g. 100 μL, with one or more ports and an internal matrix scaffold or foam, and, if desirable an internal weld or welds to periodically limit the expansion of the lumen or compartment. In one aspect, the cell encapsulation device described herein comprises at least 2 porous chambers or sufficient chambers to house an adequate human dosage of islets derived from pluripotent stem cells to treat and ameliorate a subject with diabetes once implanted. In a preferred embodiment, each chamber has a substantially same inner diameter and can hold about the same number of cells. The availability of multiple chambers allows the use of any number or combination of chambers depending on the volume of cellular preparation required, the disease treatment regimen prescribed, which is within the knowledge and skill of persons skilled in the art to determine.

In one embodiment of the invention, adjacent cell chambers in a multiple chamber device or assembly may take on different designs, volume capacity, cross-sectional dimensions and surface areas. In one aspect, multiple porous cell chambers are formed by ultrasonically welding the polymer mesh from a proximal end to a distal end creating cell-free zones at each weld. The top and bottom surfaces of cell chambers are continuous across the one or more cell chambers except where they are interrupted by ultrasonic weld lines or other forms of creating cell-free zones. The core or center of each cell chamber may contain a seal or a weld in the cell chamber interior to create a "cell free" zone in the center of the chamber, for the purpose of partitioning the chamber and reducing the possibility of a necrotic core of cells in the center of the device; which can occur when the diameter of the cell chambers becomes too big or too wide. Such cell-free zones or welds are also described in Applicant's U.S. Pat. No. 8,278,106, specifically FIGS. 2-7 and Applicant's device Design applications previously mentioned. These cell-free zones or welds can be bent or folded at an angle e.g. at 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, and 180 degrees, which provides a configuration to increase cell volume by adding more cell chambers to the device assembly while at the same time constrains or even at times reduces or decreases the footprint of the entire multiple chamber device assembly.

In a preferred embodiment of the invention, the devices are laterally connected to each other and separated by cell-free zones and/or welds. See FIGS. 13-14, for example. In one such embodiment, the multiple porous cell chambers are formed by ultrasonically welding the top and bottom surfaces of a porous material along a line substantially parallel to a longitudinal axis of the device and houses at least 2, 3, 4, 5, 6, 7, 8, 9, 10, 11, 12, 13, 14, 15, 16 or more cell chambers. Each chamber can house one or more ports on the same side or on opposing sides. Further each chamber can have an internal matrix scaffold and/or contain an internal weld.

Alternatively, individual cell chambers in any device or assembly need not have the same configuration or design. Each chamber can take on different characteristic designs including but not limited to cell chambers can contain an elastomeric foam, cell chambers with interior weld partitions as described previously in Applicant's U.S. Pat. No. 8,278,106, cell chambers with different outer mesh layers, cell chambers with different porous membranes, cell chambers with additional porous membranes (e.g. vascularizing membrane, or membrane that elutes certain factors to promote vascularization), cell chambers of different size to customize the cell dosage and the like. Multiple cell chamber devices or assemblies are important for the purpose of delivering high therapeutic effective doses to a patient while at the same time providing flexibility in the dosing scheme and not increasing the footprint of the device.

Device Manufacturing

In one non-limiting embodiment, there is provided a manufacturing process for making one or more of the devices or assemblies with one or more cell chamber consisting of various components including but not limited to an outer mesh, the cell-impermeable but porous layer, the adhesive layer or film and any other component necessary for the device (e.g. the port). Methods of manufacture can include but are not limited to stamping, welding, casting, molding, extruding, die forming and/or die cutting, and/or cutting (e.g., laser cut, water jet cut, machine tool cut, etc.) each of the layered components of the cell chamber. One or more of the layers can be aligned and stamped or cut together, e.g. by a laser.

In another non-limiting manufacturing process, one or more layers of the device can be formed by generating a mechanically drawn and/or computer image of the device or one or more portions of the device. One common commercial software package is AutoCAD, but other drawing engineer software packages are available and can be used. These layers are adhered together by techniques common in the art including but not limited to thermal caulking, welding (including high frequency or ultrasonic), gluing, taping, pressure heat fusing and adhesion by means of conventional pharmaceutically acceptable adhesives, film and the like. In a preferred embodiment, ultrasonic welding is used to join the different flexible sheets of the cell chamber or device together because of its speed, cleanliness (no solvents) and production of a thin and narrow seam and strength.

Device Closure or Sealing

In one embodiment, the device assemblies consists of at least one, preferably at least two cell chambers that are formed from welding to seal or fully enclose the cells in the cell chamber. A number of techniques are used for welding plastics and any of them is contemplated in this invention as a means to seal the cell chambers devices or assemblies. For example, although the devices herein use high frequency ultrasonic welding, adhesive and clamps, other plastic welding methods are contemplated including but not limited to hot gas welding or hot air welding using a heat gun or produces a jet of hot air that softens both the parts to be joined and a plastic filler rod; hot air/gas welding; heat seal including but not limited to hot bar sealer, impulse sealer; freehand welding whereby the hot air (or inert gas) is on the weld area and the tip of the weld rod at the same time; speed tip welding; extrusion welding, particularly, for joining materials over 6 mm thick; contact welding; hot plate welding; radio frequency welding; injection welding; ultrasonic welding friction welding; spin welding; laser welding; transparent laser plastic welding; and solvent welding. These and other methods for welding plastics are well known in the art and one skilled in the art is able to employ any means to suit the needs of adhering or adjoining materials.

In another embodiment, any suitable method of sealing the cell chambers may be used. Preferred methods of sealing include the employment of polymer adhesives, crimping, knotting and heat sealing. These sealing techniques are known in the art. In other preferred embodiments, any suitable "dry" sealing method is used, as described in U.S. Pat. No. 5,738,673. In such methods, a substantially nonporous fitting is provided through which the cell-containing solution is introduced. Subsequent to filling, the device is sealed. Methods of sealing the devices are known in the art.

In another embodiment, there is provided a method of closing a cell chamber or device that comprises wetting at least a portion of a permeable polymeric membrane of the device with a liquid and applying heat to at least a portion of a wetted thermoplastic polymer in association with the membrane to create a closure. Such a closure is referred to herein as a "wet seal." In this "wet sealing" process, the thermoplastic polymer melts at a lower temperature than the polymeric membrane. Once melted, the thermoplastic polymer integrates with the polymeric membrane and flows along surfaces and into available interstices of the membrane. Through passageways become filled with the melted polymer, thereby blocking fluid communication in the polymeric membrane in the region of the closure. When the thermoplastic polymer cools below its melt temperature, a closure is formed in the device. The closure is cell-tight and often liquid-tight. The portion of the device having a closure formed with a wet seal delineates a cell-impermeable region of the device.

One embodiment provided a method of closing a containment device that comprises wetting a porous expanded polytetrafluoroethylene (ePTFE) membrane of the containment device with a liquid, and applying heat to a portion of the membrane in communication with a thermoplastic polymer, such as fluorinated ethylene propylene (FEP), to create a closure. The closure is formed by melting and fusing of the polymer to itself and the membrane in the presence of the liquid.

In one embodiment there is a provided a method of closing a cell chamber or device that comprises applying sufficient heat to a portion of a permeable membrane in association with a thermoplastic polymer to melt and flow the thermoplastic polymer, followed by twisting the membrane/thermoplastic polymer combination in the region of the heating to form a closure. The membrane/thermoplastic polymer combination is also elongated while heating or twisting the materials. After heating, twisting, and elongation a separation region is formed and the membrane is cut in the separation region.

These and other "wet seal" methods of sealing are described in detail in U.S. Pat. No. 6,617,151.

Immobilized Devices

In one embodiment, there is provided is an implantable device, which is immobilized at an implantation site to maintain the encapsulated cell and/or biological active agent at the implantation site and permit diffusion of, for example, an expressed and secreted therapeutic polypeptide from the implantation site. Such means of immobilizing the device at the implantation can be suture tabs on the device as described above or other means of affixing or gluing the device to the anatomical site is envisioned. In one aspect, the implantation site is at, or close in proximity to, the tissue or organ which is focus of the treatment. In other aspects, where delivery of the secreted agent from the device is not location dependent and biodistribution of the agent is dependent on the vasculature, the device can be implanted in a remote location or in close proximity to a large blood vessel or capillary bed. For example, in a preferred embodiment, the biocompatible device is implanted subcutaneously under the skin on the forearm, or flank, or back, or buttocks, or leg and the like, where it substantially remains until such time as it is required for it to be removed or explanted.

Expandable Devices

Conventional implantable devices are commonly made of rigid, non-expandable biocompatible materials. In one embodiment, there is provided devices or assemblies are expandable. Whether the device is capable of expanding may be an inherent part of the materials employed to make the device, e.g., a polymer sheath which is expandable, or can be designed such that they are expandable or have expandable capabilities. For example, a device which expands in size to house additional cells or to refill an existing device is provided.

In one embodiment the large capacity device or assembly is contained in a larger housing or holder or cage, which is slightly more rigid, and non-expandable but allowing for one or more small or large cell-encapsulation devices to be contained therein. The holder is analogous to a cassette holder capable of holding one or more cassettes. Alternatively, the holder contains a plurality of devices only some of which are loaded with cells or have cells encapsulated therein, while others are empty and can be loaded and filled with cells or agents at a later period in time or any time subsequent the initial implantation. Such an implantable housing is comprised of inert materials suitable for implantation in the body, e. g., metal, titanium, titanium alloy or a stainless steel alloy, plastic, and ceramic appropriate for implantation in the mammal, more specifically, the human body.

Refillable Cell Encapsulation Devices

In one embodiment, provided herein relates to an encapsulation device with a refillable reservoir, lumen, container or compartment, which can be periodically filled or flushed with appropriate therapeutic or biologically active agents and/or cells. Such filling may be accomplished by injecting a therapeutically effective amount of the appropriate therapeutic or biologically active agents and/or cells into an implanted reservoir, lumen, container or compartment, e.g., subdermally or subcutaneously using a syringe or other standard means in the art for filling like reservoirs, lumens, containers or compartments in vivo.

Encapsulated Cells

In one embodiment, cells encapsulated in the 3-dimensional large capacity device assemblies include but are not limited to mesendoderm, definitive endoderm lineage type cells including but not limited to PDX-1 negative foregut, PDX-1 positive foregut, pancreatic endoderm (PE or PEC), pancreatic progenitors, endocrine precursors or progenitors, endocrine cells such as immature beta cells and the like. In general, definitive endoderm lineage cells may also include any cells derived from definitive endoderm and their derivatives and progeny including but not limited to the organs which derive from the gut tube such as the lungs, liver, thymus, parathyroid and thyroid glands, gall bladder and pancreas. See Grapin-Botton and Melton, 2000; Kimelman and Griffin, 2000; Tremblay et al., 2000; Wells and Melton, 1999; Wells and Melton, 2000. These and other definitive endoderm-lineage type cells have been described in detail by Applicant, at least in Other suitable embodiments described herein are further described in detail in at least U.S. Pat. No. 7,958,585, PREPRIMITIVE STREAK AND MESENDODERM CELLS; U.S. Pat. Nos. 7,510,876, 8,216,836, 8,623,645 DEFINITIVE ENDODERM; U.S. Pat. No. 8,129,182, ENDOCRINE PRECURSOR CELLS, PANCREATIC HORMONEEXPRESSING CELLS AND METHODS OF PRODUCTION; U.S. Pat. No. 8,278,106, ENCAPSULATION OF PANCREATIC CELLS DERIVED FROM HUMAN PLURIPOTENT STEM CELLS; and U.S. application Ser. No. 14/106,330, IN VITRO DIFFERENTIATION OF PLURIPOTENT STEM CELLS TO PANCREATIC ENDODERM CELLS (PEC) AND ENDOCRINE CELLS, filed Dec. 13, 2013.

The invention also contemplates differentiable cells from any source within an animal, provided the cells are differentiable as defined herein. For example, differentiable cells may be harvested from embryos, or any primordial germ layer therein, from placental or chorion tissue, or from more mature tissue such as adult stem cells including, but not limited to adipose, bone marrow, nervous tissue, mammary tissue, liver tissue, pancreas, epithelial, respiratory, gonadal and muscle tissue. In specific embodiments, the differentiable cells are embryonic stem cells. In other specific embodiments, the differentiable cells are adult stem cells. In still other specific embodiments, the stem cells are placental- or chorionic-derived stem cells.

Of course, the invention contemplates using differentiable cells from any animal capable of generating differentiable cells. The animals from which the differentiable cells are harvested may be vertebrate or invertebrate, mammalian or non-mammalian, human or non-human. Examples of animal sources include, but are not limited to, primates, rodents, canines, felines, equines, bovines and porcines.

The differentiable cells can be derived using any method known to those of skill in the art. For example, human pluripotent cells can be produced using de-differentiation and nuclear transfer methods. Additionally, the human ICM/epiblast cell or the primitive ectoderm cell used herein can be derived in vivo or in vitro. Primitive ectodermal cells may be generated in adherent culture or as cell aggregates in suspension culture, as described in WO 99/53021. Furthermore, the human pluripotent cells can be passaged using any method known to those of skill in the art, including, manual passaging methods, and bulk passaging methods such as enzymatic or non-enzymatic passaging.

Embodiments of the compositions and methods described herein contemplate the use of various differentiable primate pluripotent stem cells including human pluripotent stem cells such as hESC, including but not limited to, CyT49, CyT212, CyT203, CyT25, (commercially available at least at the time of filing of this instant application from ViaCyte Inc. located at 3550 General Atpmics Court, San Diego Calif. 92121) BGO1, BG02 and MEL1, and induced pluripotent stem (iPS) cells such as iPSC-482c7 and iPSC-603 (Cellular Dynamics International, Inc., Madison, Wis.) and iPSC-G4 (hereinafter "G4") and iPSC-B7 (hereinafter, "B7") (Shinya Yamanaka, Center for iPS Cell Research, Kyoto University); studies using G4 and B7 are described in detail herein. Certain of these human pluripotent stem cells are registered with national registries such as the National Institutes of Health (NIH) and listed in the NIH Human Stem Cell Registry (e.g., CyT49 Registration No. #0041). Information on CyT49, other available cell lines can also be found on the worldwide web at stemcells.nih.gov/research/registry. Still other cell lines, e.g., BG01 and BG01v, are sold and distributed to third parties by WiCell®, an affiliate of the Wisconsin International Stem Cell (WISC) Bank (Catalog name, BG01) and ATCC (Catalog No. SCRC-2002), respectively. While other cell lines described herein may not be registered or distributed by a biological repository, such as WiCell® or ATCC, such cell lines are available to the public directly or indirectly from the principle investigators, laboratories and/or institutions. Public requests for cell lines and reagents, for example, are customary for those skilled in the art in the life sciences. Typically, transfer of these cells or materials is by way of a standard material transfer agreement between the proprietor of the cell line or material and the recipient. These types of material transfers occur frequently in a research environment, particularly in the life sciences.

In August 2006, Klimanskaya et al. demonstrated that hESC can be derived from single blastomeres, hence keeping the embryo intact and not causing their destruction. Biopsies were performed from each embryo using micromanipulation techniques and nineteen (19) ES-cell-like outgrowths and two (2) stable hESC lines were obtained. These hESC lines were able to be maintained in an undifferentiated state for over six (6) months, and showed normal karyotype and expression of markers of pluripotency, including Oct-4, SSEA-3, SSEA-4, TRA-1-60, TRA-1-81, Nanog and Alkaline Phosphatase. These hESC can differentiate and form derivatives of all three (3) embryonic germ layers both in vitro and form in teratomas in vivo. These methods to create new stem cell lines without destruction of embryos addresses the ethical concerns of using human embryos. See Klimanskaya et al. (2006) *Nature* 444:481-5, Epub 2006 Aug. 23. However, Klimanskaya et al. co-cultured the derived hESC line with other hESC. Later, in 2008, Chung Y. et al., were able to obtain hES cell lines again from a single blastomere but without co-culture with hESC. See Chung Y. et al., *Cell Stem Cell* 2008, 2(2), 113-117. Thus, production of cells for encapsulation as provided herein can be practiced without destruction or commercialization of a human embryo.

Databases exist describe and provide information on various pluripotent stem cell lines and are periodically updated. These databases include but are not limited to the National Institutes of Health (NIH) Human Stem Cell Registry, the Human Embryonic Stem Cell Registry and the International Stem Cell Registry located at the University of Massachusetts Medical School, Worcester, Mass., USA.

Methods for Increasing Cell Viability

One obstacle to the field of cell and tissue encapsulation/immuno-isolation has been the lack of sufficient oxygen and nutrient transport across the polymer membranes used to encapsulate cells and tissues. The result of this insufficient gas and nutrient exchange is lowered metabolic activity and cell death. Embodiments described herein relate to an implantable cell encapsulation device addressing this drawback of the prior art.

Oxygen partial pressures have been measured within islets, in their native environment, after isolation, and post-transplant in various polymer devices as well as naked or free, for example, under the kidney capsule. Oxygen partial pressures in pancreatic islets are the highest of any organ in the body (37-46 mmHg). However, upon isolation, these values fall drastically (14-19 mm Hg). Upon transplantation of pancreatic islets into normo-glycemic animals the values decrease slightly (9-15 mmHg) as compare to their isolated values. See Dionne et al., Trans. Am. Soc. Artf. Intern. Organs. 1989; 35: 739-741; and Carlsson et al., Diabetes July 1998 47(7):1027-32. These studies demonstrate that when tissues are immuno-isolated and transplanted, even in a vascularized region such as the kidney capsule, the oxygen partial pressures drop as compared to their native states (37-46 mmHg). Hence, these nearly anoxic conditions can result in cell death, particularly the nearer the cell to the core of a cell cluster or core of an encapsulating device.

In order to achieve better oxygen availability and delivery to the encapsulated cells or tissues and/or biologically active agents, embodiments described herein relate to the use of, for example, perfluorinated substances in the device design and/or formulation, e.g., in the membranes or materials employed for assembly of the device. In particular, perfluoro organic compounds, e.g., perfluorocarbons (PFCs), are good solvents because they have several fold higher solubility for oxygen than water. For example, under normal conditions, liquid PFCs dissolve between 40 and 55% by volume of oxygen and between 100 and 150% by volume of CO2. PFCs are largely used as blood substitutes and tissue preservation. Additionally, PFC derivatives are dense, chemically inert, and water insoluble compounds that cannot be metabolized.

In one embodiment enhanced $O_2$ delivery is performed by a PFC-emulsion or mixture of PFC with some matrix. The device components or cells for example could be suspended or soaked or incubated in the emulsion/matrix to form a coating. Still certain PFC emulsions with higher weight/volume concentrations have been known to have improved oxygen delivery and retention properties. And because of the higher oxygen partial pressure created by the $O_2$ carrying capabilities of PFCs, an $O_2$ pressure gradient is created that drives diffusion of dissolved oxygen into the tissue, thereby enhancing $O_2$ delivery to the cells.

The PFC substance includes but is not limited to perfluorotributylamine (FC-43), perfluorodecalin, perfluorooctyl bromide, bis-perfluorobutyl-ethene, or other suitable PFCs. Preferred PFCs typically contain about 60 to about 76 weight percent carbon-bonded fluorine. The perfluorinated fluids can be single compounds, but usually will be a mixture of such compounds. U.S. Pat. No. 2,500,388 (Simons); U.S. Pat. No. 2,519,983 (Simons); U.S. Pat. No. 2,594,272 (Kauck et al.); U.S. Pat. No. 2,616,927 (Kauck et al.); and U.S. Pat. No. 4,788,339 (Moore et al.). PFCs useful in the embodiments described herein also include those described in Encyclopedia of Chemical Technology, Kirk-Othmer, Third Ed., Vol. 10, pages 874-81, John Wiley & Sons (1980). For example, useful PFCs include perfluoro-4-methylmorpholine, perfluorotriethylamine, perfluoro-2-ethyltetrahydrofuran, perfluoro-2-butyltetrahydrofuran, perfluoropentane, perfluoro-2-methylpentane, perfluorohexane, perfluoro-4-isopropylmorpholine, perfluorodibutyl ether, perfluoroheptane, perfluorooctane, and mixtures thereof. Preferred inert fluorochemical liquids include perfluorohexane, perfluoro-2-butyltetrahydrofuran, perfluoroheptane, perfluorooctane, and mixtures thereof. Commercially available PFCs useful in the embodiments described herein include FLUORINERT fluids, e.g., FC-72, FC-75, FC-77 and FC-84, described in the 1990 product bulletin #98-0211-5347-7(101.5) NPI, FLUORINERT fluids, (available from Minnesota Mining and Manufacturing Company, St. Paul, Minn.), and mixtures thereof.

Lumenal Matrix, Foam or Scaffold

In one embodiment of the invention, strategies are used to increase oxygen supply and solubility throughout the encapsulation chamber, in particular, increased oxygen solubility in proximity to the inner parts of the cell chamber.

In one embodiment, a method or means for increasing oxygen to the cell chamber core consists of providing a luminal or chamber matrix, foam or scaffold or insert between the walls of the cell encapsulating device forming the cell chamber. Such matrix substantially consists of interconnected cavities or pores of a size that permits cells or cell clusters or cell aggregates to reside in the open spaces or in the pores and also are conduits, pipes or channels for transporting oxygen and other nutrients to the cells throughout the foam matrix. The pore size, pore density and void volume of the foam scaffold may vary. The pore shape may be circular, elliptical or irregular capable of holding single cells, cell clusters or aggregates. Because the pore shape can vary considerably, its dimensions may vary according to the axis being measured. For the purposes of this invention, at least some pores in the foam should have a pore diameter of between 40 to less than 1000 µm, preferably between 50 to 500 µm, preferably between 50 to 400 µm, preferably between 50 to 300 µm, preferably between 50 to 200 µm, and preferably between 50 to 100 µm. In one embodiment, foam pores are circular and/or non-circular, and if non-circular (e.g., elliptical) the pore may have variable dimensions, so long as its size is sufficient to permit a cell to reside in the cavity or surfaces within the pore. In addition to the foregoing cell permissive pores sizes, preferably at least a fraction of the cavities and pores in the foam should be less than 10 µm to be cell impermissive but still provide channels for transport of nutrients and biologically active molecules throughout the foam, including oxygen.

Pore density of the foam (i.e., the number per volume of pores that can accommodate cells, as described above) can vary between 20-90%, preferably between 50-70%.

In one embodiment, the luminal matrix or foam is an elastomer matrix. Various elastomeric polymers have been described, for example, WO2010/121024 to Stabler et al. describes a composite for delivering oxygen including a biocompatible polymeric support including but not limited to silicones, polyolefins, polyesters, polystyrene, co-polymers thereof, and mixtures thereof. The polymeric support can further include a siloxysilane-containing polymer including but not limited to vinyl-, alkyl-, or alkylarylsiloxysilane formed from polymer precursors including monomers, oligomers and polymers including but not limited to polydimethylsiloxane (PDMS), polydimethylsiloxane monoacrylate, polydimethylsiloxane monomethacrylate, and mixtures thereof.

The term "silicone elastomer" or "silicone composition" or "silicone matrix" as used herein is a broad term, and is to be given its ordinary and customary meaning to a person of ordinary skill in the art (and is not to be limited to a special or customized meaning), and refers without limitation to a composition of matter that comprises polymers having at least silicon and oxygen atoms in the backbone.

In another embodiment, other non-bioabsorbable materials may include polymers such as polyethylene, polyvinylacetate, polymethylmethacrylate, silicone, polyethylene oxide, polyethylene glycol, polyurethanes, polyvinyl alcohol, natural biopolymers (e.g., cellulose particles, chitin, keratin, silk, and collagen particles), and fluorinated polymers and copolymers (e.g., polyvinylidene fluoride, polytetrafluoroethylene, and hexafluoropropylene).

In another embodiment, PDMS can be formulated with oxygenated PFC as described above or calcium hydroxide as an oxygen sources.

Synthesis of Foam Scaffolds Generally

The foam scaffold is adapted to fit the device, as appropriate. For tubular (or "hollow fiber") embodiments, the foam scaffold may form a cylindrical tube or rod, a rectangular tube or rod, or any other oblique shape, so as long as it can fit within the lumen of the hollow fiber. It will be appreciated that in some embodiments, the foam scaffold may have fins or other protrusions which may contact the inner wall of the hollow fiber.

In one embodiment of the invention, the cell device is formed from a hollow fiber membrane with a cylindrical internal foam scaffold.

The device may also be in the form of a flat sheet device. Flat sheet devices are described in detail in WO92/19195, U.S. Design applications 29/408366, 29/408368, 29/408370 and 29/423,365 and those Baxter publications previously mentioned. Such a flat sheet device of this invention is generally characterized by a first flat sheet membrane with a first interior surface, and a second flat sheet membrane with a second interior surface, the two membranes sealed at the periphery, with the foam scaffold positioned between the membranes. Cells may then be introduced through an access port, and the seal completed with a plug inserted into the port.

The devices of this invention may be formed according to any suitable method. In one embodiment, the foam scaffold may be pre-formed and inserted into a pre-fabricated jacket, e.g., a hollow fiber membrane, as a discrete component.

In Vivo Imaging Capability

In one embodiment, there is provided a means for imaging or detecting the cells inside the encapsulating devices in vivo. Imaging serves important roles in stem cell therapies. For example, noninvasive forms of imaging can be used to: (1) determine the presence, severity or phenotype of the cell and/or disease to be treated; (2) monitor engrafted cell therapies for the appearance of deleterious or non-target cell types and structures, such as cysts or microcysts; (3) guide the delivery of therapy; (4) follow the time-course of disease and evaluate the effects or efficacy of therapy; (5) provide labels and define mechanisms of therapy; (6) analyze and evaluate survival and function of engrafted cells; (7) detect and monitor device vascularization, which is important to encapsulated cell survival; and (8) generally facilitate the process of any cell therapy, e.g. by determining the engraftment, survival, and local function of cell therapy, including cell therapies described herein for treatment of diabetes by substitution and/or implanting pancreatic progenitor cells. In addition, although cell therapies aim to decrease morbidity/mortality, noninvasive imaging techniques as described herein and in more detail below can serve as a useful surrogate endpoint, for example, in preliminary trials or preclinical studies.

Any in vivo imaging technology is ideally: i) non-invasive; ii) reliably repetitive; iii) capable of tissue penetration up to a depth of at least 3 mm; iv) resolution capabilities of no greater than 500 μm and preferably no greater than 50 to 100 μm; v) imaging is not attenuated by device materials, e.g., can image through PTFE; vi) clinically compatible and not technically cumbersome or complicated; vii) commercially available; viii) FDA approved for human use; ix) reasonably cost-effective; and x) can image cells in a reasonable period of time (e.g., seconds or minutes), or any combination of the above.

To date, current methods include but are not limited to confocal microscopy, 2-photon microscopy, high and low frequency ultrasound, optical coherence tomography (OCT), photoacoustic tomography (PAT), computed tomography (CT), magnetic resonance imaging (MRI), single photon emission computed tomography (SPECT) and positron emission tomography (PET). These alone or combined can provide useful means to monitor the transplanted cells. Also, it is expected that such technologies will improve over time but that the essential tenets of how each technology functions or its utility is substantially similar. That said, in vivo imaging described herein is not intended to be limited to technologies described below but to technologies later discovered and described which would serve the same utility as that described herein.

In one embodiment, the imaging technique employed would be non-invasive and provide for a 3-dimensional tomographic data, have high temporal and spatial resolution, allow molecular imaging, and would be inexpensive and portable. While at present no single modality is ideal (discussed in more detail below), each has different attributes and these modalities together can provide complimentary information.

Confocal microscopy is an optical imaging technique that increases micrograph contrast and is capable of reconstructing three-dimensional images by using a spatial pinhole to eliminate out-of-focus light in specimens that are thicker than the focal plane. Since only one point in the sample is illuminated at a time, 2D or 3D imaging requires scanning over a regular raster (i.e. a rectangular pattern of parallel scanning lines) in the specimen. Three principal scanning variations are commonly employed to produce confocal microscope images. Fundamentally equivalent confocal operation can be achieved by employing a laterally translating specimen stage coupled to a stationary illuminating light beam (stage scanning), a scanned light beam with a stationary stage (beam scanning), or by maintaining both the stage and light source stationary while scanning the specimen with an array of light points transmitted through apertures in a spinning Nipkow or Nipkov disk. Each technique has performance features that make it advantageous for specific confocal applications, but that limits the usefulness of that feature for other applications.

All confocal microscopes rely on the ability of the technique to produce high-resolution images, termed optical sections, in sequence through relatively thick sections or whole-mount specimens. Based on the optical section as the basic image unit, data can be collected from fixed and stained specimens in single, double, triple, or multiple-wavelength illumination modes, and the images collected with the various illumination and labeling strategies will be in register with each other. Live cell imaging and time-lapse sequences are possible, and digital image processing methods applied to sequences of images allow z-series and three-dimensional representation of specimens, as well as the time-sequence presentation of 3D data as four-dimensional imaging. The use of above confocal microscopes is not limiting as other confocal microscopes now or later discovered are also encompassed in the embodiments described herein.

A large number of fluorescent probes are available that, when incorporated in relatively simple protocols, can stain certain cellular surface markers and/or proteins and intracellular organelles and structures, e.g., Celltracker, DiI, nuclear vital dyes, and the like. Fluorescent markers which specifically bind directly or indirectly to certain cell surface markers can be especially useful for identification of, for example, unwanted cell types. In one preferred embodiment, real time in vivo imaging for the presence of encapsulated pluripotent cells provides a means to detect, and therefore the potential to prevent, teratoma formation caused from pluripotent stem cells, such as hES or human embryonic gonadal cells or induced pluripotent stem (IPS) cells or parthenote cells and the like. The same means of detection can also identify pluripotent Stem cells which have escaped or leaked out of the device (or become un-encapsulated). Identification of such cells can also be performed using fluorescently labeled promoter genes OCT4 and NANOG that are up-regulated in expression in pluripotent stem cells. Similarly, certain intracellular fluorescent markers that label nuclei, the Golgi apparatus, the endoplasmic reticulum, and mitochondria, and even dyes such as fluorescently labeled phalloidins that target polymerized actin in cells, are also commercially available and can provide critical information about the fate of a cell.

In another embodiment, two-photon excited fluorescence (TPEF) microscopy is a noninvasive means to monitor differentiation or, stated in the reverse, to identify pluripotent stem cells (e.g., hESCs or IPS cells or parthenote cells) which did not differentiate and were inadvertently implanted as a very small percentage of the product cells that were encapsulated in the device described herein. Two-photon excited fluorescence microscopy relies substantially on endogenous sources of contrast, but can also detect, for example, fibrillar matrix molecules via second harmonic generation. In brief, two-photon microscopy relies on fluorescence emission similar to that employed by confocal microscopy. Rice et al. (2007) described that TPEF can be used to reveal quantitative differences in the biochemical status and the shape of differentiating and nondifferentiating stem cells in two-dimensional (2-D). See Rice et al. (2007) J Biomed Opt. 2007 November-December; 12(6), the disclosure of which is expressly incorporated by reference herein. In one embodiment, pluripotent stem cells can be genetically modified to express a fluorescent protein, e.g., enhanced green fluorescence protein, and driven by a pluripotent stem cell promoter (e.g., OCT4 or NANOG or any other pluripotent stem cell promoter later identified). For those implantable devices that are deeper than subcutaneous implants, i.e. deep below the skin surface, two-photon provides for a non-invasive deeper imaging than confocal microscopy. Further, the infrared light used is less harmful to living cells than visible or ultraviolet exposure, as the photon energy required for fluorescence excitation only occurs at the plane of focus and is not experienced by cells or tissues in the out-of-focus planes.

In still another embodiment, ultrasound is portable, essentially harmless, versatile, and can be done in real-time at the time of implantation of the encapsulated cell product and/or encapsulated biologically active agent or as a monitoring tool over the course of implantation. In particular, conventional low and/or corresponding high-frequency ultrasound can be used to provide qualitative as well as quantitative spectroscopic data. Although high-frequency ultrasound is capable of increased imaging resolution (30-80 μm over 20-50 MHz) as compared to clinical low-frequency ultrasounds (80 μm-1.5 mm over 1-20 MHz), it suffers from limited tissue penetration depth and limiting its use to superficial tissue sites. High-resolution imaging enables in vivo assessment of anatomical structures and hemodynamic function in longitudinal studies of a mammal. For example, Vevo by VisualSonics offers: (1) ability to perform longitudinal studies of disease progression and regression in individual subjects; (2) image resolution of anatomical and physiological structures of down to 30 microns; (3) ability to visualize image-guided needle injection and extraction; (4) microcirculatory and cardiovascular blood flow assessment; (5) high throughput via user-friendly equipment and research-driven interface; and (6) open architecture allowing comprehensive measurement and annotations and offline data analysis. The ability to assess microcirculatory and cardiovascular blood flow will assist in determining the viability of the cells, e.g. $O_2$ flow and delivery. In comparison, low-frequency ultrasound (about 7-10 mHz) has been shown to detect microstructural tissue changes that correlated with histological cell death in acute myeloid leukemia cells exposed to chemotherapy. See Azrif et al., Conventional low-frequency ultrasound detection in apoptosis, *Proceedings of the American Institute of Ultrasound in Medicine*, New York, N.Y. 2007 (AIUM Laura M.D., 2007) p. S185.

In another embodiment, magnetic resonance imaging (MRI) can be utilized to distinguish between healthy and diseased tissue using a contrast agent. Yet, in another embodiment, computerized tomography (CT) or CT scans can be used to create a detailed picture of the body's tissues and structure. Again here, a contrast agent is utilized and makes it easy to visualize abnormal tissue due to specific absorption rates. One use of a contrast agent such as Indium-111 (I-111) oxine is for tracking stem cells although it does have a short half-life. Still, in another embodiment, Positron Emission Tomography (PET) scans can be used to measure emissions from positron-emitting molecules e.g., carbon, nitrogen, and oxygen to name a few, and provide valuable functional information. In yet another embodiment, optical coherence tomography (OCT) or photoacoustic tomography (PAT) may also be used to examine cells and tissues inside and outside the device. OCT detects differences in the reflectivity of various tissues while PAT detects ultrasonic waves created when tissues are heated by exposure to low energy laser light.

Various methods and techniques or tools, alone or combined, can be employed to visualize, analyze and assess the implanted cells inside the device in vivo. These and other technologies now known or later developed can be utilized to the extent they allow for in vivo imaging and monitoring of the cells and/or agent as described herein.

EXAMPLES

Example 1

Extrapolating Therapeutic Effective Dose of PEC

To help ensure adoption by the patient population, an encapsulated cell therapy for the treatment of diabetes such as that intended by Applicants must preferably consist of the least number of macro-encapsulated cell product (also referred to as the "VC combination product") necessary to provide the therapeutic effective dose to treat the patient with the disease.

For patients with insulin-dependence diabetes, insulin independence requires about ~200,000 islet equivalents or "IEQ". IEQ is calculated based on the number and diameter of the islets present in the preparation, mathematically corrected for islet volume. An islet is about 150 µm in diameter. Islets of varying diameter are normalized to a number of IEQ of 150 µm diameter by mathematically compensating for their volumes. The therapeutic IEQ number to treat a patient with insulin-dependent type diabetes has been determined based on the description available for islet allo-transplantations (e.g. cadaveric donor islets), auto-transplantations and beta cell mass at the onset of diabetes. For allo-transplantations, the target IEQ is about 10,000 IEQ per kilogram of body weight; however, only about 40% of the islets survive, thus providing a therapeutic effect from about 4,000 IEQ/kg. In islet auto-transplantation, the entire islet mass isolated from the patient's pancreas is delivered back and the total IEQ is commonly 200,000 to 300,000 IEQ (total delivered) and frequently renders patient's independent of exogenous insulin. Similarly, islet survival in auto-transplantations is also an issue. See Korsgren et al. (2005), Current Status of Clinical Islet Transplantation, *Transplantation* 79: 1289-1293.

In view of the above, Applicants estimate that the total therapeutic IEQ necessary from a PEC graft is in the range of about 200,000 IEQ. FIG. 1, shows a graph depicting beta cell mass on the left and comparable IEQ on the right to obtain similar levels of beta cell mass and/or function on the left. Diabetes onset occurs at about 10-20% beta cell mass. However, there is a broad therapeutic cell (safety) index such that 100% beta cell mass ("normal", non-diabetes state) does not have to be restored in order to achieve insulin-independence or amelioration of the disease. Since PEC cells implanted do not contain islets and therefore does not equate to IEQ until after in vivo maturation, Applicants have measured the beta cell mass achieved in vivo based on total C-peptide protein content of encapsulated PEC grafts (or VC-01 grafts) explanted after in vivo maturation. The C-peptide is also measured in known numbers of IEQ for extrapolation of graft C-peptide content to IEQ. FIG. 2A is a graph showing total human C-peptide protein content from various numbers of human cadaveric islets. Aliquots of human islets at defined IEQ amounts were obtained from a 3rd party source range 500 to 5000 IEQ. Total human C-peptide content was measured using ELISA, and as shown in FIG. 1A, there is linear relationship as between the human islet number (IEQ) and the total C-peptide protein content (pM).

Using this defined linear relationship between IEQ number and C-peptide protein content, Applicant's were able to measure the total human C-peptide protein content of encapsulated PEC grafts which over the period of 4 to 11 months produced consistent total C-peptide content levels in the range of about 1400-2000 pM. See FIG. 1B. These total human C-peptide content levels then can be correlated to FIG. 1A to determine the range of IEQ delivered by VC-01 product at maturation. Specifically, see the dashed lines in FIG. 2B which demonstrates the 25th percentile and median of total human C-peptide found in matured VC-01 grafts among those sixty animals. When correlated to FIG. 1A these C-peptide levels correspond to about 2500 to about 3500 IEQ delivered by VC-01 grafts. Thus a small encapsulation device (functional volume of about 20 µL, or an EN20 device) can contain about 2,500 to 3,500 IEQ of beta cell mass or greater than 80,000 IEQ per kg in a mouse. Assuming the linearity of the relationship between functional volume of the encapsulation device and the capacity to hold a proportionately greater volume of therapeutic cells, a larger drug delivery device, for example, a device that holds about 250 µL functional volume (EN250 device) and is about 12.5 times (12.5×) greater than the EN20 device and can contain up to about 30,000 to 45,000 IEQ. Similarly, for an EN100 device (6.5× of the EN20 device) can contain up to about 16,250 to 22,750 IEQ; and an EN-(large capacity) LC device (48.4× of the EN20 device) containing 4 cell chambers, can contain up to about 121,000 to 169,400 IEQ, and so on. Hence, in order for the therapeutic effective dose to be delivered to a patient, it is anticipated that encapsulation using at least about 4, about 5, about 6, about 7, about 8 EN250 devices or about 2 EN-LC devices will be required to deliver sufficient PEC quantities. The larger capacity devices are described in more detail below.

Example 2

3-Dimensional Large Capacity Device Assemblies to Optimize Surface Area and Cell Volume for Cell Therapeutics In view of Example 1, Applicants set out to establish a large capacity-device that increases the functional cell dose per device, while at the same time limiting the device to occupy the least effective area (or footprint), e.g. the least amount of space possible on the anatomical site in the human body.

Applicant's proprietary drug delivery devices have been previously described in U.S. Design patent application Nos. 29/408,366; 29/408,368 and 29/408,370 filed Dec. 12, 2001 and 29/423,365 May 31, 2012, and in U.S. Pat. No. 8,278, 106, ENCAPSULATION OF PANCREATIC CELLS DERIVED FROM HUMAN PLURIPOTENT STEM CELLS, issued Oct. 10, 2012.

Effective area or footprint of a device is a 2 dimensional area in the x and y dimension that is occupied by the device, e.g. occupied by the device in the human body. The previously described devices are 2-dimensional, flat, or planar and therefore have certain size constraints when considering for use in humans, e.g. such devices can only get bigger (increase in effective area or footprint) to accommodate more cell product or cell mass. It is well known that human (cadaveric) islets have very little capacity for proliferation and there is massive cell loss upon transplantation. Korsgren et al. (2005) supra, reported that the survival rate of implanted human islets is estimated to be only about 10% to 20%, which is attributed to a thrombotic/inflammatory reaction that is elicited when islets come in direct contact with ABO-compatible blood and within a matter of minutes after transplant, leukocytes are seen to infiltrate the islets causing an instant blood-mediated inflammatory reaction (IBMIR) and causing cell loss. The same islet cell lost has also been reported after transplantation of rodent and human islets in experimental studies. See Korsgren et al., supra p 1291. Applicants' earlier studies showed that the implanted PEC cells have proliferative potential, and regardless of the number of cells initially seeded in the device (e.g. 1, 1.5, 3, 4.5, 6 or 9 million cells), they proliferate and mature to become insulin secreting cells. See U.S. Pat. No. 8,278,106 for example. Thus, it is the size, design and construction of the device and not the number of cells loaded into the device, that limits and determines the number of cells (or dose) present after maturation. And, the principle constraint on maximal cell number is not a cell capacity problem, but a physical device capacity problem.

FIGS. 3-70 illustrate various embodiments of a large capacity device assembly. As shown in the figures, the assemblies contain at least 2, preferably 3, preferably 4, preferably 5, preferably 6, preferably 7, preferably 8 or more cell chambers 100 per assembly or any number of a plurality of chambers 100 as necessary for a therapeutic dose. The large capacity devices are 3-dimensional and not flat or planar as previously described for the EN250 or the EN100 devices in U.S. Design application Nos. 29/408366, 29/408368 and 29/408370 filed Dec. 12, 2011; 29/423,365 filed May 31, 2012; and U.S. Pat. No. 8,278,106.

Figure 13:
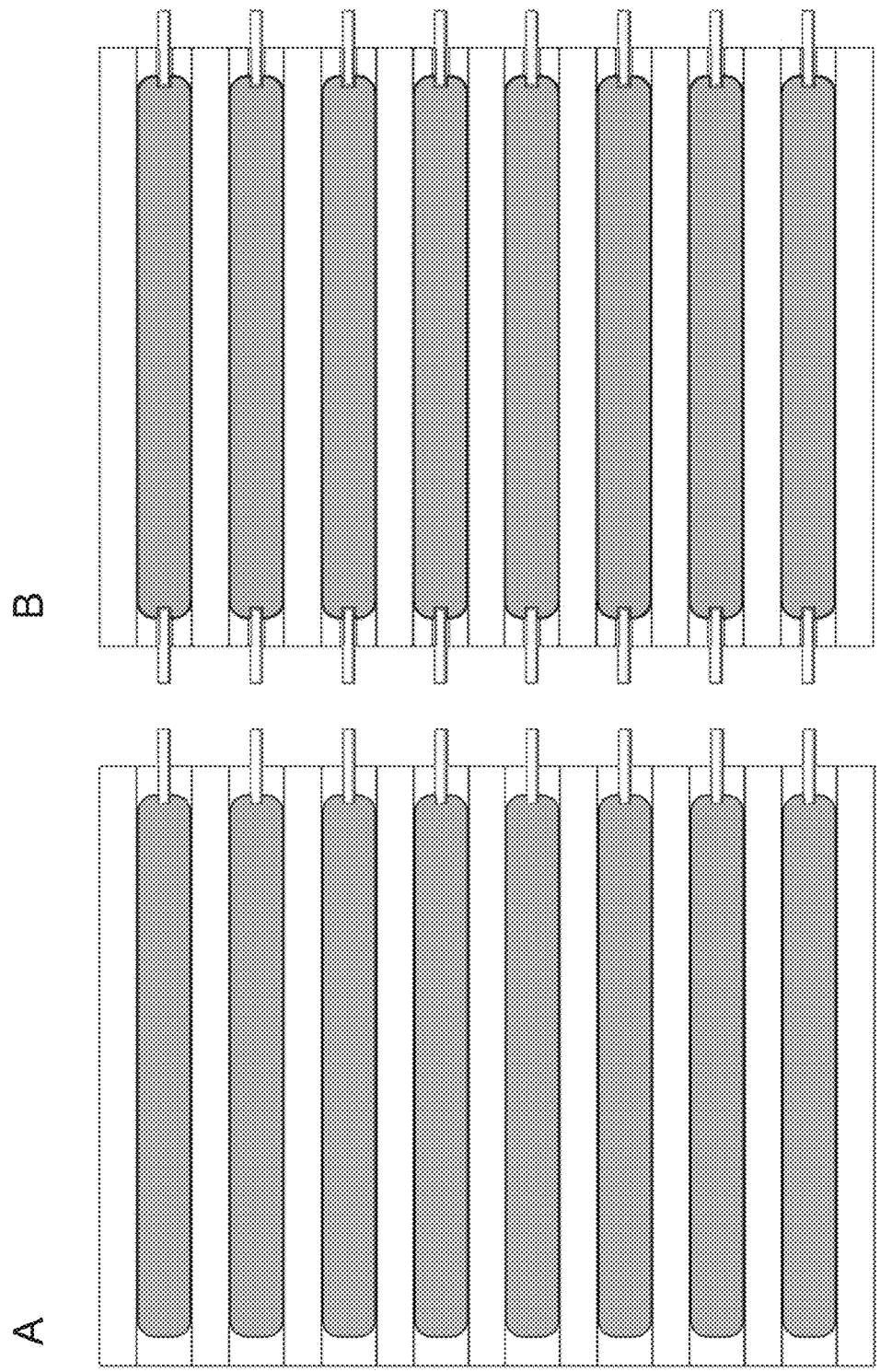

FIGS. 3-8 illustrate assemblies consisting of 8 cell chambers 100 or compartments. FIGS. 3, 4, 5A and 6 illustrate device assemblies folded with about a zero-degree angle (relative to the parallel facing chambers) in between each compartmentalized lumen or cell chamber 100. The fold or bend 40 occurs only in the bulkhead (or seal or cell free region between compartmentalized cell chambers) portion of the device assembly. FIGS. 7 and 8 illustrate assemblies where the cell chambers 100 are separated from each other at about 20-degree angle or 40-degree, respectively. Again, the assemblies form a 3-dimensional device by bending or folding the bulkhead or cell-free regions 40. The overall height (z-dimension) and width (x-dimension) will vary slightly depending on the degree of the folds or bends 40 at the bulkhead regions, e.g. when it is bent at 0-degrees the overall height and width are approximately 10.5 mm and 25.2 mm, but when they are bent at 20-degrees the overall height and width are approximately 9.2 mm and 44.0 mm. Thus, the overall effective area or footprint of the device assembly can be changed and manipulated by changing the nature of the folds in the device. FIGS. 4A, 13 and 14 show device assemblies prior to folding the assemblies.

In general, in order to optimize cell volume or cell density inside a cell chamber in any given device, there is a need to maximize a volume to effective area ratio. Effective area or footprint is a 2 dimensional area in the x and y dimension that is occupied by the device, e.g. occupied by the device in the human body. Table 1 shows in one embodiment, a 3-dimensional large capacity (3-D EN-LC) device assembly having 8 cell chambers, each cell chamber in this prototype having about 120 µL volume, for a max volume (MV) of about 968 µL. This 3-D EN-LC has an effective area (EA; x and y plane) of about 3420 mm² (38 mm×90 mm). The volume to effective area (MV/EA) ratio of the 3-D EN-LC device is about 0.283 (i.e., 968/3420). Compare this to one embodiment of a planar device, an EN250 device that has a maximum volume of about 249 µL and an effective area of 2295 mm² (27 mm×85 mm). The volume to effective area (MV/EA) ratio of this planar EN250 device is about 0.108 (i.e. 249/2295). So, the 3-D EN-LC device can hold 4 times the volume of the planar EN250 device, yet without taking up 4 times the effective area to do such. That is, the volume to effective area ratio of the 3-D EN-LC device is greater (or better) as compared to the planar EN250 device, thus allowing for more cells to be encapsulated over the same effective area or footprint. The 3-D EN-LC device can accomplish this increased volume to effective area ratio because it can folded in the z dimension (height) without restrictions; and is about 9 to 10-fold greater in height than the EN250 device. The EN250 device is restricted in the z dimension by its maximal lumen diameter of about 1 mm.

TABLE 1

Comparison of Planar vs. 3-Dimensional Devices

| | 3-D EN-LC (8 Cell chambers) | Planar EX250 device (1 cell chamber) |
|---|---|---|
| Max Volume (µL) | 968 µL | 249 µL |
| X, Y Effective Area (EA, mm²) | 38 mm × 90 mm | 27 mm × 85 mm |
| Max Volume/EA | 0.283 | 0.108 |
| Height (Z) | 9-10 mm | ~1 mm |

Table 1 compared device assemblies as illustrated in FIGS. 3, 4 and 5A, other designs which employ the principle of creating angles and/or bends 40 in the device assembly to increase total volume to effective area ratio can be accomplished without deviating from the description above and that described herein. For example, FIGS. 6-14, illustrate device assemblies in the form of a roman shade (FIGS. 9, 15-28), tube or series of tubes, or flat tube (FIGS. 10, 29-42), comb-like or fin-like (FIGS. 11, 43-56), wave or U-shape or shutter (FIGS. 3, 4, 5A, 6, 7), shutter (FIGS. 12, 57-70), radiator, surface texturing, wafer, coil and the like. These devices can have multiple cell chambers 100, ports 20, 30, and varying degrees of the folds or bends 40. All these devices are embodied herein and illustrated because such designs would similarly increase volume to effective area ratio of the device.

Table 2 compares the volume to effective ratio of additional embodiments of 3-dimensional large capacity devices assemblies. For purposes of comparing the different embodiments, the effective area (or footprint) is kept constant at 50×20 mm, or 1000 mm². For the calculations in Table 2, the overall height (z dimension) is also kept constant at about 2 mm for all embodiments, except for the flat planar device, which has a lumen thickness of about 0.2 mm (the thickness is limited by the thickness of the cell chamber itself). Additionally, for the 3-dimensional large capacity device assemblies, there is also a gap of about 0.6 mm between each cell chamber. The volume of each embodiment is the maximal volume for the device. The roman shade design (FIG. 9) is capable of having greatest volume whereas the flat (planar, 2-dimensional) device is capable of having the least volume. Hence, the embodiment with the greatest maximum volume to effective area ratio is also the roman shade device and the embodiment with the least maximum volume to effective area ratio is the flat device.

TABLE 2

Comparison of Embodiments of 3-Dimensional Large Capacity Device Assemblies

| | Roman Shade (FIG. 9) | Fin (FIG. 11) | U-Shape (FIG. 3, 4, 6) | Shutter (FIG. 12) | Flat Tube (FIG. 10) | Flat |
|---|---|---|---|---|---|---|
| Effective Area (EA, mm²) | 1000 | 1000 | 1000 | 1000 | 1000 | 1000 |
| Max Volume (V, µL) | 710 | 693 | 560 | 500 | 493 | 200 |
| Max Volume/EA | 0.71 | 0.69 | 0.56 | 0.5 | 0.49 | 0.2 |
| Max Volume/Flat Vol | 3.55 | 3.46 | 2.8 | 2.5 | 2.46 | 1 |

Thus, similar to Table 1, Table 2 demonstrates that unless the devices can take advantage of the z-dimension (height)

the maximal volume to effective ratio will be restricted. By adding this extra z-dimension, and various design configurations described herein which take into account this z-dimension, the 3-dimensional large capacity device assemblies herein can optimize cell delivery for those cell therapies or replacements where a high cell dose or number is required (e.g., type 1 diabetes mellitus).

The device assembly embodiments herein are manufactured generally by standard cutting modalities including but not limited to laser and/or die cutting each of the layers or components, e.g. mesh, adhesive film and cell-impermeable layer. The components are aligned such that when each component or layer is placed in the welder, each of the lumens can be aligned or layered on top of one another appropriately. FIG. 13 illustrates a first seal 10 around the periphery of a first cell chamber is formed by welding all layers into to form a flat sheet simultaneously. Precision of the welding can be facilitated by adding alignment features attached thereto as part of each layer during the laser cutting, which can then be trimmed at the time of welding or forming the first seal or after. The seals can also be accomplished using high frequency ultrasonic welding, heat sealing, adhesive bonding, and fastening. To form the 3-dimensional assembly after the cell chambers have been created, the assembly is pre-treated using sufficient heat that allows for the cell-free regions between the cell chambers to take on or impart a smaller angle for the 3-D construction. The device assembly is then placed in a mold and heat is used to impart a substantially permanent construction. Still, forming the 3-dimensional assembly can be accomplished in a variety of ways, which one of ordinary in the skill in the art will be aware. For example, the device assembly can be molded or formed (e.g. clamping) or extruded, or an external frame/material with the imparted folded shape can be attached. The external frame/material can be attached in a variety of ways (e.g. high frequency ultrasonic welding, heat sealing, adhesive bonding, and fastening). FIGS. 3-70 illustrate that the angle of the bends or folds 40 during such construction can be of variable angles as shown in FIGS. 3-70. Alternatively, other 3-dimensional large capacity devices have been formed by molding a single large capacity device for example.

Figure 14B:
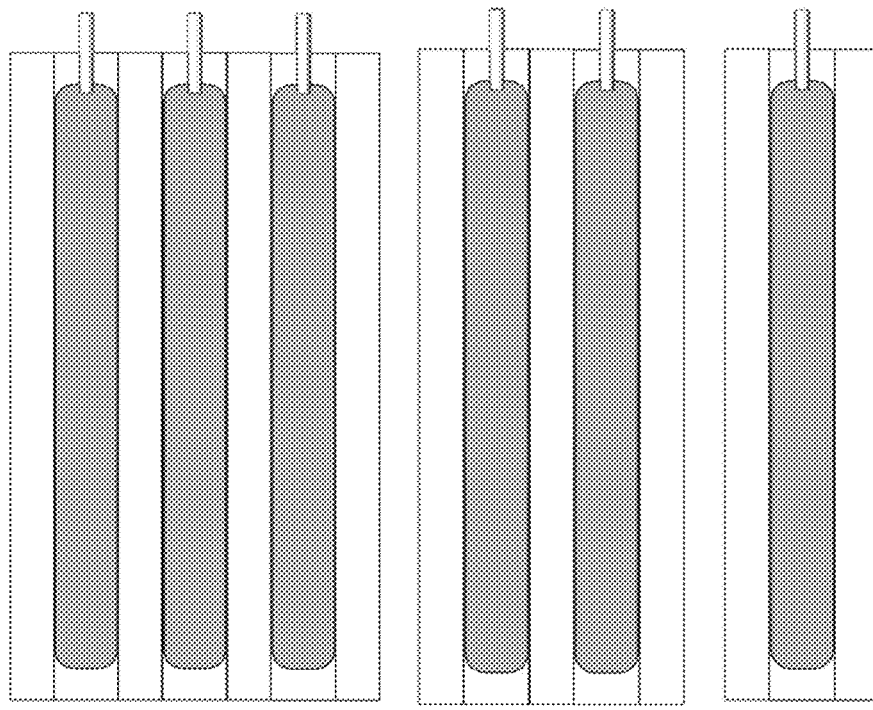
FIGS. 14A-B are perspective top views of two embodiments of cell-encapsulation large capacity device assemblies containing sixteen cell chambers having one port (FIG. 14A); and modular manufacturing of device assemblies with one, two, three or more cell chambers having one port (FIG. 14B).
Figure 14A:
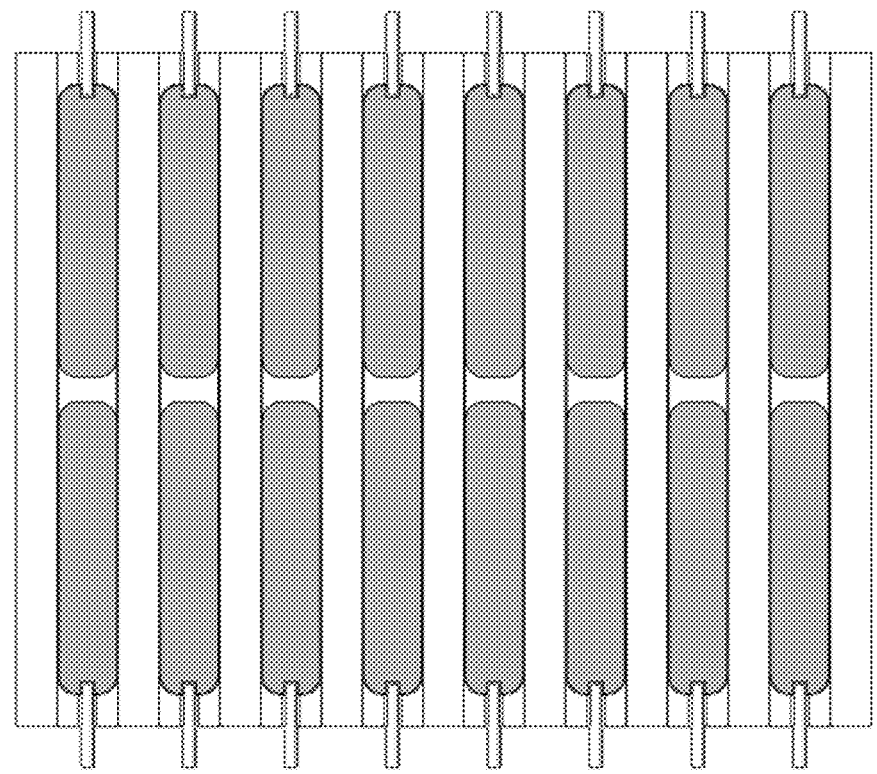
Figure 17:
FIG. 17 is a front elevation view of the 3-dimensional large capacity cell encapsulation device or assembly with multiple cell chambers and a single port per cell chamber.
Figure 19:
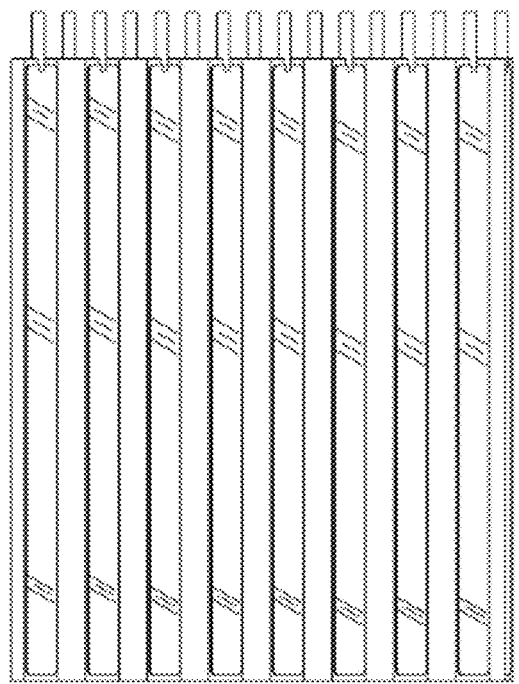
FIG. 19 is a bottom plan view of the 3-dimensional large capacity cell encapsulation device or assembly with multiple cell chambers and a single port per cell chamber.
Figure 16:
FIG. 16 is a back elevation view of the 3-dimensional large capacity cell encapsulation device or assembly with multiple cell chambers and a single port per cell chamber.
Figure 18:
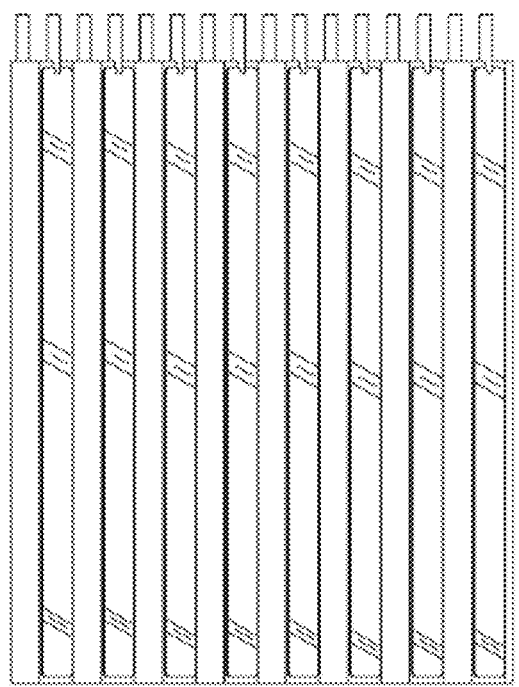
FIG. 18 is a top plan view of the 3-dimensional large capacity cell encapsulation device or assembly with multiple cell chambers and a single port per cell chamber.
Figure 20:
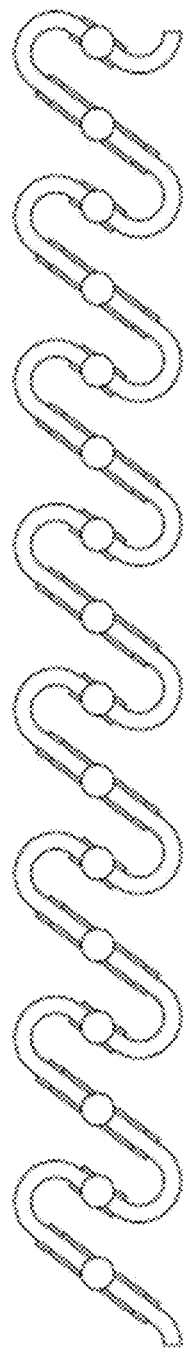
FIG. 20 is a right elevation view of the 3-dimensional large capacity cell encapsulation device or assembly with multiple cell chambers each having a port (circle), and whereby the cell chambers are parallel to each other.
Figure 21:
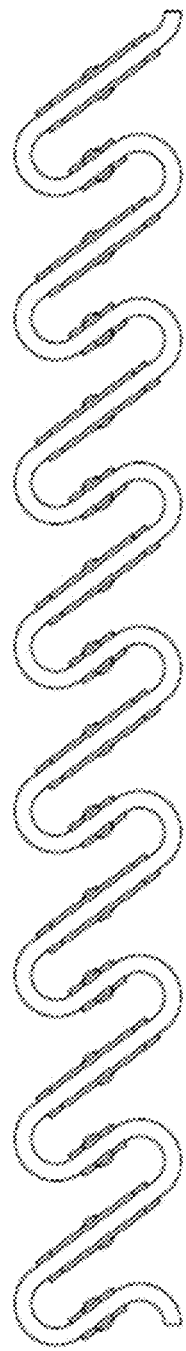
FIG. 21 is a left elevation view of the 3-dimensional large capacity cell encapsulation device or assembly with multiple cell chambers each having a port (circle), and whereby the cell chambers are parallel to each other.
Figure 22:
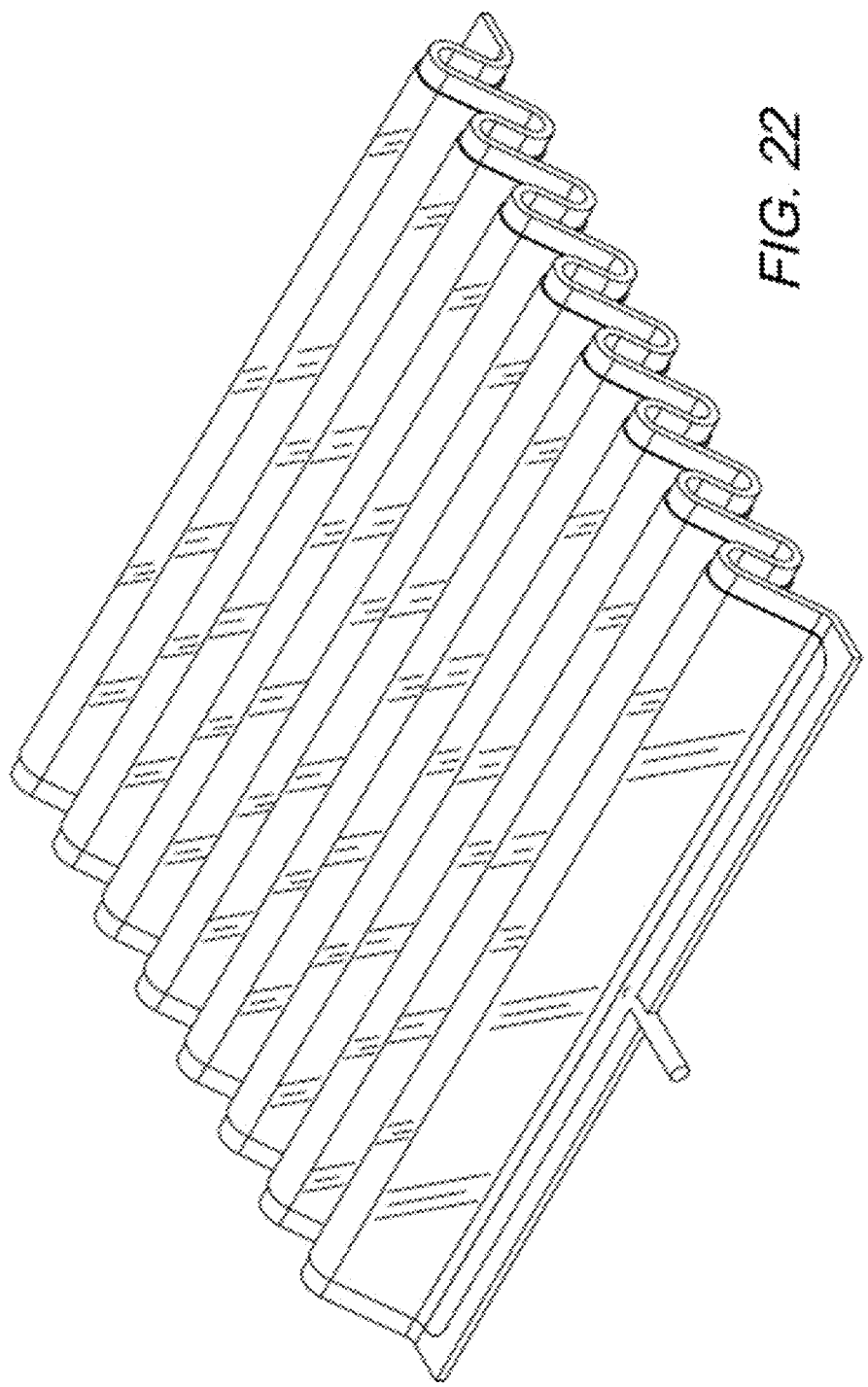
FIG. 22 is a perspective view of the 3-dimensional large capacity cell encapsulation device or assembly with multiple cell chambers and a single port per cell chamber.
Figure 27:
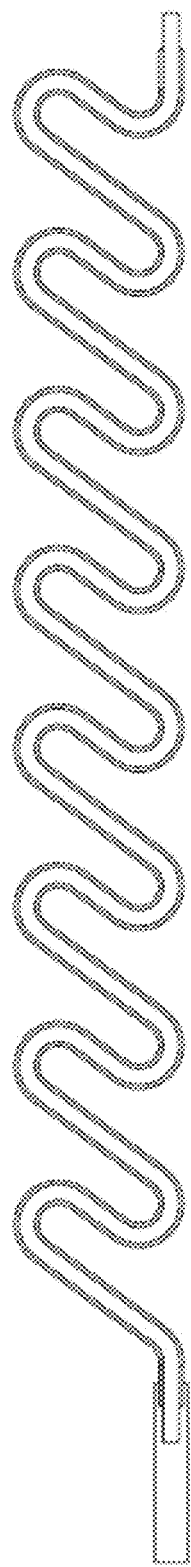
FIG. 27 is a right elevation view of the 3-dimensional large capacity cell encapsulation device or assembly with multiple cell chambers each having a port (circle), and whereby the cell chambers are parallel to each other.
Figure 28:
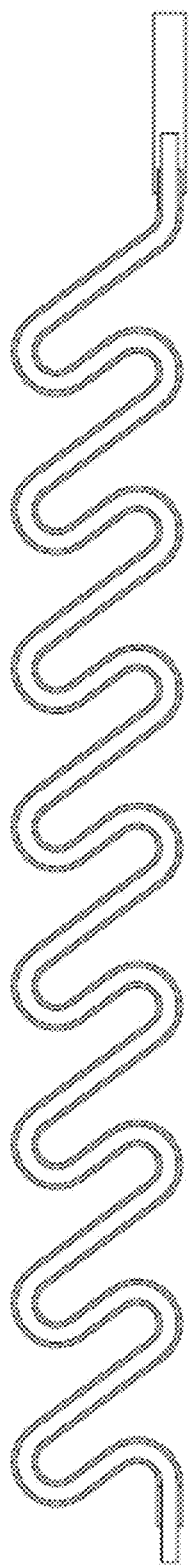
FIG. 28 is a left elevation view of the 3-dimensional large capacity cell encapsulation device or assembly with multiple cell chambers each having a port (circle), and whereby the cell chambers are parallel to each other.
Figure 29:
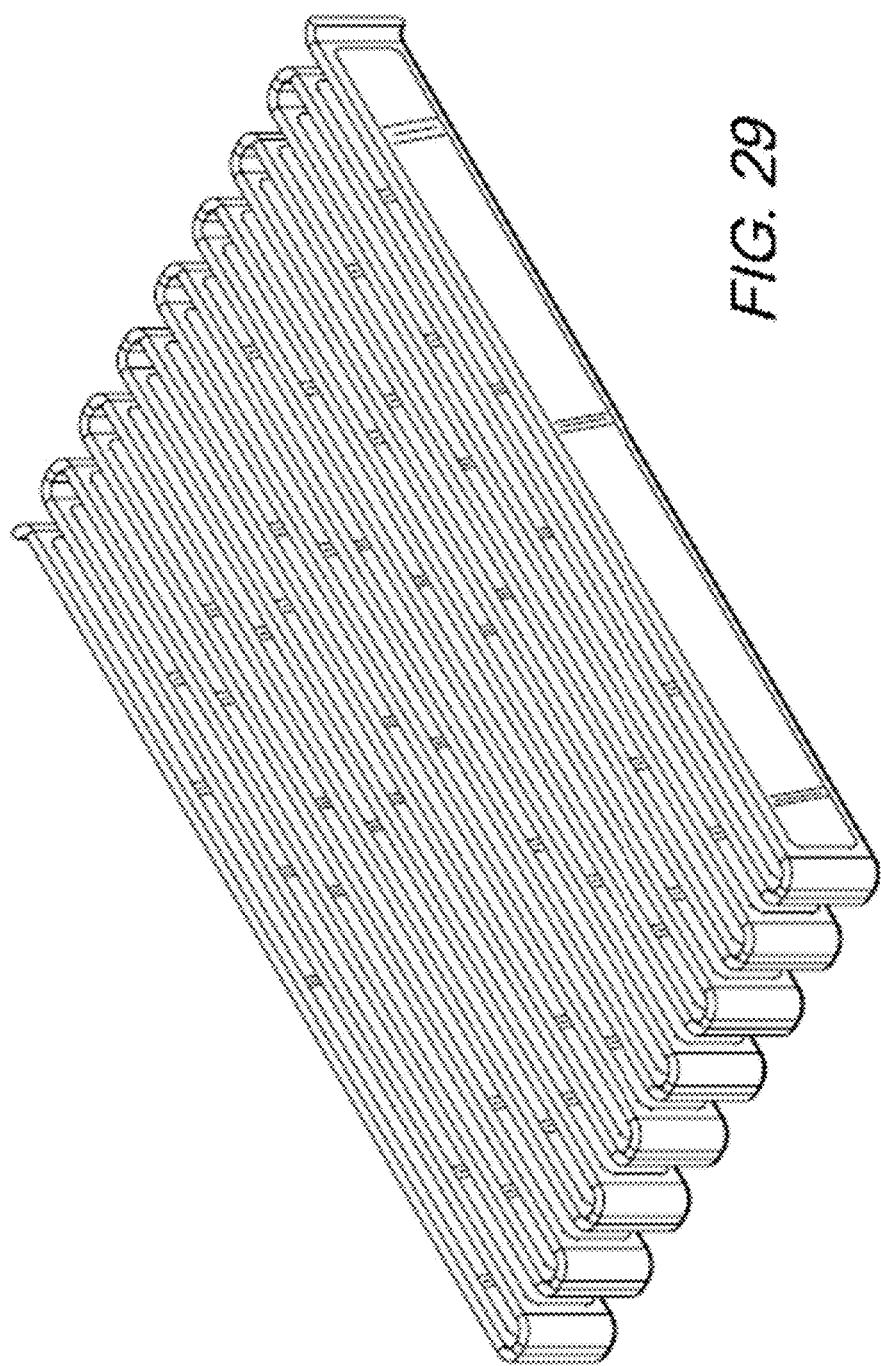
FIG. 29 is a perspective view of the 3-dimensional large capacity cell encapsulation device or assembly with a single cell chamber in the shape and form of a tube and having a port on each end.
Figure 30:
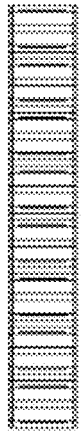
FIG. 30 is a back elevation view of the 3-dimensional large capacity cell encapsulation device or assembly with a single cell chamber in the shape and form of a tube and having a port on each end.
Figure 32:
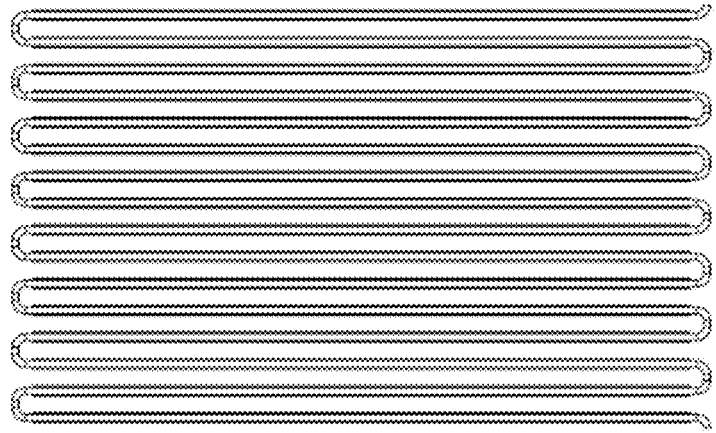
FIG. 32 is a top plan view of the 3-dimensional large capacity cell encapsulation device or assembly with a single cell chamber in the shape and form of a tube and having a port on each end.
Figure 31:
FIG. 31 a front elevation view of the 3-dimensional large capacity cell encapsulation device or assembly with a single cell chamber in the shape and form of a tube and having a port on each end.
Figure 33:
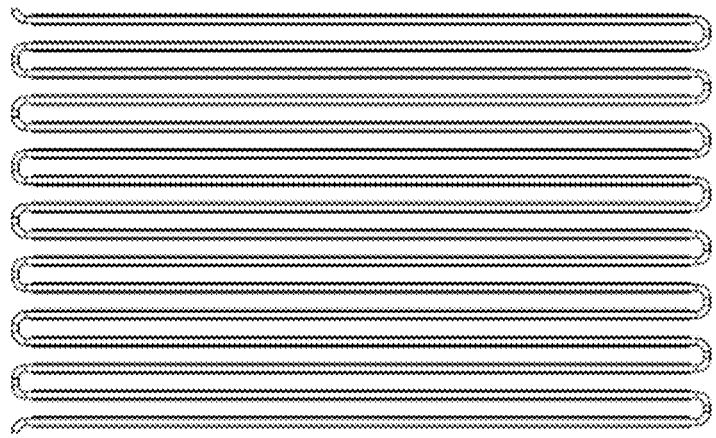
FIG. 33 is a bottom plan view of the 3-dimensional large capacity cell encapsulation device or assembly with a single cell chamber in the shape and form of a tube and having a port on each end.
Figure 34:
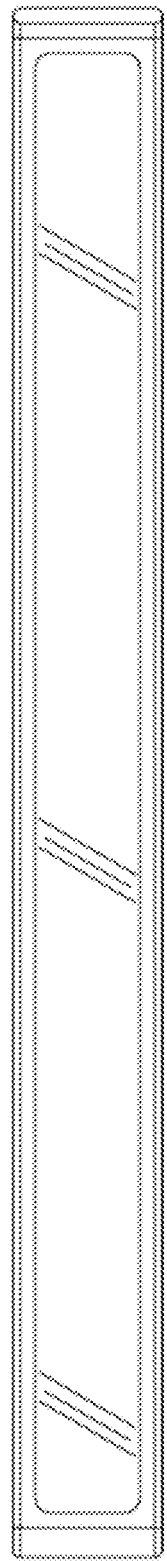
FIG. 34 is a right elevation view of the 3-dimensional large capacity cell encapsulation device or assembly with a single cell chamber in the shape and form of a tube and having a port on each end.
Figure 35:
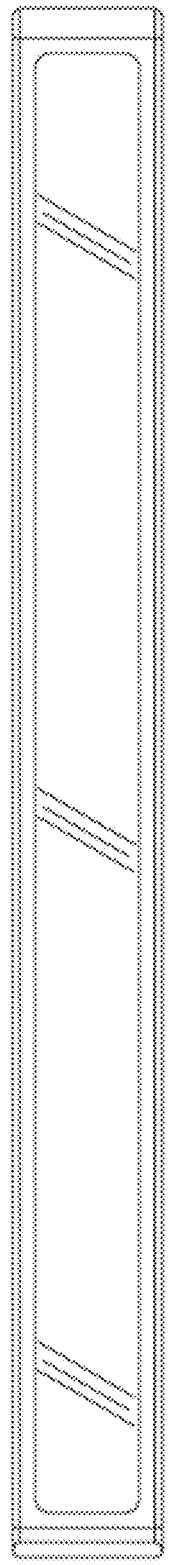
FIG. 35 is a left elevation view of the 3-dimensional large capacity cell encapsulation device or assembly with a single cell chamber in the shape and form of a tube and having a port on each end.
Figure 36:
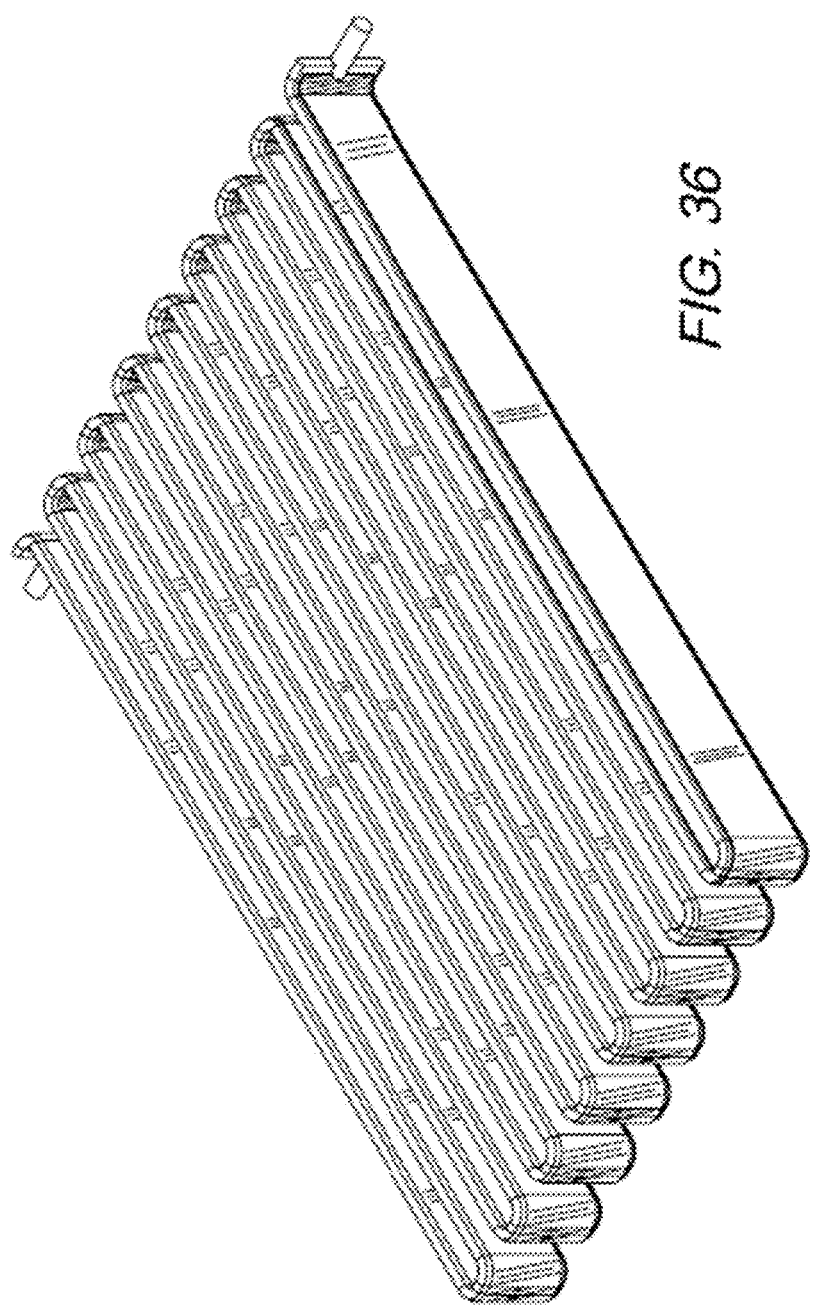
FIG. 36 is a perspective view of the 3-dimensional large capacity cell encapsulation device or assembly constructed from single modular units with cell chambers on each side.
Figures 37, 38:
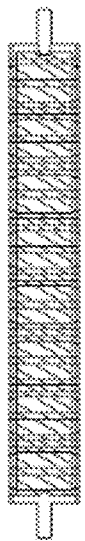
FIG. 37 is a back elevation view of the 3-dimensional large capacity cell encapsulation device or assembly constructed from single modular units with cell chambers on each side.
FIG. 38 is a front elevation view of the 3-dimensional large capacity cell encapsulation device or assembly constructed from module cell chamber units, and although the drawing figures show eight such units assembled, a greater or lesser number of units may be assembled for the device.
Figure 40:
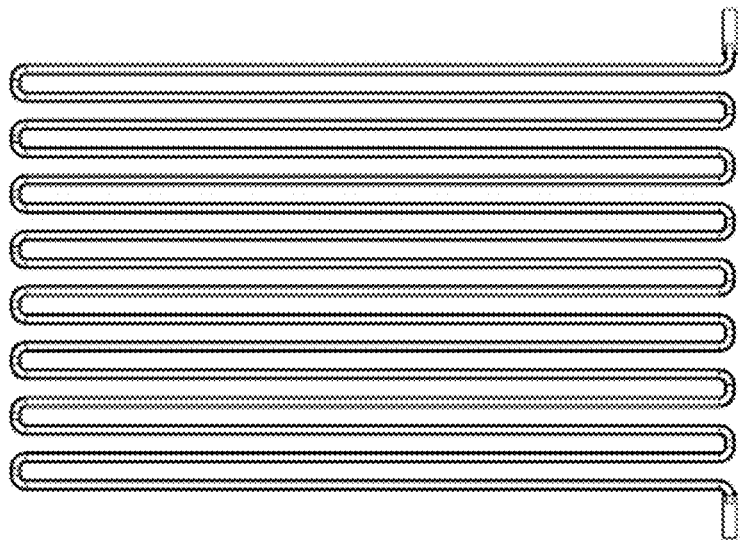
FIG. 40 is a bottom plan view of the 3-dimensional large capacity cell encapsulation device or assembly constructed from single modular units with cell chambers on each side.
Figure 39:
FIG. 39 is a top plan view of the 3-dimensional large capacity cell encapsulation device or assembly constructed from single modular units with cell chambers on each side.
Figure 43:
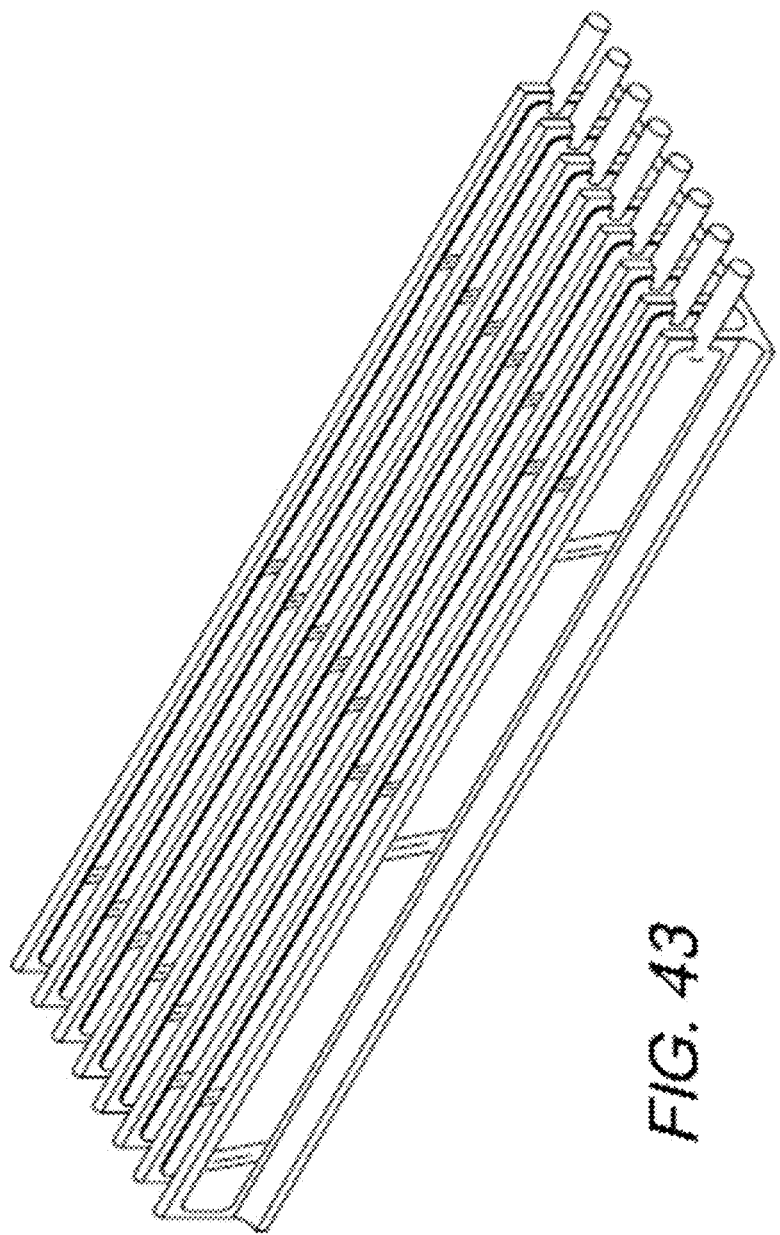
FIG. 43 is a perspective view of the 3-dimensional large capacity cell encapsulation device or assembly with multiple cell chambers and single ports.
Figure 44:
FIG. 44 is a back elevation view of the 3-dimensional large capacity cell encapsulation device or assembly with multiple cell chambers and single ports.
Figure 46:
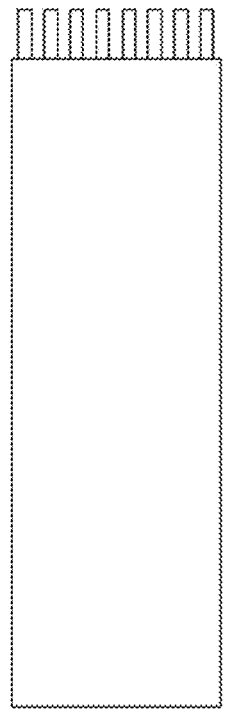
FIG. 46 is a top plan view of the 3-dimensional large capacity cell encapsulation device or assembly with multiple cell chambers and single ports.
Figure 45:
FIG. 45 is a front elevation view of the 3-dimensional large capacity cell encapsulation device or assembly with multiple cell chambers and single ports.
Figure 47:
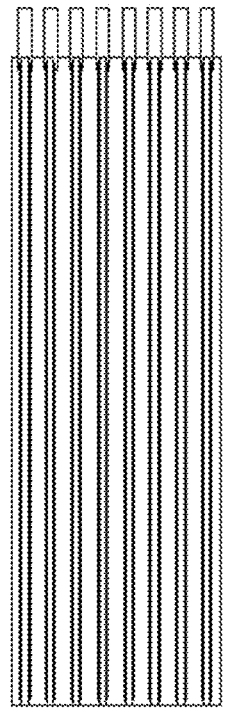
FIG. 47 is a bottom plan view of the 3-dimensional large capacity cell encapsulation device or assembly with multiple cell chambers and single ports.
Figure 48:
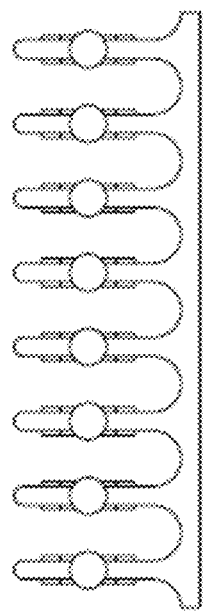
FIG. 48 is a right elevation view of the 3-dimensional large capacity cell encapsulation device or assembly with multiple cell chambers and single ports (circle), whereby the cell chambers are facing parallel to each other.
Figure 49:
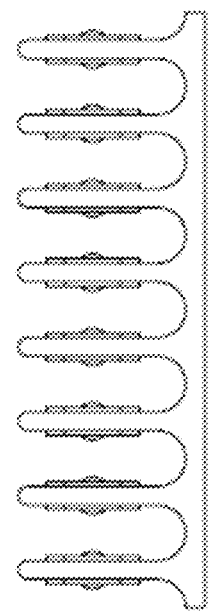
FIG. 49 is a left elevation view of the 3-dimensional large capacity cell encapsulation device or assembly with multiple cell chambers and single ports (circle), whereby the cell chambers are facing parallel to each other.
Figure 50:
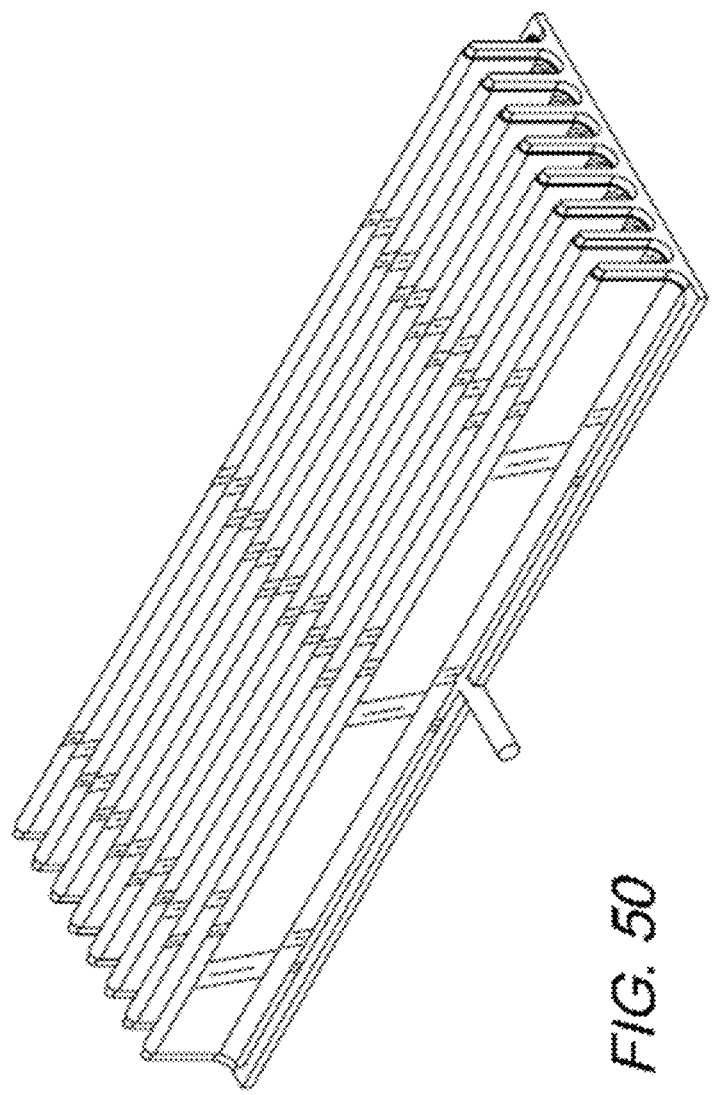
FIG. 50 is a perspective view of the 3-dimensional large capacity cell encapsulation device or assembly with a single cell chamber and port.
Figure 55:
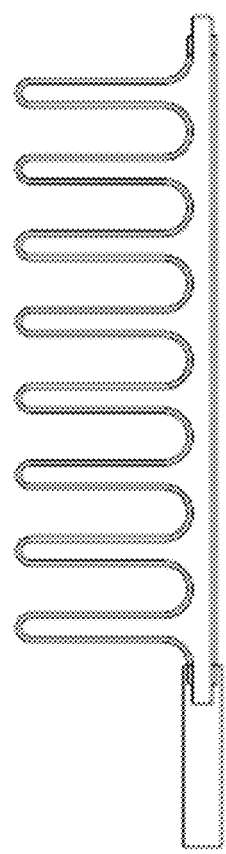
FIG. 55 is a right elevation view of the 3-dimensional large capacity cell encapsulation device or assembly with a single cell chamber and port.
Figure 56:
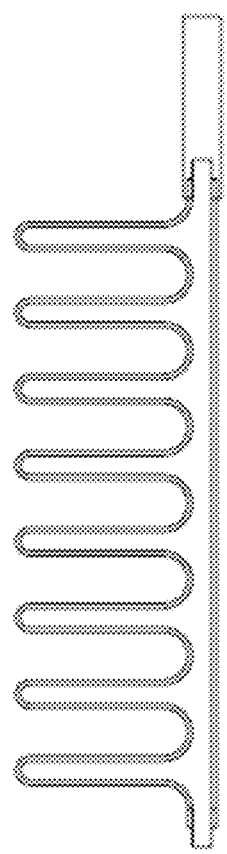
FIG. 56 is a left elevation view of the 3-dimensional large capacity cell encapsulation device or assembly with a single cell chamber and port.
Figure 57:
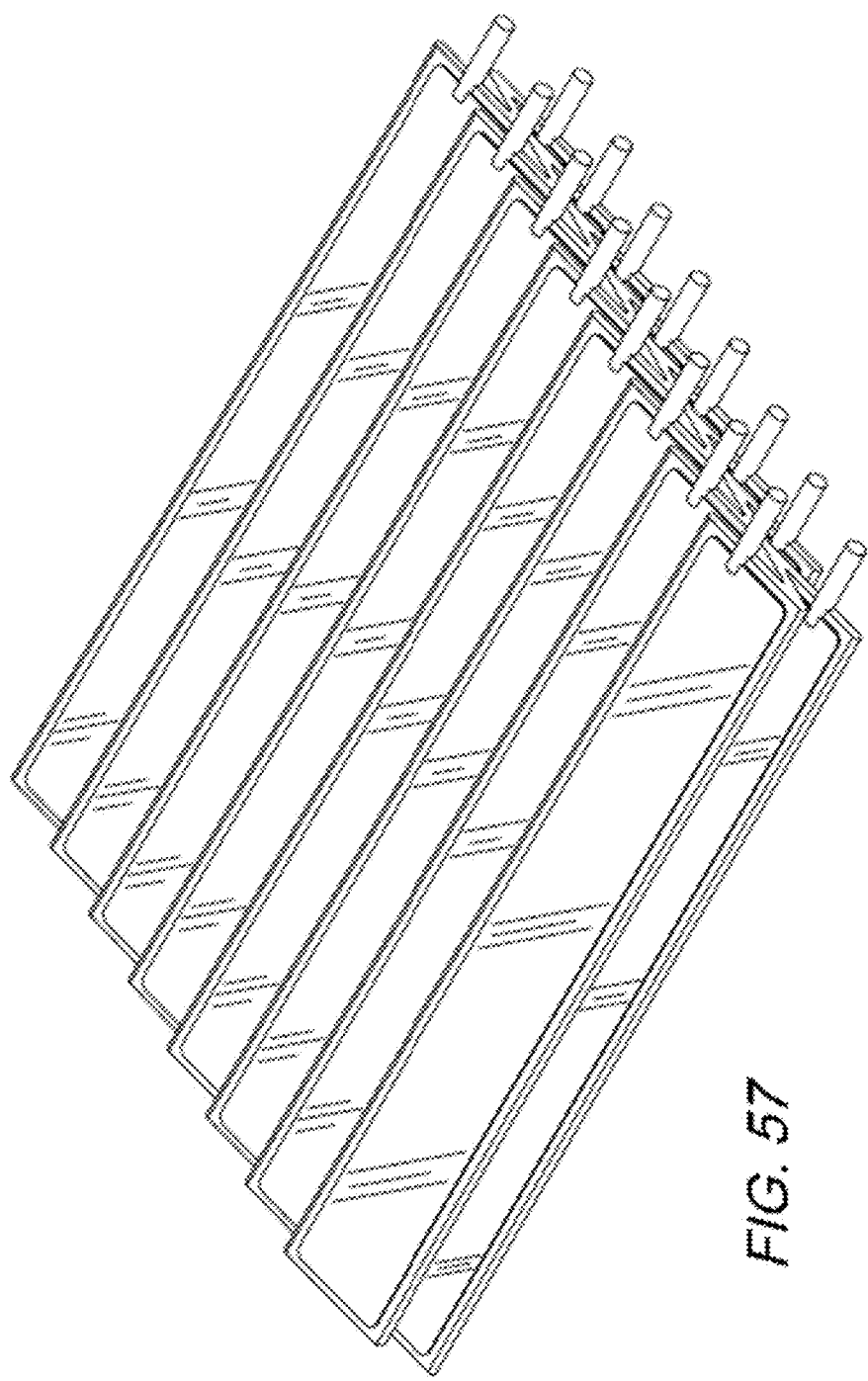
FIG. 57 is a perspective view of the 3-dimensional large capacity cell encapsulation device or assembly with multiple cell chambers and single ports, the assembly resembles a plantation shutter design.
Figure 59:
FIG. 59 is a front elevation view of the 3-dimensional large capacity cell encapsulation device or assembly with multiple cell chambers and single ports.
Figure 61:
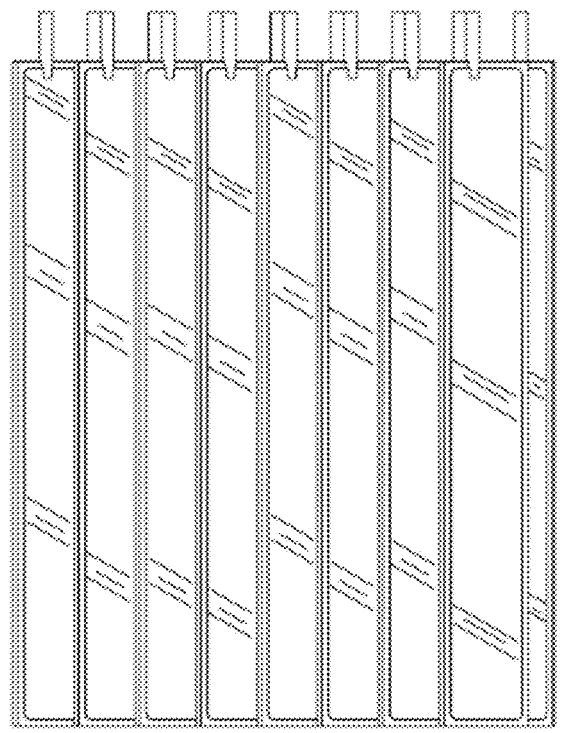
FIG. 61 is a bottom plan view of the 3-dimensional large capacity cell encapsulation device or assembly with multiple cell chambers and single ports.
Figure 58:
FIG. 58 is a back elevation view of the 3-dimensional large capacity cell encapsulation device or assembly with multiple cell chambers and single ports.
Figure 60:
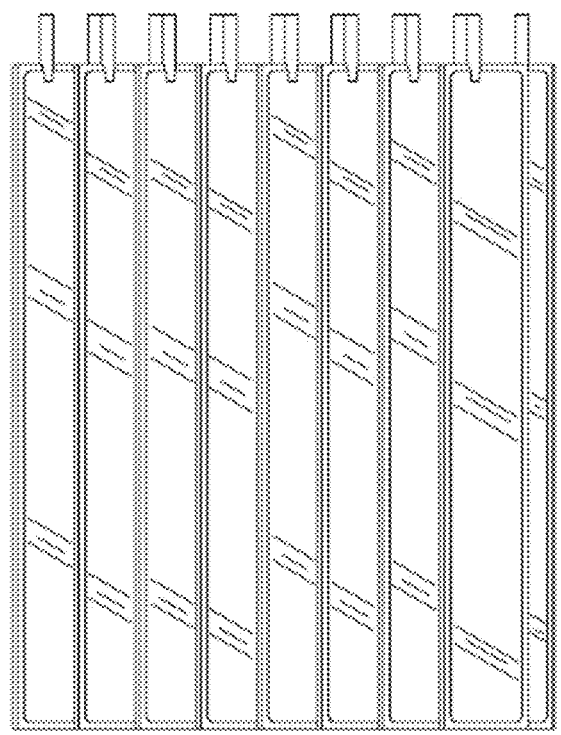
FIG. 60 is a top plan view of the 3-dimensional large capacity cell encapsulation device or assembly with multiple cell chambers and single ports.
Figure 62:
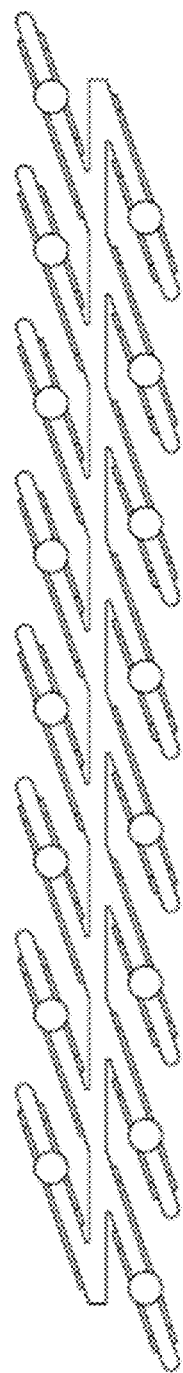
FIG. 62 is a right elevation view of the 3-dimensional large capacity cell encapsulation device or assembly with multiple cell chambers and single ports (circle), the assembly resembles a plantation shutter design.
Figure 63:
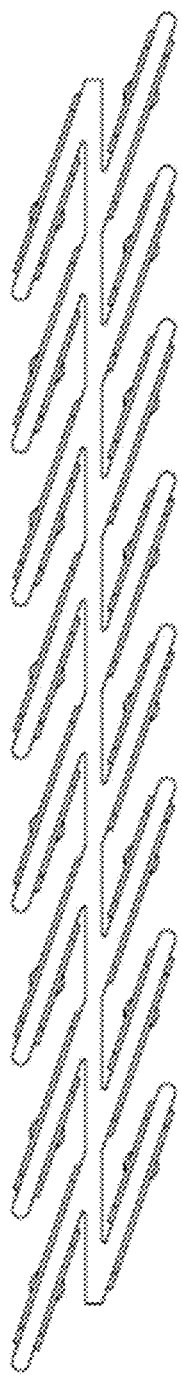
FIG. 63 is a left elevation view of the 3-dimensional large capacity cell encapsulation device or assembly with multiple cell chambers and single ports with multiple cell chambers and single ports, the assembly resembles a plantation shutter design.
Figure 64:
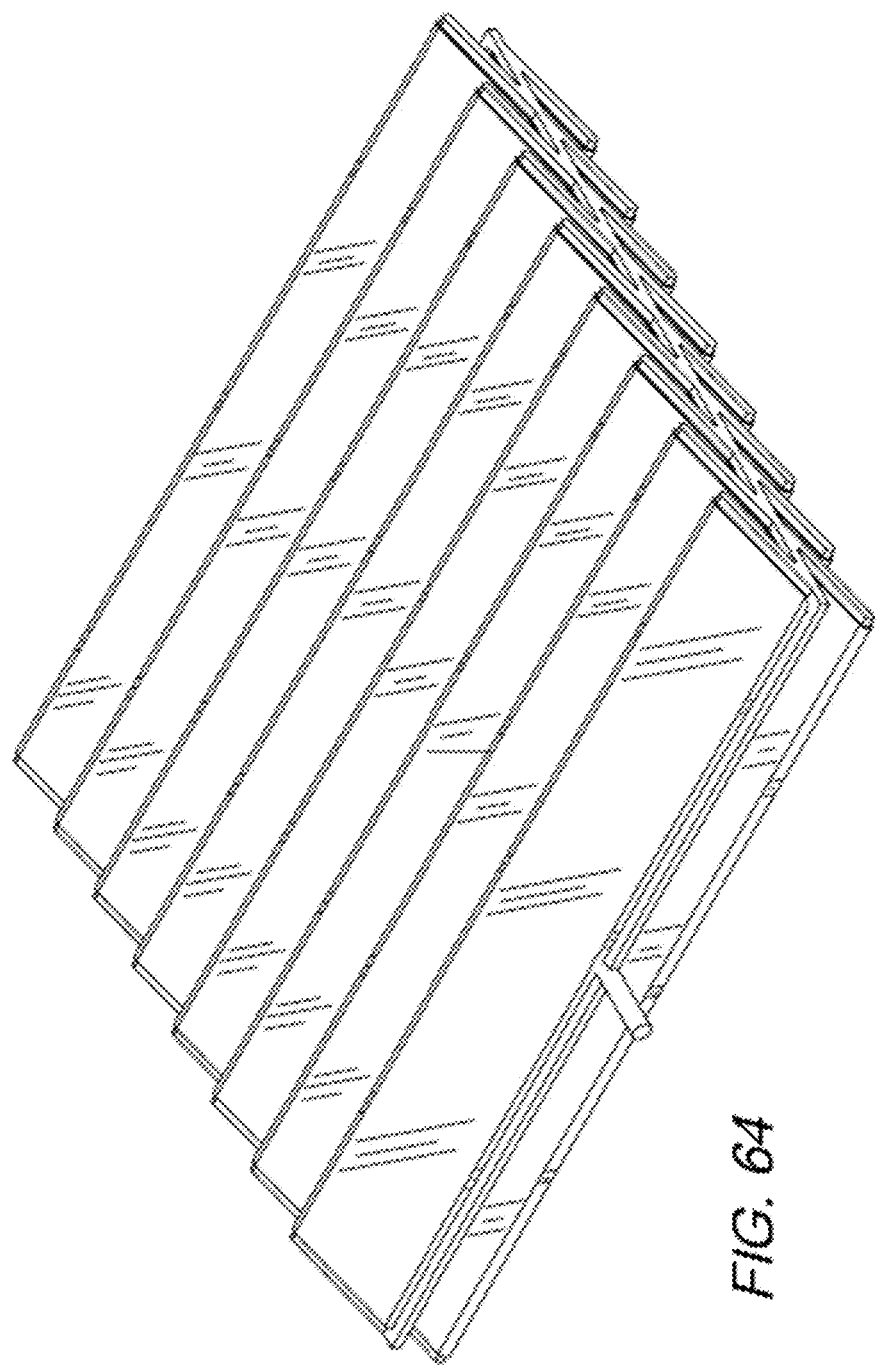
FIG. 64 is a perspective view of the 3-dimensional large capacity cell encapsulation device or assembly with a single cell chamber and single port, the assembly resembles a plantation shutter design.
Figure 66:
FIG. 66 is a front elevation view of the 3-dimensional large capacity cell encapsulation device or assembly with a single cell chamber and single port.
Figure 68:
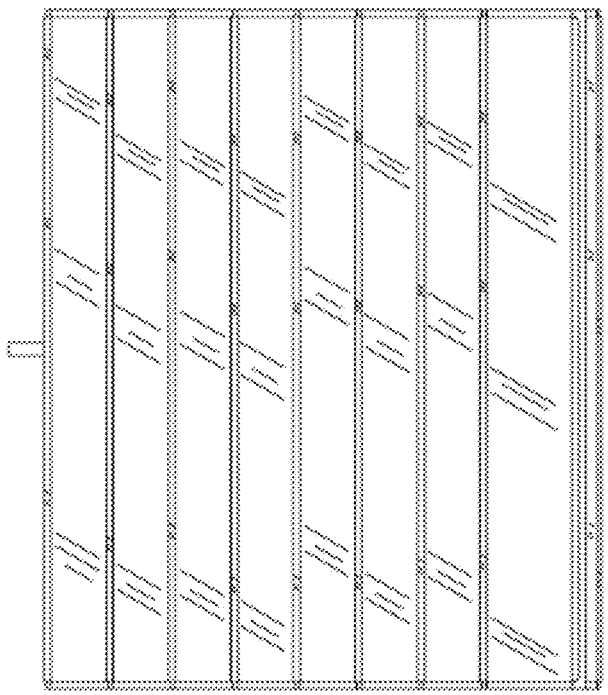
FIG. 68 is a bottom plan view of the 3-dimensional large capacity cell encapsulation device or assembly with a single cell chamber and single port.
Figure 65:
FIG. 65 is a back elevation view of the 3-dimensional large capacity cell encapsulation device or assembly with a single cell chamber and single port.
Figure 67:
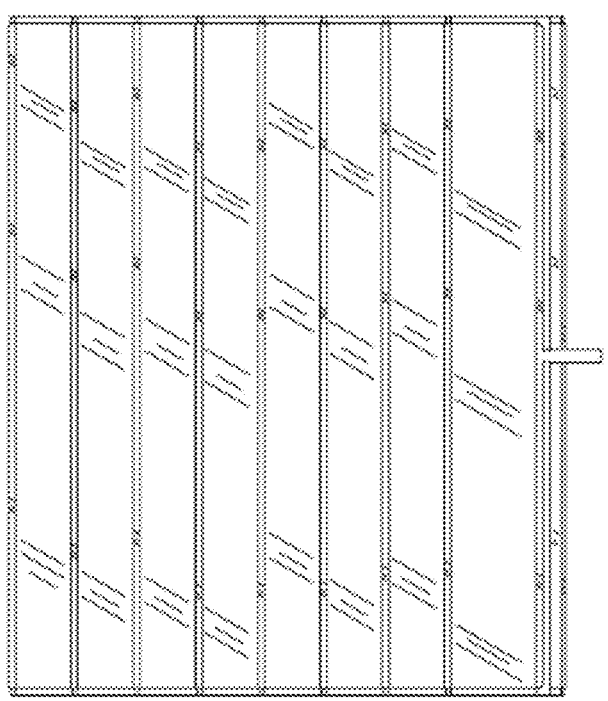
FIG. 67 is a top plan view of the 3-dimensional large capacity cell encapsulation device or assembly with a single cell chamber and single port.
Figure 69:
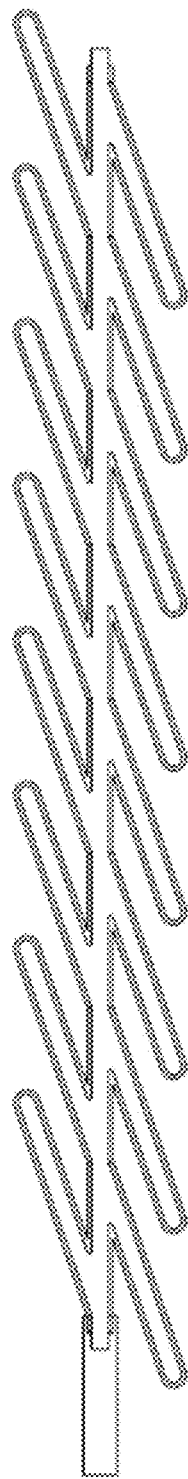
FIG. 69 is a right elevation view of the 3-dimensional large capacity cell encapsulation device or assembly with a single cell chamber and single port, the assembly resembles a plantation shutter design.

For modular production, FIG. 14A and FIG. 14B illustrates that any number of cell chambers 100 can be formed with any number of additional second seal, third, fourth, fifth, sixth, seventh, or eight or more seals 10 to form the desired corresponding number of cell chambers. Alternatively, the entire multi-chamber device can be performed in one step whereby the weld forms all cell chambers simultaneously. Preferably, the device assembly can be manufactured by building each device assembly, or even each cell chamber in the device assembly, discretely, such that the number of cell chambers is elected based on the cell dose for any given patient. Similar to the above, modular production can employ any method available in the art including high frequency ultrasonic welding, heat sealing, adhesive bonding, and fastening so long as such methods do not compromise the integrity or function of the device assembly.

Additionally, the cell-free regions or folds in the 3-dimensional construct of the device can be perforated to allow host cell invasion, for example, allowing blood vessels to traverse through the perforations from either surface or side of the device and thereby increasing vascularization of the device and the cells therein.

Figure 71:
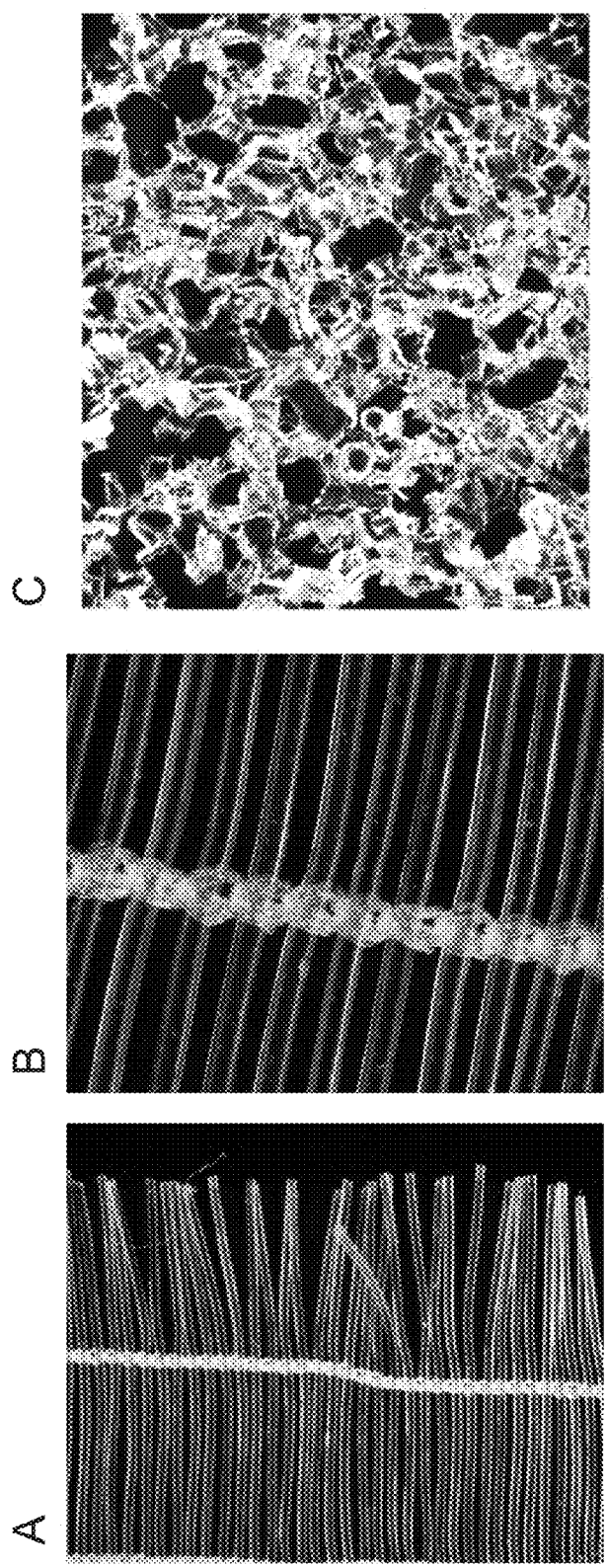
FIGS. 71A-C are photo images of silicon-based hollow fiber tubes woven to form a mat (FIG. 71A-B) and silicone based elastomer foam (FIG. 71C) for use inside the cell chambers of the cell encapsulating device assemblies.

FIGS. 3-70 also illustrate that the device assemblies similar to other planar drug delivery systems, each cell chamber 100 of the large capacity device assembly can contain a port 20, 30 or loading tube at one end or at each end. Still other cell chambers can contain a scaffold, preferably, a foam or reticulated scaffold, preferably any internal matrix which provides increased oxygen penetration or perfusion, in the interior of each cell chamber or the cell chamber core, to facilitate cell survival and/or cell product distribution as discussed in more detail below and shown in FIG. 71.

Example 3

Methods for Optimizing Oxygen Transport and Increasing Insulin Production

Applicants have previously demonstrated that PEC progenitors are tolerant to hypoxic conditions, such as that which occurs during and after transplantation, as compared to mature adult islets. For example, in allo- and auto-transplantations, lack of vascularization and cell hypoxia at and during transplantations is a major cell survival issue. Still, improving and providing sufficient nutrients to the cells at the core of the chamber can be optimized.

Various matrices have been explored to improve vascularization at the interface between the host and the device, however, a matrix or foam in the interior of the cell chamber has not been well described. Because such a matrix consists of interconnected cavities and pockets, it provides a suitable architecture for housing and even distribution of cell aggregates throughout the cell chamber or lumen, while at the same time acts as a conduit or channel to provide oxygen and other nutrients to the cells to promote survival. At least one advantage of using silicone derived elastomers as the matrix material is because of its high oxygen solubility which allows the material to function as an oxygen conduit or a means for conveying oxygen or oxygenated suspension or fluid towards the core of the cell chamber.

To determine whether silicone elastomers could potentially improve cell survival at the core of the cell chamber, two (2) silicone derived matrices were initially tested: silicone fibers or silicone hollow fibers, and foam made from a silicone-based mixture. Silicone hollow fibers have exceptional gas transfer properties (PermSelect membrane modules by MedArray) because silicone is dense (non-porous) and it prevents liquids from passing through the membrane applications; thus allowing for its wide use with liquids regardless of surface tension. PermSelect membrane modules for example provide packed bundles of uniformly spaced hollow fibers with various membrane surface areas of 10 $cm^2$ (PDMSXA-10), 2,500 $cm^2$ (PDMSXA-2500), 1 $m^2$ (PDMSXA-1.0) and 2.1 $m^2$ 2 (PDMSXA-2.1), however, other nominal membrane surface areas can be manufactured and tested for other custom uses. These silicone hollow fibers were assembled into a mat for placement into a device. Table 4 below shows the dimensions of the components of the mat and FIGS. 71A-B show images demonstrating how the hollow fibers are woven or knitted together using, a polyester yarn. These silicone fiber mats can be made as single or a plurality of layers, or single mats can be stacked. Mats were then cut to fit inside the lumen of a device, e.g., an EN20 device. The devices were then loaded with about 6 million PEC, and implanted into mice substantially as described previously by Applicant's in patent and non-patent publications.

TABLE 4

Silicone hollow fiber mat

DIMENSIONS

| Silicone (PDMS) | Dimensions |
| --- | --- |
| Fiber Outside Diameter (OD) | 300 mm (0.0118 in.) |
| Fiber Inside Diameter (ID) | 190 mm (0.0075 in.) |
| Membrane (Fiber Wall)Thickness | 55 mm (0.0022 in.) |

Similar to the silicone hollow fiber mats, silicone-based foam was made for insertion into the cell chamber. Methods for production of porous matrix or porous silicone material are described in detail in U.S. Pat. No. 7,192,450 to Dexcom, Inc., U.S. Pat. Nos. 5,624,674 and 5,605,693 to SM TECHNOLOGIES. Still other methods of making other types of biostable foams are known to one of ordinary skill in the art could be employed to create the structure of preferred embodiments. For example, U.S. Pat. No. 3,929,971 to Roby discloses a method of making a synthetic membrane having a porous microstructure made by converting calcium carbonate coral materials to hydroxyapatite while at the same time retaining the unique microstructure of the coral material. As another example, U.S. Pat. No. 6,520,997 to Pekkarinen discloses a photolithographic process for creating a porous membrane. In one exemplary embodiment, the foam was formed by mixing approximately 500 grams of sugar crystals with approximately 15 grams of water for about 3-6 minutes. Different architectures or cavity sizes can be obtained by varying the sugar crystal size (e.g., average diameter of about 90 to about 250 microns) and the amount of water added to the sugar prior to casting into the mold. The mixture was then pressed into a 6-well tissue culture dish which served as the mold and dried at room temperature overnight. Other methods of drying the sugar crystal mixture can be employed, e.g. baking it at suitable temperatures for a suitable period of time. A silicone elastomer, specifically a two part platinum cure silicone elastomer (NuSil Silicone Technology Part # MED-6015) was mixed at a ratio of about 10:1, part A:B, as per manufacturer's instructions, and evenly applied to the surface of the sugar mold at a ratio of about 3 grams of silicone per 962 mm2 surface area of sugar mold. A vacuum was applied to the mold to pull the silicone through the pores in the mold for about 6 minutes or a suitable time such that all the silicone has filled the cavities in the mold and cured at about 40° C. or some suitable temperature overnight. The sugar mold was then dissolved using deionized water, resulting in a shallow cylinder of porous silicone (foam) in the shape of the 6-well tissue culture well. FIG. 71C shows a cross-section of one embodiment of a luminal matrix comprising of silicone three-dimensional matrix or foam inserted between membranes that form the cell chamber. FIG. 71C also shows that the foam has a plurality of interconnected cavities or open spaces and the cavities are interconnected substantially throughout and can be formed in layers having different cavity dimensions.

The foam however is too thick to be wholly incorporated into at least an EN20 device, so it was cut into about 300 micron thick slices by embedding it in optimum cutting temperature (OCT) compound prior to cutting it on a cryostat. Alternatively, the silicone foam can also be placed in a histological tissue processor and embedded with paraffin and sectioned on a microtome. The OCT compound was removed by washing it many times in water, and the paraffin was removed by washing it many times in xylene, followed by alcohol and then water. The foam insert was then cut into dimensions to fit inside a device, specifically an EN20 device. The EN20-foam device was then loaded with about 6 million PEC, sealed and implanted subcutaneously as previously described.

Figure 72:
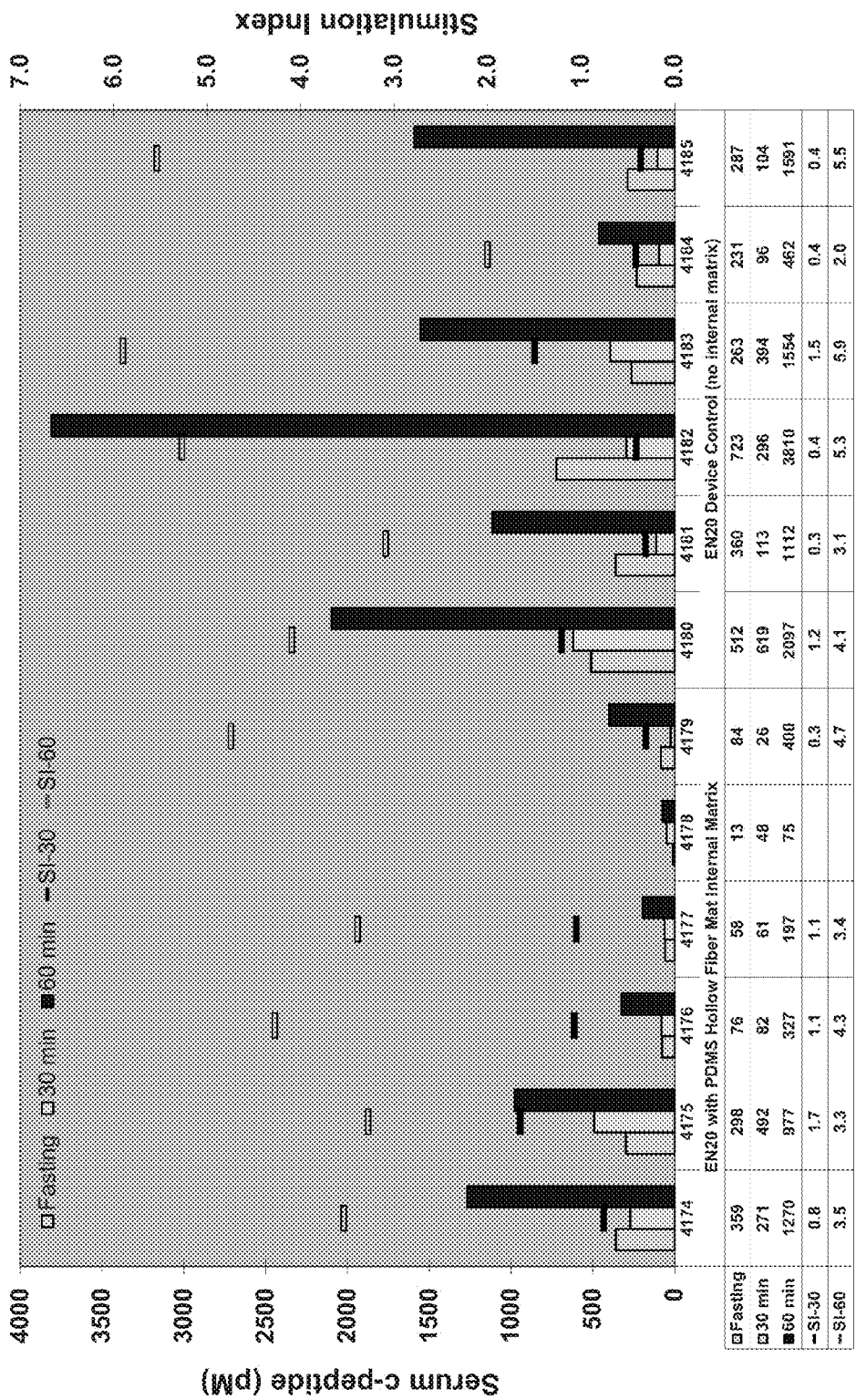
FIG. 72 is a graph showing the concentrations of human C-peptide in sera of implanted mice for six experimental and six control animals. The level of glucose responsive function in vivo was analyzed at 13 weeks post implantation or engraftment at fasting, and 30 min and 60 min after intraperitoneal glucose administration. All animals received encapsulated PEC grafts (Encaptra® EN20, or EN20, ViaCyte, San Diego, Calif.), with or without a silicone hollow fiber luminal matrix.

In total, six EN20 devices were pre-loaded with each of the silicone hollow fiber mats (Animal Nos. 4174, 4175, 4176, 4177, 4178 and 4179) and porous silicone film matrix (data not shown) and the same number of controls or EN20 devices without a matrix (Animal Nos. 4180, 4181, 4182, 4183, 4184 and 4185); see FIG. 72. All 12 devices received about 6 million PEC (about twice the amount regularly loaded in this size device) and implanted subcutaneously on the dorsum of an immune-compromised mice (e.g. SCID-Beige and Rag2). At 13 weeks after implantation, mice were fasted overnight, and injected intra-peritoneally with a glucose solution at a dose of 3 mg/kg body weight. Blood samples were taken at fasting and again at 30 min and 60 min after glucose administration. Serum c-peptide was measured using an ELISA kit that is specific for human c-peptide and the results are shown in FIG. 72. Again, methods for determining serum c-peptide have been previously well described by Applicant's patent and non-patent publications.

The results in FIG. 72 indicate that as compared to the control animals, the encapsulated PEC grafts with the silicone hollow fibers appear to have comparable function as assessed by serum c-peptide levels at 13 weeks post implantation. For example, compare serum human c-peptide levels 60 minute post glucose stimulation from animal nos. 4174 (1270 pM), 4175 (977 pM) and 4176 (327 pM) from PEC grafts with hollow fibers to animal nos. 4181 (1112 pM) and 4184 (462 pM) from PEC grafts without hollow fibers. However, no PEC-hollow fiber grafts had as robust function as that observed in control animal 4182.

Animal no. 4174 was sacrificed for histological analysis of the PEC-hollow fiber graft. FIG. 73 shows a cross-section of the encapsulated graft or explant and stained with hematoxylin and eosin (FIG. 73A) and insulin (FIG. 73B). Cells from the PEC grafts fill the chamber and reside intimately close to the hollow fibers. Interestingly, insulin positive staining cells (brown, FIG. 73B) appear in the crevice between adjacent hollow fibers (about 256 μm from the outer chamber membrane) indicating that the silicone fibers do function as a conduit to draw more oxygen into the core of the chamber. Cells at the core as compared to cells closest to the semi-permeable membrane over the long term can become necrotic. So, although, these PEC-hollow fiber grafts did not out-perform the most robust of the control PEC grafts, the silicone based hollow fibers may provide long term cell survival advantages to those cells near the chamber core.

Example 4

Figure 74:
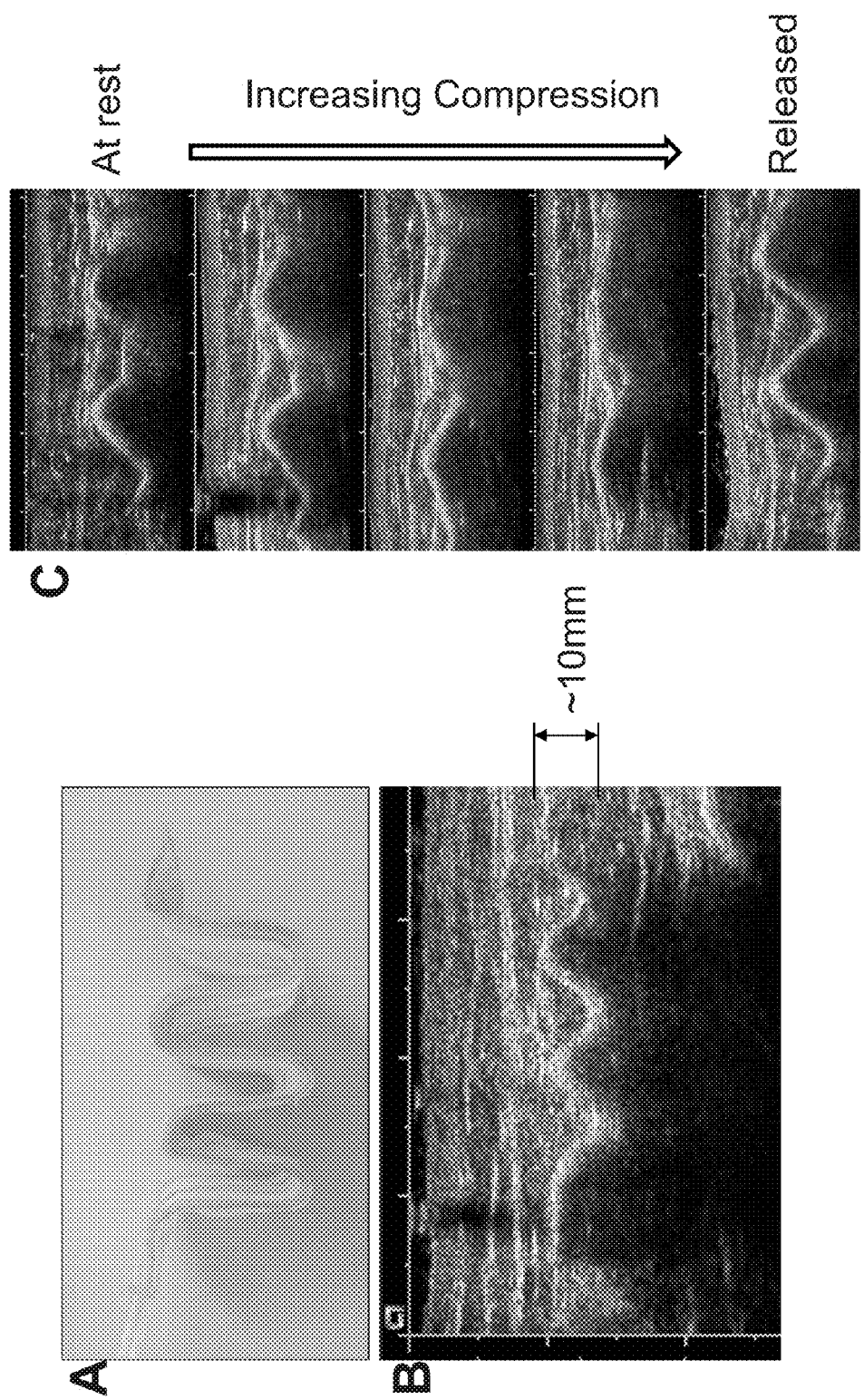
FIGS. 74A-C are ultrasound images showing a 3-dimensional cell encapsulating device assembly prototype of a EN250 device (FIG. 74A) implanted in a human (fresh) cadaver and ultrasonically imaged. The U-shape EN250 device prototype is shown can be observed before, during, and after a compressive load was applied to the cadaver in (FIGS. 74B & C).

3-Dimensional Devices Intercallate in the Body when Implanted and Withstand High Compressive Loads without Changing Shape One major embodiment of this invention is a 3dimensional device capable of high cell volume capacity while at the same time constraining the overall surface area or footprint of the device when implanted. To determine whether the described 3-dimensional large capacity devices as described herein and above would wholly intercalate into the body once implanted and maintain their shape and form in view of various compressive loads, a flat (planar) EN250 device was bent substantially into a 3-dimensional, accordion-shaped, device as described above in Example 2 (FIG. 74A). The footprint of the new 3-dimensional device was about 50% of that of the original flat sheet device with a height of about 10 mm. The 3-dimensional device (FIG. 74A) was implanted in a human (fresh) cadaver and then ultrasonically imaged. FIG. 74B shows that the subcutaneous fat or skin readily intercalates into the valleys of the corrugated 3-dimensional device and that the outline of the device is easily observed by ultrasound imaging.

Since the device was well intercalated, a test was performed to determine whether under instances of high pressure, the device would maintain its bent 3-D form, or be flattened and remain such, or move from the original implantation site. A compressive load of about 20-30 lbs. was applied directly to the site on the cadaver where the device was implanted subcutaneously (under the Scarpia's fascia). FIG. 74C shows the same device imaged before, during, and after application of the compressive load at the same implantation site. The device becomes flattened with increasing compressive load pressure at the site, however, upon release of the load, the device returns to its original bent accordion-shaped form. The device does not substantially move and the skin remains intercalated in the folds and valleys of the device.

This test demonstrates that the herein described three-dimensional macro-encapsulation devices can become intercalated into the body when implanted, withstand high compressive loads without changing their shape or change in their overall footprint and do not substantially move from the initial site of implantation.

Example 5

Devices can be Imaged In Vivo Using Ultrasound

A major concern for any cell encapsulation therapy is safety, not only with regard to the cell product but also device safety and integrity. And although device assembly manufacture includes performance of a battery of quality control tests to ensure the integrity of the device (e.g. pressure decay and the like), it is remote but possible that once the encapsulated cell product is implanted in the body, there may arise a time and event which may cause a breach (leak) of the device. A breach of the device may be caused by abnormal cell growth inside the device (e.g. a cyst, a benign tumor) and causing the device to expand in a manner inconsistent with, for example, a normal cell graft product. Alternatively, a device can be breached mechanically or physically at the implantation site due to body injury or body puncture. Hence, there is a need to monitor the device, preferably to visually monitor the device periodically to ensure it is intact and has not been breached in vivo.

Applicants therefore explored whether simple, commonly used, procedures used in many hospitals and physician rooms such as ultrasound could be exploited to monitor the transplanted devices. Ultrasound uses high-frequency sound waves to create images of internal body structures. It is non-invasive and does not use radiation and certain ultrasound technologies permit the making of three dimensional images. Ultrasound exams typically take no more than 30 or 60 minutes and are typically painless. Ultrasound is widely used for examinations and can reveal enlargements in blood vessels, blood clots or narrowing of arteries or it can locate lumps in organs and tissues, and frequently used to guide a needle biopsy. Because implantation of the encapsulated cell product is anticipated to be subcutaneous (e.g., in the flank, back, upper arm and like regions), ultrasound examination is an easy and convenient out-patient procedure.

Figure 75:
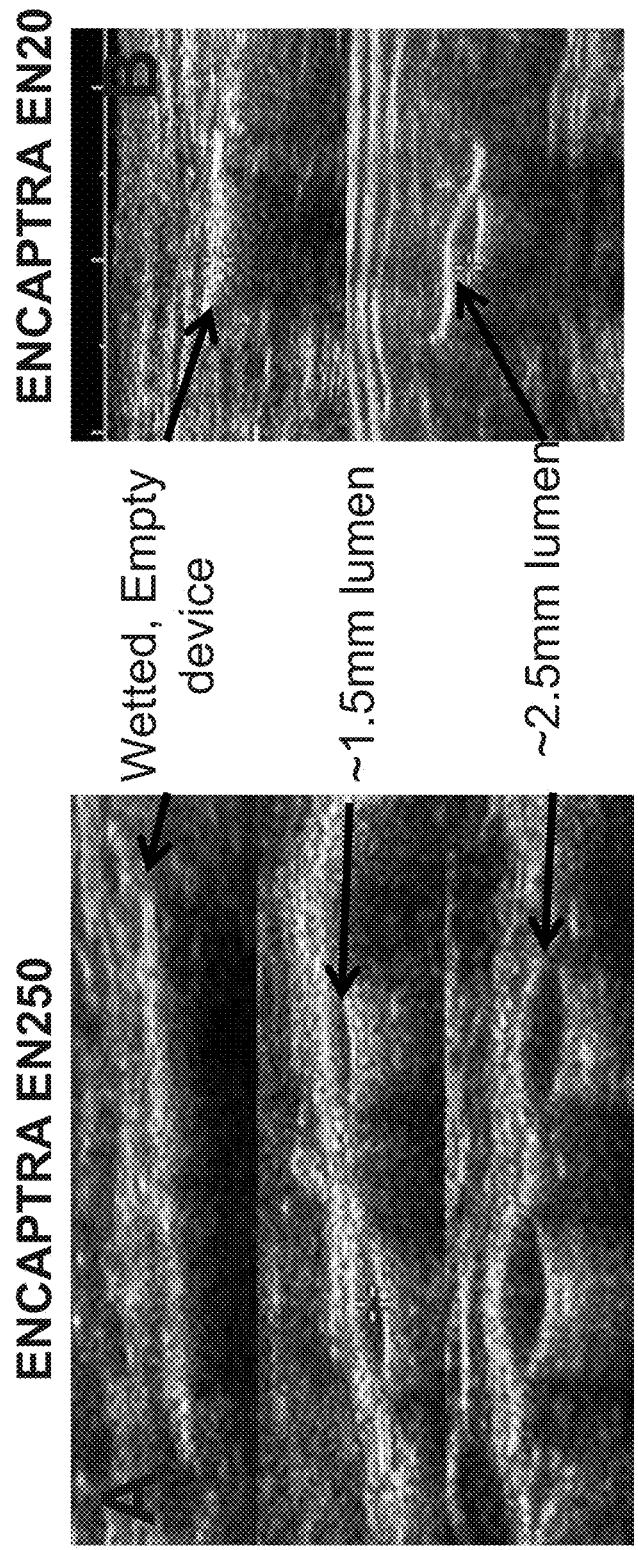
FIGS. 75A-B are ultrasound images of a wetted empty device and filled EN250 and EN20 devices.

To test the feasibility of ultrasound imaging, a flat (planar) empty and loaded EN250 and EN20 size drug delivery devices were implanted under the skin and imaged. FIG. 75 demonstrates that ultrasound imaging can detect an empty (but wetted for imaging purposes) device as well as devices loaded to expand to about 1.5 mm and about 2.5 mm. Additionally, Applicants have previously shown that high frequency ultrasound could not only show membrane separation, but show cysts growth and with contrast agents, blood flow around the device. Thus, ultrasound imaging is an easy, non-evasive means to periodically monitor the integrity of the device. In the event there was an abnormal expansion of the device or there was a device breach, the device can be surgically removed from the body; again, as an out-patient procedure.

Examples 4 and 5 demonstrate that no invention is necessary to image and monitor the device in vivo. These and other means of imaging and external testing of the integrity of the device in vivo are contemplated herein.

Accordingly, it will be apparent to one skilled in the art that varying substitutions, modifications or optimization, or combinations may be made to the embodiments disclosed herein without departing from the scope and spirit of the invention.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

EMBODIMENTS

Embodiment 1

A cell encapsulating assembly for implanting into a mammalian host, said assembly comprising at least two chambers for encapsulating living cells, wherein the assembly comprises a first seal at a peripheral edge of the assembly, thereby forming the encapsulating assembly, and at least a second seal, wherein said second seal is within said cell encapsulating assembly and forms the periphery of a the cell chambers.

Embodiment 2

The assembly of embodiment 1, wherein said second seal is further folded at an angle and decreases the total footprint of the assembly as compared to the assembly without the fold in the second seal.

Embodiment 3

The assembly of embodiment 2, wherein the assembly maintains substantially the same cell volume capacity with and without the fold in the second seal.

Embodiment 4

The assembly of embodiment 1, wherein the assembly comprises a semi-permeable membrane.

Embodiment 5

The assembly of embodiment 1, wherein the assembly has a third seal or fourth seal within the cell chamber formed by the second seal.

Embodiment 6

The assembly of embodiment 1 further comprising of at least one loading port.

Embodiment 7

The assembly of embodiment 1 further comprising two loading ports.

Embodiment 8

The assembly of embodiment 1, wherein the assembly further comprises living cells.

Embodiment 9

The assembly of embodiment 6, wherein the living cells are human pancreatic and duodenal homeobox gene 1 (PDX1)-positive pancreatic progenitor cells.

Embodiment 10

The assembly of embodiment 6, wherein the living cells are human endocrine precursor cells.

Embodiment 11

A device assembly comprising: a first sealed edge; a second seal within the first seal forming the periphery seal of a cell chamber; and wherein the second and partition seal within the cell chambers do not increase the surface area of the device assembly.

Embodiment 12

The assembly of embodiment 11, wherein the second seal is folded.

Embodiment 13

The assembly of embodiment 12, wherein the second seal is folded from zero to 90 degrees.

Embodiment 14

The assembly of embodiment 12, wherein the second seal is folded from zero to 45 degrees.

Embodiment 15

The assembly of embodiment 12, wherein the second seal is folded from zero to 30 degrees.

Embodiment 16

The assembly of embodiment 12, wherein the second seal is folded from zero to 40 degrees.

Embodiment 17

The assembly of embodiment 12, wherein the second seal is folded from zero to 90 degrees.

Embodiment 18

The assembly of embodiment 12, wherein the second seal is folded at zero degree.

Embodiment 19

The assembly of embodiment 12, wherein the second seal is folded at 40 degrees.

Embodiment 20

The assembly of embodiment 12, wherein the second seal when folded reduces the total footprint of the assembly.

Embodiment 21

The assembly of embodiment 11, further comprising a partition seal wherein the partition seal is within the second seal and reduces the chamber thickness.

Embodiment 22

The assembly of embodiment 11, further comprising of at least one loading port.

Embodiment 23

The assembly of embodiment 11, further comprising two loading ports.

Embodiment 24

The assembly of embodiment 11, wherein the assembly further comprises living cells.

Embodiment 25

The assembly of embodiment 24, wherein the living cells are human pancreatic and duodenal homeobox gene 1 (PDX1)-positive pancreatic progenitor cells.

Embodiment 26

The assembly of embodiment 24, wherein the living cells are human endocrine precursor cells.

Embodiment 27

The assembly of embodiment 11, further comprising a matrix in the chamber interior.

Embodiment 28

The assembly of embodiment 27, wherein the matrix comprises a biostable material that facilitates oxygen and nutrient uptake.

Embodiment 29

A medical device that is configured to reduce the device footprint.

Embodiment 30

A device assembly comprising at least two cell chambers.

Embodiment 31

The assembly of embodiment 30 wherein the two chambers are in a first unfolded configuration.

Embodiment 32

The assembly of embodiment 31 wherein the two chambers are in a second folded configuration.

Embodiment 33

A device assembly that comprises at least two chambers wherein the chambers are configured to reduce the footprint of the device assembly.

Embodiment 34

The assembly of embodiment 33 wherein the surface area of the chambers stays the same when configured to reduce the footprint of the device assembly.

Embodiment 35

A 3-dimensional cell encapsulating assembly, said assembly comprising at least two cell chambers for encapsulating living cells, a cell-free region along the longest axis separating the cell chambers, wherein the cell-free region is bent to form folds and wherein the folds decrease the effective area of the assembly as compared to the assembly without the folds, thereby forming a 3-dimensional cell encapsulating device.

Embodiment 36

The assembly of embodiment 35, wherein the assembly maintains substantially the same cell volume capacity with or without the folds.

Embodiment 37

The assembly of embodiment 35, wherein the assembly comprises a semi-permeable membrane.

Embodiment 38

The assembly of embodiment 35, wherein the assembly comprises at least two, three, four, five, six, seven, eight or more cell chambers.

Embodiment 39

The assembly of embodiment 35 further comprising of at least one loading port.

Embodiment 40

The assembly of embodiment 35 further comprising two loading ports.

Embodiment 41

The assembly of embodiment 35, wherein the living cells are definitive endoderm-lineage cells.

Embodiment 42

The assembly of embodiment 35, wherein the living cells are human pancreatic and duodenal homeobox gene 1 (PDX1)-positive pancreatic progenitor cells.

Embodiment 43

The assembly of embodiment 35, wherein the living cells are human endocrine precursor cells.

Embodiment 44

The assembly of embodiment 35, wherein the living cells are human immature beta cells.

Embodiment 45

The assembly of embodiment 35, further comprising a cell chamber matrix having a plurality of interconnected cavities or pores to disperse the living cells and to improve oxygen distribution inside the cell chamber.

Embodiment 46

The assembly of embodiment 45, wherein the interconnected cavities have different cavity dimensions.

Embodiment 47

The assembly of embodiment 45, wherein the matrix is polydimethylsiloxane (PDMS), polydimethylsiloxane monoacrylate, and polydimethylsiloxane monomethacrylate.

Embodiment 48

The assembly of embodiment 45, wherein the matrix is a silicone elastomer.

Embodiment 49

The assembly of embodiment 45, wherein the matrix is a polydimethylsiloxane (PDMS).

Embodiment 50

The assembly of embodiment 35, wherein the cell chambers are parallel to each other.

Embodiment 51

The assembly of embodiment 35, wherein the cell chambers are separated by about 20 degrees.

Embodiment 52

The assembly of embodiment 35, wherein the cell chambers are separated by about 40 degrees.

Embodiment 53

The assembly of embodiment 35, further comprising a partition seal within the cell chamber.

What is claimed is:
1. A cell encapsulating assembly, said assembly comprising at least two cell chambers and a cell-free region along the longest axis separating the cell chambers, wherein the cell-free region is bent 5 to 175 degrees.

2. The assembly of claim 1, wherein the assembly comprises a semi-permeable membrane.

3. The assembly of claim 1, wherein the assembly comprises at least three, four, five, six, seven, eight or more cell chambers.

4. The assembly of claim 1, further comprising at least one loading port.

5. The assembly of claim 1, further comprising definitive endoderm-lineage cells.

6. The assembly of claim 1, further comprising human immature beta cells.

7. The assembly of claim 1, further comprising a cell chamber matrix having a plurality of interconnected cavities or pores to disperse the living cells and to improve oxygen distribution inside the cell chamber.

8. The assembly of claim 7, wherein the interconnected cavities have different cavity dimensions.

9. The assembly of claim 7, wherein the matrix is polydimethylsiloxane (PDMS), polydimethylsiloxane mono acrylate, and polydimethylsiloxane monomethacrylate.

10. The assembly of claim 7, wherein the matrix is a silicone elastomer.

11. The assembly of claim 7, wherein the matrix is a polydimethylsiloxane (PDMS).

12. The assembly of claim 1, wherein the cell chambers are separated by about 20 degrees.

13. The assembly of claim 1, wherein the cell chambers are separated by about 40 degrees.

14. A encapsulating assembly, said assembly comprising at least two cell chambers, a cell-free region along the longest axis separating the cell chambers, wherein the cell-free region is bent 5 to 175 degrees, further comprising human endocrine precursor cells.

15. The assembly of claim 14, further comprising human pancreatic and duodenal homeobox gene 1 (PDX1)-positive pancreatic progenitor cells.

16. The assembly of claim 1, further comprising a partition seal within the cell chamber.

17. A cell encapsulating assembly, said assembly comprising at least two cell chambers and a cell-free region along the longest axis separating the cell chambers, wherein the cell-free region is bent 5 to 175 degrees and further comprising pancreatic and duodenal homeobox gene 1 (PDX1)-positive pancreatic progenitor cells.

* * * * *